United States Patent [19]

Lampropoulos et al.

[11] Patent Number: 5,201,753
[45] Date of Patent: * Apr. 13, 1993

[54] TOTALLY SELF-CONTAINED, DIGITALLY CONTROLLED, DISPOSABLE SYRINGE INFLATION SYSTEM, AND METHOD FOR MONITORING, DISPLAYING AND RECORDING BALLOON CATHETER INFLATION DATA

[75] Inventors: Fred P. Lampropoulos; Steven R. Taylor, both of Salt Lake City; Thomas D. Stout, Sandy; Jeffrey D. Salisbury, Ogden, all of Utah

[73] Assignee: Merit Medical Systems, Inc., Salt Lake City, Utah

[*] Notice: The portion of the term of this patent subsequent to Aug. 4, 2009 has been disclaimed.

[21] Appl. No.: 664,587

[22] Filed: Mar. 4, 1991

Related U.S. Application Data

[63] Continuation-in-part of Ser. No. 324,938, Mar. 17, 1989, Pat. No. 5,135,488.

[51] Int. Cl.$^5$ .................................... A61M 29/00
[52] U.S. Cl. ............................ 606/192; 606/194; 606/191; 604/96; 604/97; 604/100
[58] Field of Search ......................... 604/96–100; 606/191–194

[56] References Cited

U.S. PATENT DOCUMENTS

| | | |
|---|---|---|
| 383,940 | 6/1888 | Brinkerhoff . |
| 404,105 | 5/1889 | Overlach . |
| 446,125 | 2/1891 | Schirmer . |
| 466,125 | 2/1891 | Schirmer . |
| 577,682 | 2/1897 | Eissner . |
| 730,054 | 6/1903 | Sheets . |
| 1,661,818 | 3/1928 | Cook . |
| 1,707,880 | 4/1929 | Sheets . |
| 2,656,836 | 10/1953 | Hickey ........................... 128/218 |
| 2,672,866 | 3/1954 | Kater .............................. 128/218 |
| 2,699,168 | 1/1955 | Lewis ............................. 128/218 |
| 2,724,385 | 11/1955 | Lockhart ....................... 128/261 |

(List continued on next page.)

FOREIGN PATENT DOCUMENTS

| | | |
|---|---|---|
| 545415 | 8/1957 | Canada . |
| 0119296 | 9/1984 | European Pat. Off. . |
| 1242737 | 8/1960 | France . |
| 2083364A | 3/1982 | United Kingdom . |

OTHER PUBLICATIONS

"ACS Accessories Offer Optimum Efficiency in Your Angioplasty Procedures," Eli Lilly and Company.
Advertising brochure of North America Instrument Corporation entitled "The NAMIC 10cc Angiographic Syringe Features."

(List continued on next page.)

Primary Examiner—Robert A. Hafer
Assistant Examiner—Kerry Owens
Attorney, Agent, or Firm—Workman Nydegger Jensen

[57] ABSTRACT

An electronically controlled syringe system for connection to a balloon catheter or other balloon-type member and for automatically monitoring, displaying and recording inflation data when the syringe system is used to inflate the balloon of the catheter or other balloon-type member. A syringe having a barrel and a syringe plunger is selectively operable to increase fluid pressure applied to the balloon catheter or other balloon member by sliding the plunger further into the barrel. Positive pressure applied to the balloon catheter or member is released by withdrawing the syringe plunger toward the rear of the barrel. A piezoresistive semiconductor transducer housed on the barrel of the syringe senses fluid pressure applied by the syringe. The electric signal output by the transducer is input to a controller where the signal is digitally processed so as to derive and record therefrom electronic data representing the magnitude of applied fluid pressure, and so as also to derive the length of time that fluid pressure is applied. The electronic data representing this information is automatically displayed and recorded. In one embodiment, the controller is also mounted onto the syringe barrel to provide a digitally controlled inflation syringe system that is completely self-contained, and disposable.

31 Claims, 20 Drawing Sheets

U.S. PATENT DOCUMENTS

| | | | |
|---|---|---|---|
| 2,736,315 | 2/1956 | Feeney | 128/218 |
| 2,764,978 | 10/1956 | Everett | 128/215 |
| 3,080,866 | 3/1963 | Friedman | 128/218 |
| 3,388,941 | 6/1968 | Marcus | 294/4 |
| 3,478,937 | 11/1969 | Solowey | 222/386 |
| 3,491,757 | 1/1970 | Arce | 128/221 |
| 3,529,596 | 9/1970 | Garner | 128/145.6 |
| 3,698,381 | 10/1972 | Federico et al. | 128/1 R |
| 3,720,199 | 3/1973 | Rishton et al. | 128/1 D |
| 3,884,229 | 5/1975 | Raines et al. | 128/221 |
| 3,931,822 | 1/1976 | Marici | 128/351 |
| 3,966,358 | 6/1976 | Heimes et al. | 417/12 |
| 3,985,123 | 10/1976 | Herzlinger et al. | 128/2.05 F |
| 3,992,926 | 11/1976 | Berryhill | 73/80 |
| 4,016,871 | 4/1977 | Schiff | 128/2.06 R |
| 4,057,050 | 11/1977 | Sarstedt | 128/2 F |
| 4,063,662 | 12/1977 | Drummond et al. | 222/31 |
| 4,086,653 | 4/1978 | Gernes | 364/564 |
| 4,106,002 | 8/1978 | Hogue, Jr. | 340/626 |
| 4,182,344 | 1/1980 | Benson | 128/207.15 |
| 4,254,773 | 3/1981 | Waldbillig | 128/348 |
| 4,266,550 | 5/1981 | Bruner | 128/349 |
| 4,267,846 | 5/1981 | Kontos | 128/765 |
| 4,285,340 | 8/1981 | Gezari et al. | 128/205.24 |
| 4,323,071 | 4/1982 | Simpson et al. | 128/343 |
| 4,332,254 | 6/1982 | Lundquist | 128/344 |
| 4,370,982 | 2/1983 | Reilly | 604/98 |
| 4,384,470 | 5/1983 | Fiore | 73/4 R |
| 4,404,974 | 9/1983 | Titus | 128/670 |
| 4,418,392 | 11/1983 | Hata | 364/571 |
| 4,439,185 | 3/1984 | Lundquist | 604/97 |
| 4,444,335 | 4/1984 | Wood et al. | 222/43 |
| 4,446,715 | 5/1984 | Bailey | 73/1 R |
| 4,446,867 | 5/1984 | Leveen et al. | 128/344 |
| 4,466,426 | 8/1984 | Blackman | 128/1.1 |
| 4,504,268 | 3/1985 | Herlitze |  |
| 4,522,194 | 6/1985 | Normann | 128/1 D |
| 4,526,196 | 7/1985 | Pistillo | 137/557 |
| 4,546,760 | 10/1985 | Suzuki et al. | 128/1 D |
| 4,557,269 | 12/1985 | Reynolds et al. | 128/675 |
| 4,568,335 | 2/1986 | Updike et al. | 604/211 |
| 4,573,978 | 3/1986 | Reilly | 604/240 |
| 4,583,917 | 4/1986 | Shah | 417/63 |
| 4,583,974 | 4/1986 | Kokernak | 604/211 |
| 4,585,010 | 4/1986 | Ascer et al. | 128/673 |
| 4,596,255 | 6/1986 | Snell et al. | 128/697 |
| 4,597,381 | 7/1986 | Oumi et al. | 128/6 |
| 4,600,015 | 7/1986 | Evans et al. | 128/780 |
| 4,601,701 | 7/1986 | Mueller, Jr. | 604/83 |
| 4,610,256 | 9/1986 | Wallace | 128/675 |
| 4,621,646 | 11/1986 | Bryant | 128/692 |
| 4,651,738 | 3/1987 | Demer et al. | 604/96 |
| 4,651,783 | 3/1987 | Demer et al. | 128/344 |
| 4,672,974 | 6/1987 | Lee | 128/673 |
| 4,710,179 | 12/1987 | Haber | 604/211 |
| 4,715,854 | 12/1987 | Vaillancourt | 604/191 |
| 4,723,938 | 2/1988 | Goodin et al. | 604/99 |
| 4,743,230 | 5/1988 | Nordquest | 604/97 |
| 4,758,223 | 7/1988 | Rydell | 604/90 |
| 4,781,192 | 11/1988 | Demer | 604/97 X |
| 4,787,368 | 11/1988 | Kageyama | 600/18 |
| 4,787,429 | 11/1988 | Valentini et al. | 141/383 |
| 4,796,606 | 1/1989 | Mushika | 600/18 |
| 4,799,491 | 1/1989 | Eckerle | 128/672 |
| 4,819,637 | 4/1989 | Dormandy | 128/325 |
| 4,820,271 | 4/1989 | Deutsch | 604/99 |
| 4,825,876 | 5/1989 | Beard | 128/675 |
| 4,830,013 | 5/1989 | Maxwell | 128/637 |
| 4,832,692 | 5/1989 | Box et al. | 604/99 |
| 4,838,684 | 6/1989 | Peterson | 604/100 |
| 4,858,615 | 8/1989 | Meinema | 128/668 |
| 4,872,483 | 10/1989 | Shah | 604/99 X |
| 4,877,035 | 10/1989 | Bogen et al. | 128/673 |
| 4,896,671 | 1/1990 | Cunningham et al. | 606/39 X |
| 4,901,731 | 2/1990 | Millar | 128/675 |
| 4,906,244 | 3/1990 | Pinchuk et al. | 606/194 |
| 4,907,596 | 3/1990 | Schmid et al. | 128/672 |
| 4,919,121 | 4/1990 | Rydell et al. | 604/97 |
| 4,940,459 | 7/1990 | Noce | 604/97 |
| 4,974,774 | 12/1990 | Nakagawa et al. | 600/18 |
| 5,004,472 | 4/1991 | Wallace | 606/194 |
| 5,009,662 | 4/1991 | Wallace et al. | 606/192 |
| 5,021,046 | 6/1991 | Wallace | 604/97 |
| 5,084,060 | 1/1992 | Freund et al. | 606/192 |

OTHER PUBLICATIONS

Advertising brochure of Spectramed, Inc.; produce prochure for "CONTROLEASE Disposable Control Syringe"; and product brochure for control syringe of COEUR Laboratories, Inc.

"Clearing the Path for a Healthy Heart," *Tristate: The Cincinnati Enquirier Magazine*, Oct. 23, 1988.

"Coronary Angioplasty," Krames Communications, 1985.

"Good News for People with Only Two Hands," SciMed Life Systems, Inc.

"Health–Critics of Angioplasty Worry About Inflated Success Claims," *U.S. News & World Report*, Jul. 25, 1988, p. 65.

"Inflation PRO: A New Dual-Support System for Angioplasty," Baxter Healthcare Corporation.

"PTCA Safe and Efficacious Performed Together With Diagnostic Angiography in Selected Cases," *Cardiovascular News*, May 1988, p. 8.

"USCI Wizard Disposable Inflation Device," C. R. Bard, Inc.

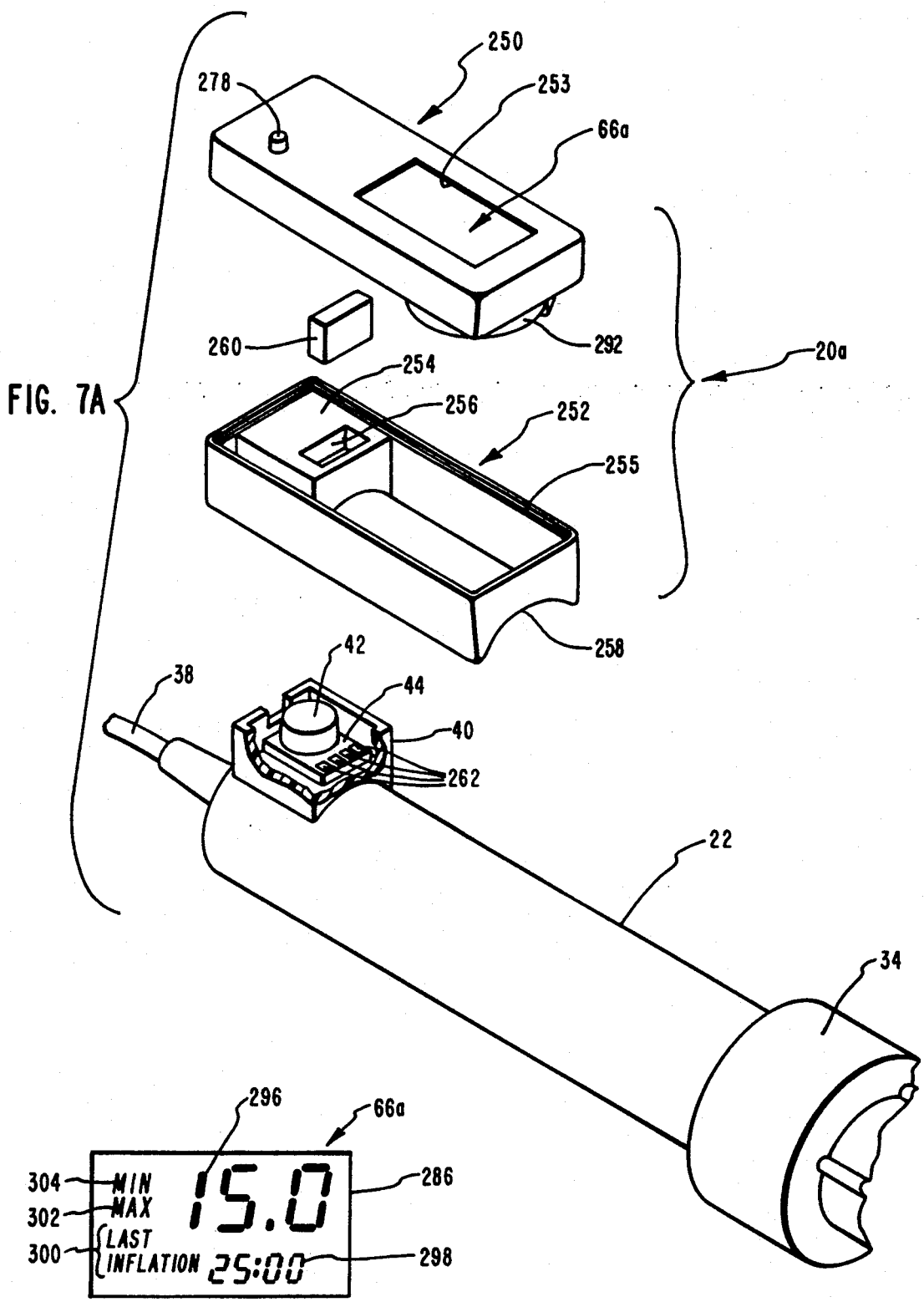

TOTALLY SELF-CONTAINED, DIGITALLY CONTROLLED, DISPOSABLE SYRINGE INFLATION SYSTEM, AND METHOD FOR MONITORING, DISPLAYING AND RECORDING BALLOON CATHETER INFLATION DATA

RELATED APPLICATION INFORMATION

This application is a continuation-in-part of copending U.S application Ser. No. 324,938 filed Mar. 17, 1989.

COPYRIGHTED MATERIALS

A portion of the disclosure of this patent document contains material to which a claim of copyright protection is made. The copyright owner has no objection to the reproduction by anyone of the patent document or the patent disclosure as it appears in the Patent and Trademark Office patent file or records, but reserves all other rights with respect to the copyrighted work.

BACKGROUND OF THE INVENTION

1. Field of the Invention

This invention relates to syringe systems that are used for controlling the inflation of a balloon-tipped catheter, and more particularly to a totally self-contained, digitally controlled, disposable syringe inflation system and its method of use so as to assist in the control of balloon catheter inflation pressures and to automatically record and display balloon catheter inflation data.

2. The Present State of the Art

Balloon-tipped catheter systems have been known and used in the medical arts for a number of years in connection with a variety of different kinds of procedures which are used, for example, in various fields of medicine, such as urology, gynecology, cardiology and others. Particularly in connection with the treatment of coronary artery disease, the use of balloon-tipped catheters and their associated syringe systems have become widely used.

Coronary artery disease is the narrowing of the arteries that feed oxygen-rich blood to the heart. Since the heart is a muscle whose primary job is to pump oxygenated blood throughout the body, the heart needs adequate amounts of oxygen to properly function. Thus, when the coronary arteries which are located on the top of the heart and through which oxygenated blood is returned to the heart become narrowed or blocked (a condition known as "stenosis"), angina can result. Angina is a symptom of coronary artery disease characterized by chest pain or pressure that can radiate to the arm or jaw, and is caused by a lack of oxygen-rich blood to the heart muscle. Coronary artery disease with its accompanying symptom of angina results from atherosclerosis, which is a build up of waxy material called plaque inside the arteries. When this happens, under exertion or stress, the heart demands more oxygen but the narrowed coronary arteries cannot supply enough oxygen-rich blood to meet the demand, resulting in angina.

Up until about ten years ago, there were two basic ways to treat coronary artery blockages: with medicine or by performing coronary artery by-pass surgery. Various kinds of medication could be administered which would decrease the work of the heart by slowing the heart rate, dilating the blood vessels, or lowering blood pressure. However, such medicinal treatment did not cure coronary artery blockage, which thus remained and which would therefore continue to present a risk that at some point the blockage would become serious enough to require surgical intervention.

In coronary artery by-pass surgery, a blood vessel from the chest or leg is grafted beyond the point of blockage so that the blood detours past the blockage in order to reach the heart. In some severe cases, multiple by-passes are performed. As is well known, coronary artery by-pass surgery is expensive, is a high risk procedure and often requires prolonged hospitalization and recovery periods.

About ten years ago, another method for treating coronary artery disease was developed, called balloon coronary angioplasty, or more technically, percutaneous transluminal coronary angioplasty (PTCA). PTCA is a much less traumatic procedure than coronary artery by-pass surgery. PTCA takes about two hours and can be done under local anesthesia, with the result that often a patient can be back on his feet and active in a matter of days. Because PTCA is much less expensive and less traumatic than by-pass surgery and yet in many cases still effectively removes blockage, PTCA has experienced a dramatic increase in the number of such procedures performed each year. For example, according to some reports, as recently as 1987 some 200,000 patients suffering from coronary artery disease were treated by PTCA. Since coronary artery disease remains the number one cause of death, with (as of 1987) some six million reported cases in the U.S. alone, PTCA may be expected to continue to play an important role in the treatment of coronary artery disease.

In performing PTCA, an introducer sheath is inserted through an incision made in the groin or in the artery of an arm. An x-ray sensitive dye is injected into the coronary artery through a catheter that is introduced through the sheath. The dye enables the doctor, through the use of real time x-ray techniques, to clearly view the arteries on a television monitor and to thereby locate the artery blockage. A balloon-tipped catheter with a guide wire at the end of it is then advanced through the artery to the point of the blockage with the help of the x-ray monitor.

As schematically illustrated in FIGS. 1A-1C, the balloon catheter 10 is advanced to the middle of the blockage 12. The catheter 10, which is filled with a fluid and is coupled at its other end to a control syringe, is manipulated by the cardiologist. Once the balloon catheter is in place, utilizing the control syringe the balloon is inflated for 20 to 60 seconds as shown in FIG. 2B. The balloon is then deflated and this procedure is repeated typically several times to compress the plaque on the arterial wall, as shown in FIG. 1C. After the results are checked, the balloon catheter and guide wire are then removed.

As will be appreciated, notwithstanding that PTCA is a much less traumatic procedure than coronary artery by-pass surgery, nonetheless exacting control with respect to inflation pressure and duration of the inflation periods is essential to the safety of the patient. For example, when the balloon catheter is completely inflated so as to begin compressing the plaque, blood flow to the heart is thereby temporarily shut off. This creates the potential for initiating cardiac arrest. Accordingly, the pressure exerted on the artery by the balloon catheter as well as the duration of the blockage created by inflating the balloon catheter must both be carefully controlled by the attending cardiologist and other personnel. The inflation pressures and duration of each inflation must be based on the cardiologist's assessment of the health of the patient and the patient's ability to withstand such a temporary stoppage of blood flow to the heart.

In the past, PTCA syringe systems have been equipped with standard strain gauges that are utilized to sense and read the pressure used for purposes of inflating a balloon catheter. Human observation of stop clocks and the like has been used to control the duration of the inflation.

While these prior art techniques have been widely used with success, there is still a serious risk of human error when using such systems. The gauges used on such syringe systems are often awkward and difficult to accurately read, and are also subject to malfunction. Thus, improper recording of inflation pressure and/or duration may occur. Accordingly, there is a need for the cardiologist and/or clinician to be able to improve the degree of control and precision with respect to the inflation procedure. There is also a need to be able to accurately record the procedure data so that in the event of any later question with respect to whether the procedure was properly carried out, there is an accurate record from which to answer such questions. The system and method of the present invention provide an effective solution to these problems which have not heretofore been fully appreciated or solved.

SUMMARY OF THE INVENTION

The system and method of the present invention have been developed in response to the present state of the art, and in particular, in response to the problems and needs in the art not heretofore fully or completely solved by syringe inflation systems used in connection with PTCA procedures. However, it is not intended that the system and method of the present invention will necessarily be limited solely to PTCA procedures, since they will also find useful application with potentially many kinds of procedures which require the utilization of inflatable balloon members for various kinds of medical procedures. Thus, it is an overall object of the present invention to provide a system and method which provide for more accurate measurement, monitoring and recording of the pressures used for inflation of a balloon-type member as well as the duration of inflation in connection with any such inflation of a balloon-type member, catheter or otherwise.

Another important object of the present invention is to provide a system and method whereby state of the art electronic technology can be utilized to assist the cardiologist or clinician in accurately measuring, displaying, monitoring and recording inflation pressures which he or she desires to achieve when utilizing a syringe system to inflate a balloon of a catheter or other balloon-type member, and which will at the same time automatically electronically record and store the inflation pressure and duration of the inflation so as to permit the data pertaining to the procedure to be later printed out and thus accurately documented and saved for later reference.

Another important object of the present invention is to provide an improved syringe system and electronic monitoring and recording system which increase the convenience and safe utilization of a balloon catheter or other balloon-type inflation member.

Yet another important object of the present invention is to provide an improved syringe system which is digitally controlled and which is totally self-contained, easy to use, and inexpensive enough in its construction as to be disposable.

These and other objects and features of the present invention will become more fully apparent from the following more detailed description taken in conjunction with the drawings and claims, or may be learned by the practice of the invention.

Briefly summarized, the foregoing and other objects are achieved in an electronically monitored syringe system that is connected to a balloon catheter or other inflatable balloon-type device through tubing. The syringe comprises a barrel and a plunger selectively operable to increase fluid pressure applied to the balloon through the connecting tubing by sliding the plunger further into the barrel, and to then remove the applied pressure by returning the plunger to the rear of the barrel. A transducer means for sensing fluid pressure applied by the syringe is placed in fluid communication with the syringe and the connecting tubing. The transducer means thereby senses applied fluid pressure and outputs an electrical signal proportional to the sensed pressure. The electrical signal output by the transducer means is then electronically processed so as to derive and record therefrom electronic data representing the magnitude of fluid pressure applied to the balloon or other balloon-type member, and so as also to derive the length of time that inflation pressure is applied to the balloon or other balloon-type member, and the electronic data representing these parameters is then automatically displayed and/or recorded. The system also comprises a display means for selectively outputting a visual display of the magnitude of the applied pressure and the corresponding length of time that inflation pressure is applied to the balloon or other balloon-type member with respect to each inflation thereof.

The electronic control system used in conjunction with the system and method of the present invention may also be optionally designed to permit the selection and input of various control parameters such as a maximum positive for applying positive inflation pressure, initializing the date and time of the procedure and/or retrieving and displaying inflation data previously recorded for any prior inflation of the balloon catheter or other balloon-type member. In this manner, the system and method of the present invention provide not only more convenient operation of the syringe when inflating the balloon catheter or other balloon-type member, but also a much safer and more accurate procedure which can be used to effectively alert a cardiologist or clinician when the appropriate levels of pressure and duration thereof have been reached with respect to a particular inflation event. The system is thus efficient and easy to operate while at the same time providing improved convenience and overall safety, and also providing accurate documentation of all inflation data for later reference.

In another presently preferred embodiment of the invention, the display means and electronic control system may be mounted along with the transducer means directly onto the syringe barrel, thus providing a totally self-contained syringe system that is completely disposable, and which provides increased convenience in terms of maintaining sterility and portability.

BRIEF DESCRIPTION OF THE DRAWINGS

The presently preferred embodiments and the presently understood best mode of the invention will be described with additional detail through use of the accompanying drawings, wherein corresponding parts are designated by the same reference numerals throughout, and in which:

FIG. 7A is a perspective illustration of a portion of the syringe system of FIG. 7, with portions of the electronic controller shown in exploded perspective to more particularly illustrate certain details thereof.

FIG. 7C is an illustration of the digital readout display which particularly illustrates the nature of the information displayed thereon when utilizing the electronic control system and syringe of FIG. 7.

DETAILED DESCRIPTION OF THE PRESENTLY PREFERRED EMBODIMENTS

The following detailed description is divided into two parts. In part one the presently preferred embodiments of the overall system are described, including a description of the syringe system, the transducer means and electronic controller by reference to FIGS. 1 through 5 and FIGS. 7 through 9. In part two the presently preferred methods by which the system of the present invention is used to electronically monitor, display and automatically record inflation data are described, including a detailed description of the presently preferred methods for programming the digital processor used in the electronic controller by reference to FIGS. 6A-6G and FIG. 10.

I. THE SYSTEM

A. General Environment and Intended Utility of the System

Figure 1A:
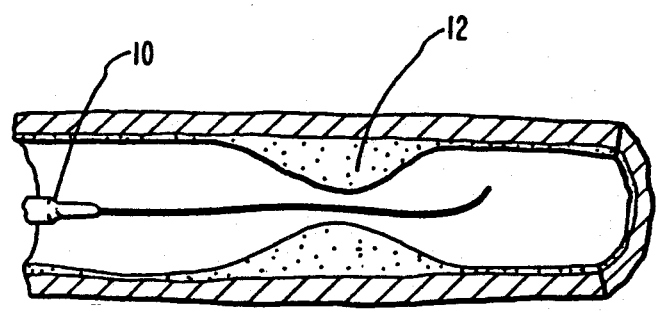
FIGS. 1A-1C are partial cross-sectional views which schematically illustrate a conventional balloon catheter being placed within a vessel such as a coronary artery containing a blockage, and showing the manner in which the blockage is essentially removed by inflation of the balloon catheter.
Figure 1B:
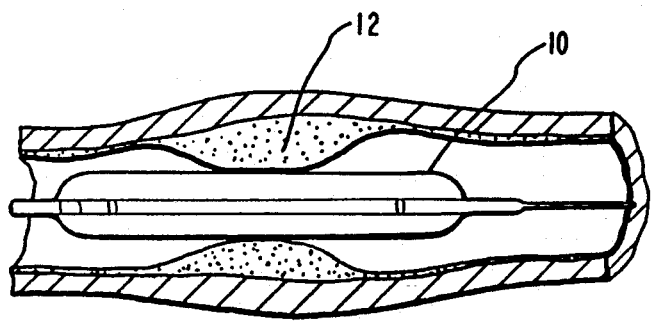
Figure 1C:
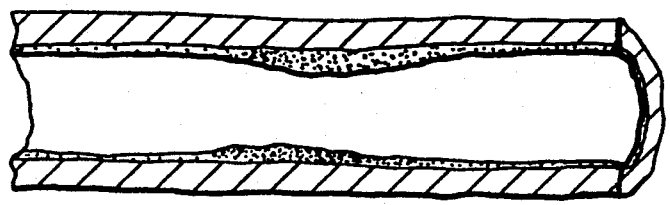

As noted above, the system and method of the present invention have been developed in response to specific needs which have been found to exist in connection with techniques that are currently in use according to the present state of the art which has developed in connection with PTCA procedures. As described in connection with FIGS. 1A-1C, PTCA is a surgical procedure used for treating coronary artery disease wherein a balloon catheter 10 is inserted through an incision made in the groin or in the artery of an arm and is then advanced through the artery by means of a guide catheter and assisted by means of an x-ray sensitive dye. The balloon catheter 10 is advanced until it is located at the middle of the blockage 12. Once located at the middle of the blockage 12, the balloon of catheter 10 is then inflated (see FIG. 1B) to a pressure that is typically between 7 and 10 atmospheres for a duration of between 20 to 60 seconds. The balloon is then deflated and the procedure is repeated a number of times, slightly increasing the inflation pressure each time so as to further compress and thereby reduce the blockage 12 created by the buildup of plaque along the wall of the artery. Once this series of inflations is completed and the artery is cleared, as shown in FIG. 1C, the balloon catheter 10 is removed.

While the system and method of the present invention are particularly useful in connection with the aforementioned PTCA procedure, the system and method of the invention are not intended to be necessarily limited to use in connection with PTCA. Rather, it is contemplated that the system and method of the invention will find useful application with respect to any procedure requiring the use of an inflatable balloon-type member. Moreover, while in PTCA the inflation pressure which is applied to the balloon catheter 10 is applied hydraulically by means of the syringe and connecting tubing which are all filled with a sterile liquid such as a solution of saline and contrast medium, in some potential applications it may be necessary or desirable to apply the inflation pressure pneumatically. Accordingly, as used herein the term "fluid pressure" is intended to apply either to a hydraulically or a pneumatically applied inflation pressure.

B. The Presently Preferred Syringe System and Electronic Controller: FIGS. 2-5 and 7-9.

1. FIGS. 2-5

The system of the present invention is comprised of a syringe that is connected to a balloon catheter or other balloon-type member through tubing. The syringe is used to apply fluid pressure to the balloon of the catheter or other balloon-type member through the tubing so as to inflate the balloon or balloon member when desired, and can also be used to deflate the balloon catheter or balloon member after it has been inflated for a selected duration. The system is also comprised of a transducer means for sensing applied fluid pressure and for outputting an electrical signal proportional to the sensed fluid pressure. The transducer means is thus preferably in fluid communication with the syringe and the tubing connected to the balloon catheter or other balloon-type member. The system also comprises an electronic circuit means connected to the transducer means for receiving the electrical signal that is output by the transducer means and for processing the electrical signal so as to derive and record therefrom electronic data representing inflation pressure applied to the balloon or balloon member as well as the length of time the inflation pressure is applied to the balloon or balloon member each time it is inflated. The system is also comprised of display means which is electrically connected to the electronic circuit means for selectively outputting a visual display of the inflation pressure and the corresponding length of time the inflation pressure is applied to the balloon or balloon member during each inflation.

Figure 2:
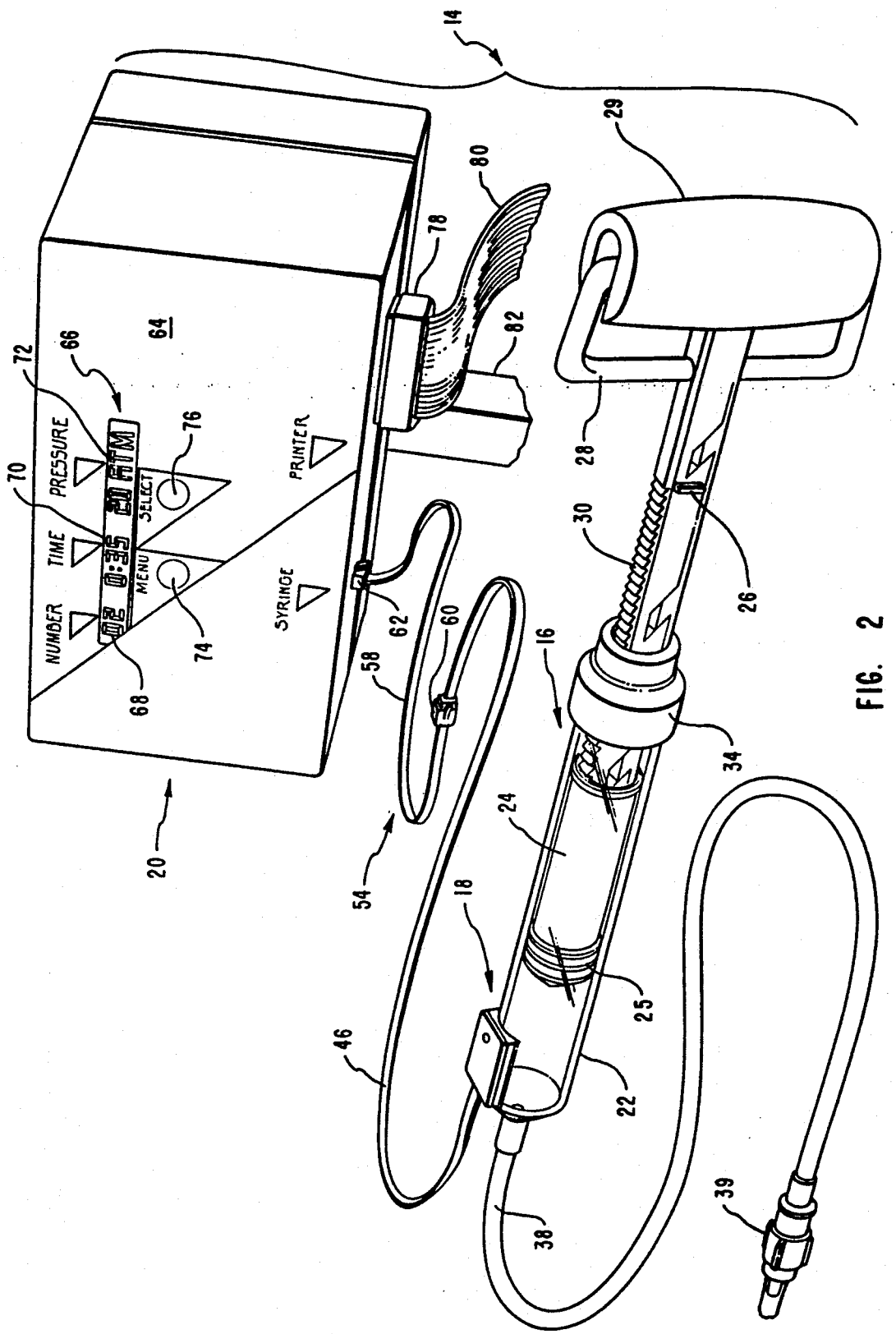
FIG. 2 is a perspective illustration showing the system of the present invention, and in particular illustrating a syringe with tubing for connection to a balloon catheter, and a transducer means mounted on the syringe and electrically connected to an electronic controller.
Figure 3:
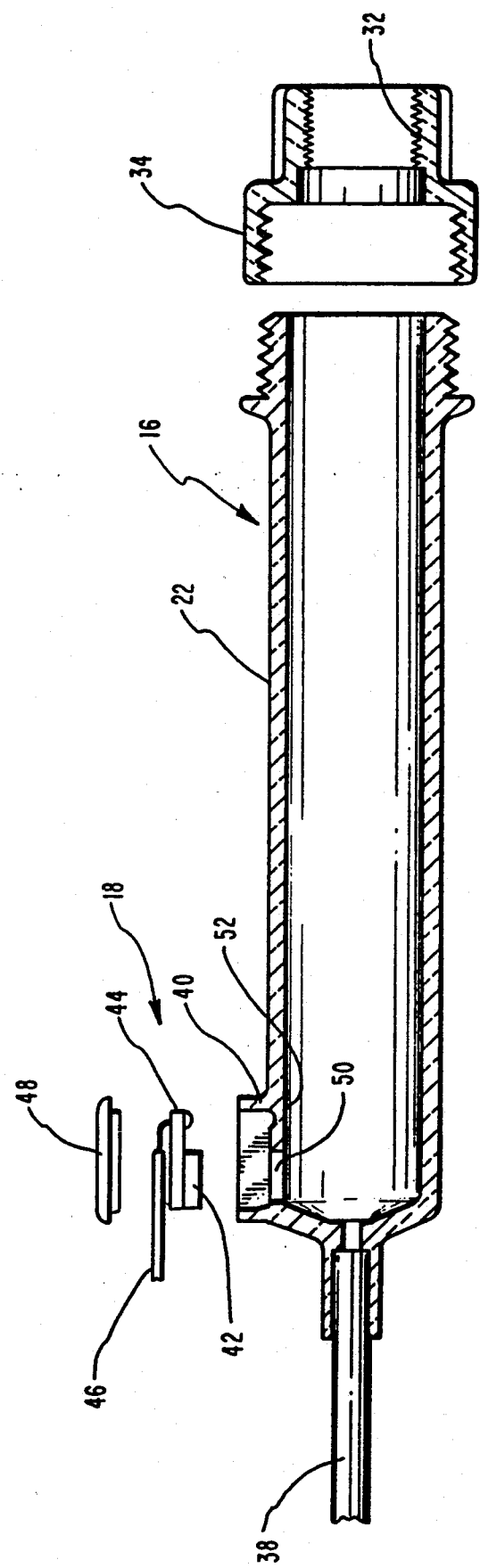
FIG. 3 is a partial cross-sectional view of the syringe barrel that more particularly illustrates one presently preferred structure and method for placing the transducer means in fluid communication with the interior of the syringe and the tubing which is connected to the balloon catheter.

In the preferred embodiment illustrated in FIG. 2, the overall system is generally designated at 14 and the syringe is generally designated at 16. With reference to FIGS. 2 and 3 taken together, the syringe 16 is comprised of a barrel 22 typically molded from transparent plastic material to permit inspection of the contents thereof. A syringe plunger 24 (FIG. 2) is slidably mounted within the barrel and is secured within the barrel 22 by means of a cap 34 which can be threaded onto or otherwise securely attached at the end of the barrel 22. The syringe plunger 24 has a threaded portion 30 which mates with corresponding threads 32 (see FIG. 3) of end cap 34.

The proximal end of plunger 24 is provided with a soft rubber bulb 25 which engages the interior of barrel 22 in a fluid-tight fit such that by sliding the syringe plunger 24 further into the barrel 22, positive pressure exerted on the fluid contained within syringe 16 and connecting tubing 38 will be applied to the balloon catheter which is connected to the tubing 38 by means of a rotatable luer connector 39. Similarly, by withdrawing the syringe plunger 24 toward the rear of the barrel 22, the positive pressure exerted on the balloon catheter will be released.

Rapid movement of the syringe plunger 24 is accommodated by means of a trigger mechanism comprising a spring-activated trigger 28 which can be retracted into handle 29 so as to disengage the threads 30 from the corresponding threads 32 of cap 34. This permits the plunger 24 to freely slide in either direction within the syringe barrel 22. By releasing the compression on trigger 28 relative to handle 29, the threads 30 are then permitted to engage the corresponding threads 32 of cap 34 so that thereafter the syringe plunger 24 can only be advanced or retracted by screwing the plunger 24 either clockwise or counter clockwise, respectively. Thus, rapid application or release of pressure applied to the balloon catheter can be accomplished by compressing the trigger 28 against handle 29 followed by movement of the syringe plunger 24 to the position desired for the approximate pressure to be applied. This can then be followed by release of the trigger 28 and screwing the plunger 24, which will permit a slow, gradual adjustment of the syringe plunger 24 to the exact pressure that is desired.

It will be appreciated that insofar as providing for application and release of positive inflation pressure, this function of syringe 16 of the system could be provided by any of a number of syringe systems which are conventional or known in the art. However, the syringe illustrated and generally described in connection with FIGS. 2 and 3 is presently preferred in connection with the system and illustrates the presently contemplated best mode of the syringe 16. A more complete description of syringe 16 and its unique design and advantages is contained in copending U.S. application Ser. Nos. 375,561 and 434,460 filed Mar. 17, 1989 and Nov. 28, 1989, respectively, which are incorporated herein by reference.

The transducer means of the system of the present invention is generally designated in FIGS. 2 and 3 at reference numeral 18. As shown best in FIG. 3, the body of syringe barrel 22 has a small housing 40 formed at the leading end of the barrel as an integral part of the syringe barrel 22. The housing 40 communicates through a small circular opening 50 formed in the sidewall of syringe barrel 22 with the interior of syringe barrel 22 for the purpose of providing fluid communication from the interior of barrel 22 and connecting tubing 38 to the transducer means, as hereinafter more fully described.

As used herein, the term "fluid communication" is intended to mean the pneumatic or hydraulic transmission (direct or indirect) of fluid pressures exerted within the syringe barrel 22 and connecting tubing 38 to the transducer means so that such fluid pressures can be sensed by the transducer means. Direct transmission of such fluid pressures would occur, for example, when a diaphragm of a piezoresistive semiconductor transducer is placed into contact (either pneumatically or hydraulically, or a combination of both) with a fluid contained in a closed system, as would be the case in the preferred embodiments illustrated and described herein. Indirect transmission could be said to occur, for example, where the transducer means is coupled to a diaphragm that in turn contacts the fluid contained in a closed system.

Figure 5A:
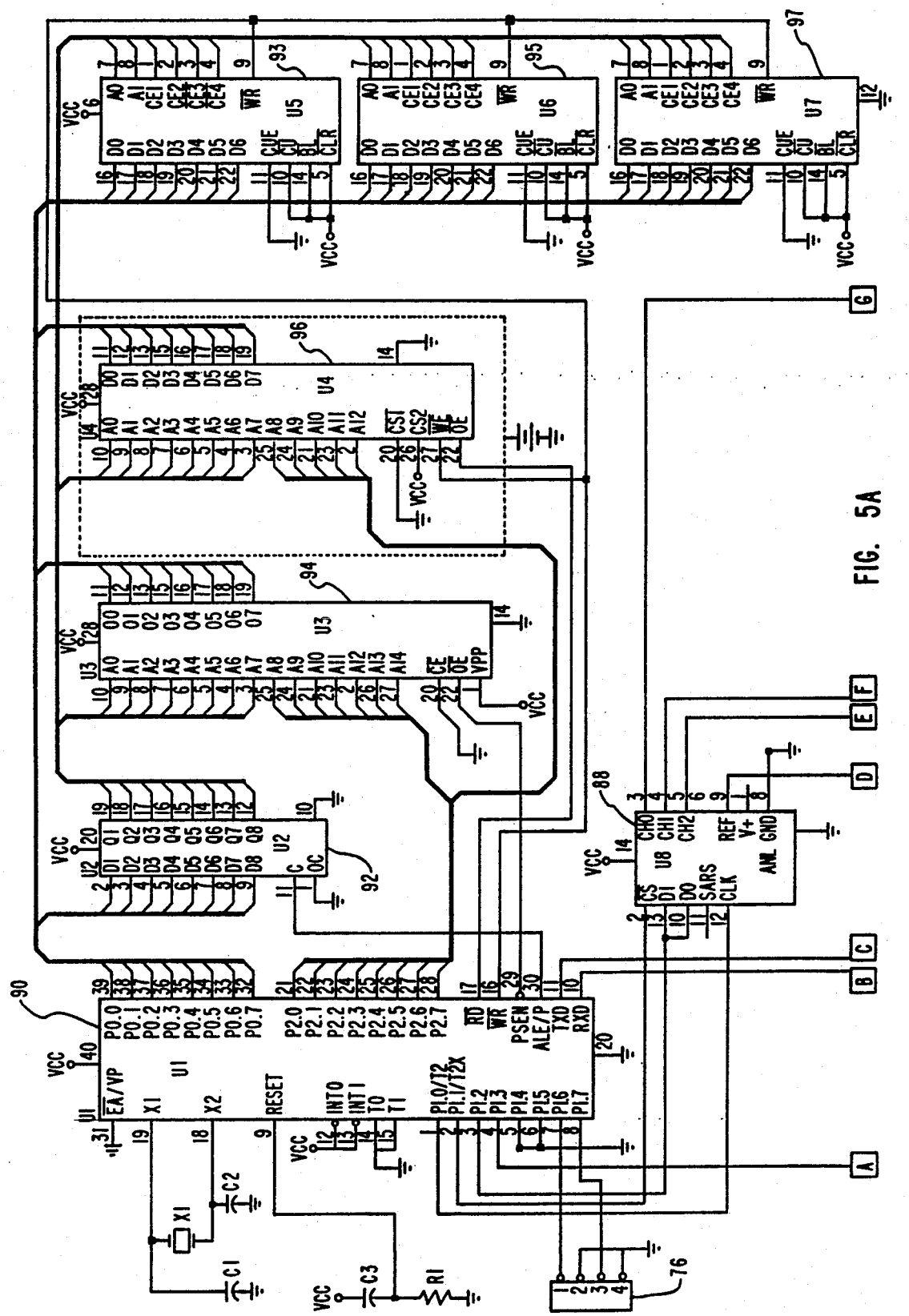
FIGS. 5A and 5B taken together constitute a detailed electrical schematic diagram which illustrate, as an example, the presently preferred embodiment and presently understood best mode for implementing the electronic circuit means of the system and method of the present invention.
Figure 5B:
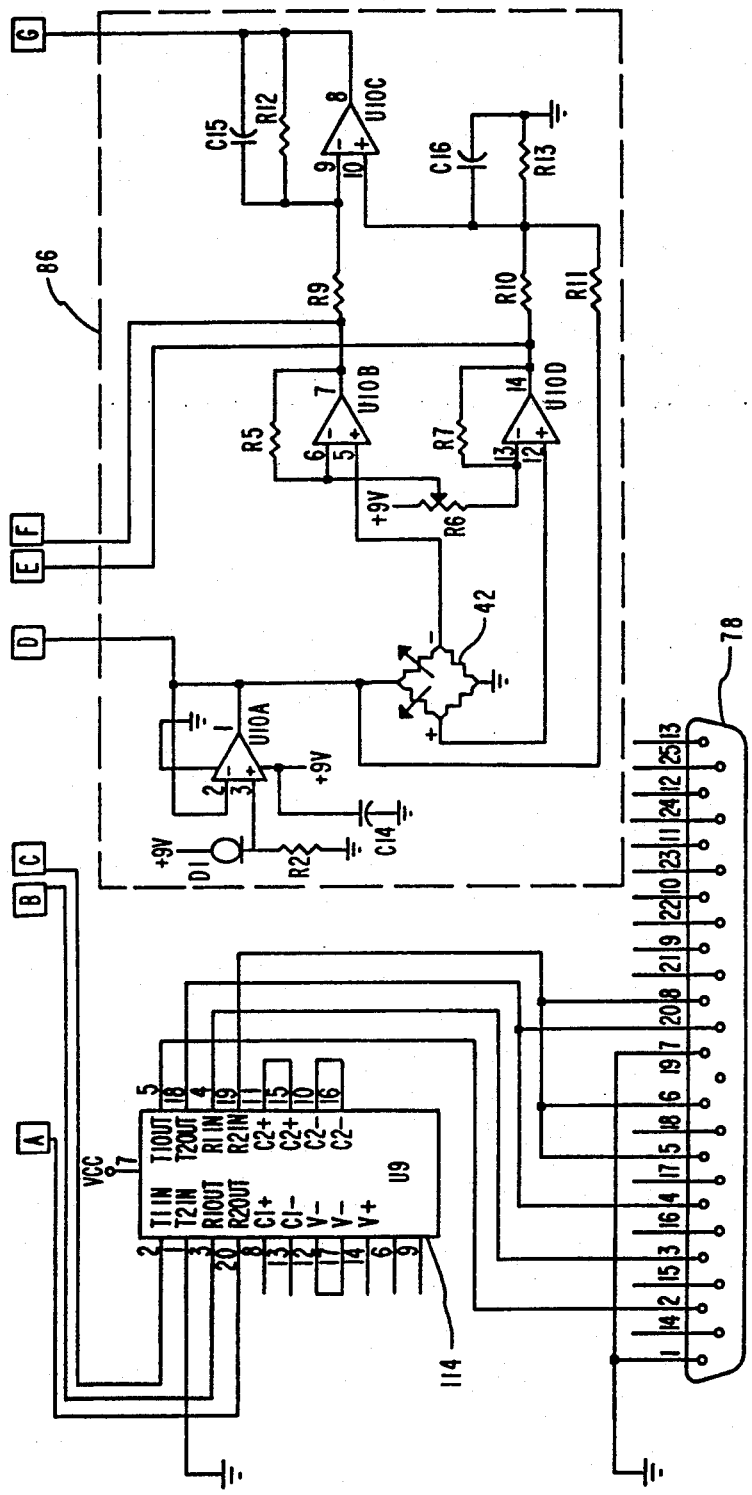
Figure 5B:
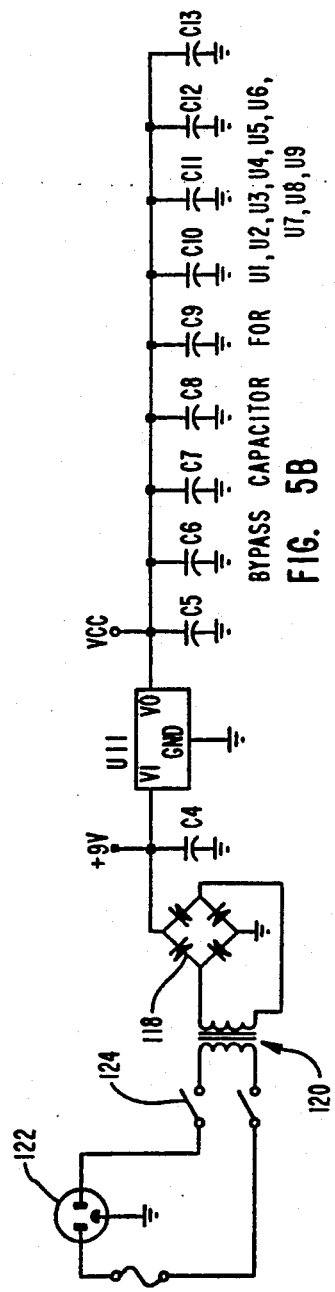
Figure 9A:
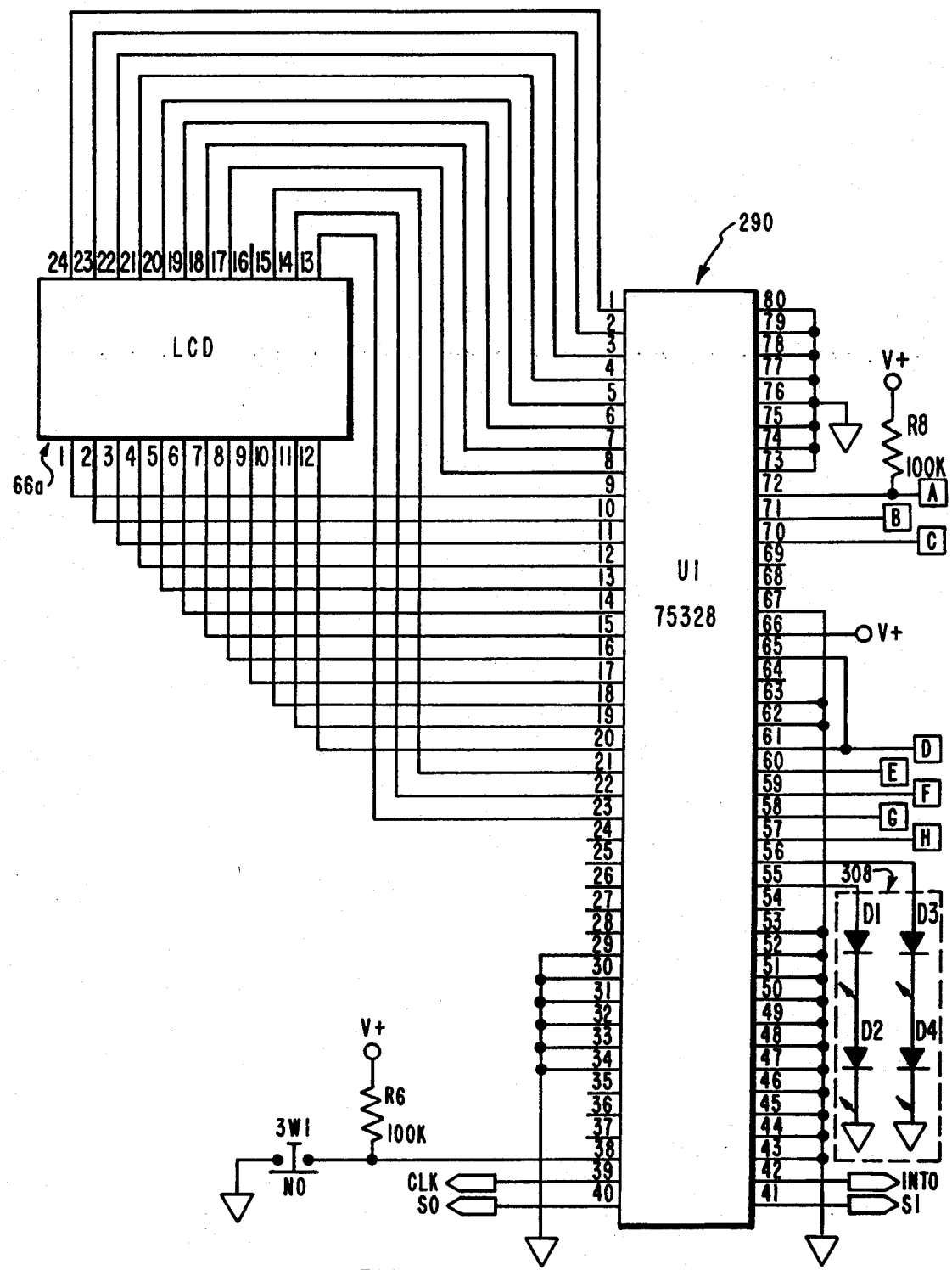
FIGS. 9A and 9B taken together constitute a detailed electrical schematic diagram which illustrate, as an example, the presently preferred embodiment and presently understood best mode for implementing the electronic circuit means of the syringe system of FIG. 7.
Figure 9B:
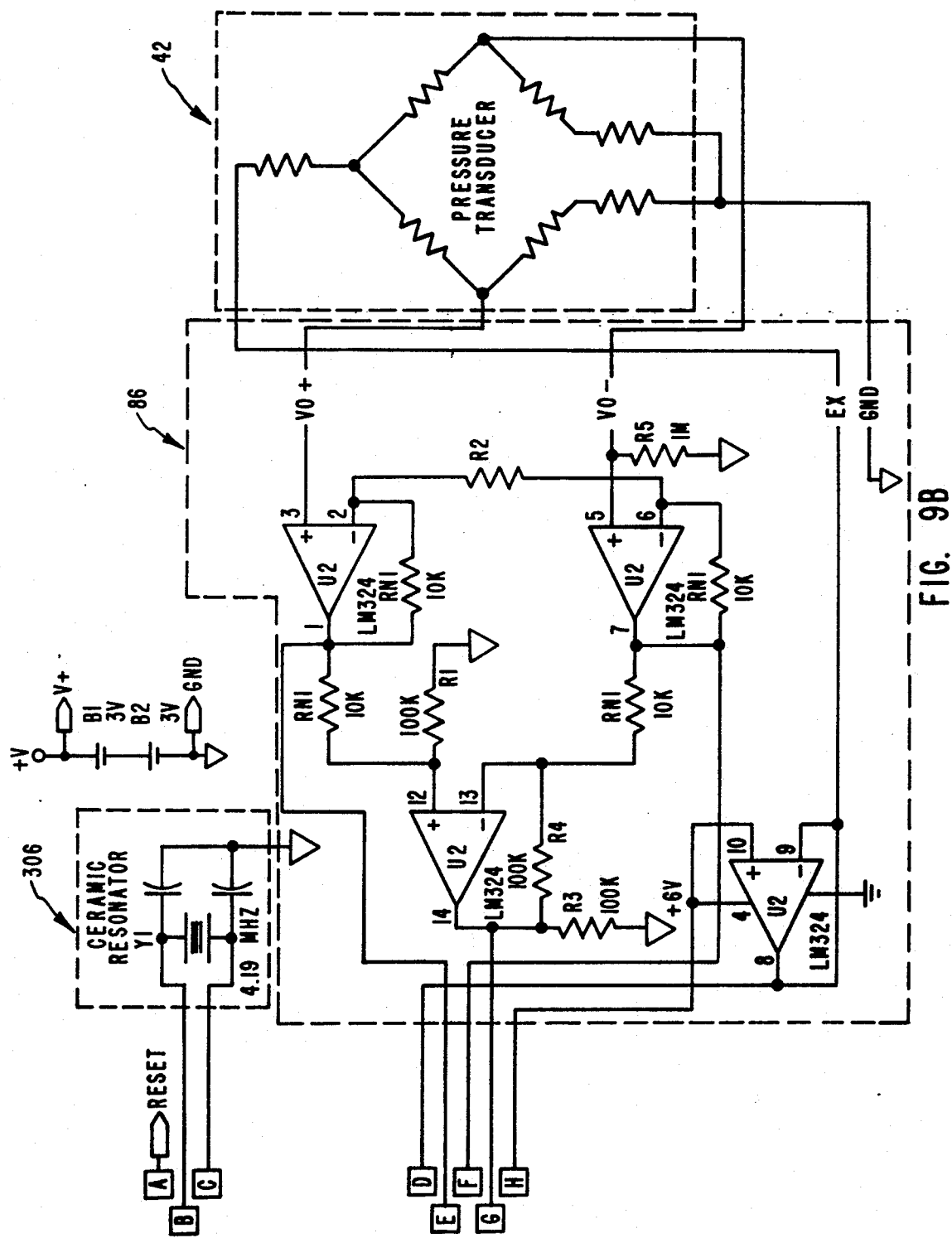

In FIG. 3, the transducer is shown as preferably comprising a piezoresistive semiconductor integrated circuit 42 which provides a Wheatstone bridge, as shown in the detailed electrical schematics at FIGS. 5B and 9B at the corresponding reference numeral. Transducer 42 is in turn attached to a small ceramic substrate 44 which contains additional circuitry for providing temperature compensation and calibration of the transducer 42, and to which is connected the electrical cable 46. The end of electrical cable 46, ceramic substrate 44 and piezoresistive semiconductor transducer 42 are assembled as illustrated in FIG. 3 and placed within housing 40, and then secured by a suitable potting compound and permanently enclosed by means of the cap 48 placed on top of the housing 40. In this manner, the entire transducer assembly is formed as an integral attachment to the syringe barrel 22. Stops 26 (see FIG. 1) are formed on the syringe plunger 24 so as to prevent the bulb 25 of syringe plunger 24 from being inserted to the point where it would otherwise close off the circular opening 50.

The small circular opening 50 may be filled, for example, with a silicone gel which will permit transmission of the fluid pressures exerted by means of syringe 16 through the circular opening 50 so that such pressures can be sensed by transducer 42, while at the same time isolating the integrated circuit 42 and substrate 44 from coming into contact with fluid contained in the syringe barrel 22.

In some prior art type inflation syringes, conventional strain gauges are mounted to the syringe barrel. These types of strain gauges typically include brass fittings which are in direct contact with the contrast media in the syringe. As a result, highly toxic substances, such as copper sulfate, have been found to be present in the contrast media as a result of chemical interaction of the brass fitting with the contrast media. While this is not harmful so long as the balloon is not ruptured, if a rupture does occur this toxic substance is released into the patient's cardiovascular system.

One advantage of the above-described syringe and transducer means is the elimination of materials, such as brass, from which such toxic substances are derived. Furthermore, contact of any sort between the contrast media and the transducer and related circuitry is completely prevented, as noted above, by the silicone gel that isolates such from the contrast media while still providing effective fluidic coupling to the transducer diaphragm.

While in the preferred embodiment the transducer means has been illustrated and described as a piezoresistive semiconductor which is integrally mounted to the syringe barrel 22, it should be appreciated that the preferred embodiment is illustrative only and is not to be construed as limiting the scope of the invention. For example, the semiconductor transducer could be located at the end of connecting tubing attached through a T-connector to tubing 38 and could therefore be located at a position remote from the syringe 16, as for example on an I.V. stand or mounted as part of the electronic circuitry contained inside of controller 20. Furthermore, the transducer means could also comprise transducer types other than the piezoresistive semiconductor type illustrated and described in the preferred embodiment, as for example conventional strain gauge transducers which have been known and used in the art for many kinds of different pressure monitoring applications, or fiberoptic transducers.

With further reference to FIG. 2, the electrical cable generally designated at 54 is comprised of two lengths as shown at 46 and 58. The first length 46 of cable 54 is permanently attached at one end to transducer 18 in the manner described above in connection with FIG. 3. The other end of length 46 terminates in a conventional connector 60 which attaches to the second length 58 of cable 54. The second length 58 of cable 54 in turn attaches by a conventional connector 62 to the electronic circuitry contained in controller 20. Advantageously, by providing a point at connector 60 which is intermediate the transducer 18 and controller 20, transducer 18 and syringe 16 can be disconnected from the controller 20 so that the syringe 16 can be conveniently moved to a different location for testing or the like while still maintaining the sterility of syringe 16 and transducer 18. Thus, while the controller 20 may not necessarily be sterile, sterility of the first length of cable 46 and the transducer 18 and syringe 16 can be maintained at all times.

With continued reference to FIG. 2, the electronic circuit means and display means of the system of the present invention are illustrated in the preferred embodiment as comprising part of controller 20. The specific electronic circuitry which is used for purposes of processing the electrical signals output by transducer 18 through cable 54 is contained inside of controller 20 and is more particularly illustrated in FIGS. 4 and 5A-5B, as hereinafter more fully described. The display means of the system is shown in the illustrated embodiment as comprising, in addition to corresponding parts of the electronic circuitry, a digital readout as generally designated at 66 which is part of the control panel 64.

Specifically, control panel 64 comprises a menu switch 74 which, when activated, will cause a series of optionally selectable functions to be displayed at the digital readout 66. Select switch 76 of control panel 64 can then be used to input various control parameters as well as causing the controller 20 to retrieve and display previously recorded data, as hereinafter more fully described. Controller 20 is also equipped with a conventional connector 78 for a printer cable 80 so that data which is recorded by controller 20 can also be selectively printed out for permanent documentation and later reference.

The digital readout 66 of control panel 64 is shown in the illustrated embodiment as comprising a conventional LED or LCD alphanumeric display having twelve or any other suitable number of controllable display positions for outputting numbers or letters. The display 66 is preferably also divided into a display portion 68 ("NUMBER") which displays and records the number of each discrete inflation of the balloon catheter. A second display portion as illustrated at 70 ("TIME") is used for purposes of checking and/or inputting the current date and time, as well as inputting control data with respect to a maximum duration for applied positive pressure, as desired, and is also used for purposes of displaying the duration of the inflation and signalling a system user if a selected time of duration has been reached. Display portion 72 ("PRESSURE") is similarly used for purposes of inputting selected control data with respect to a maximum positive inflation pressure desired in connection with any inflation, and also selection of the pressure units (e.g., either atmospheres or pounds per square inch), and is also used to display the current inflation pressure and to signal the user if a selected maximum inflation pressure has been reached.

Controller 20 can be conveniently located on a stand 82 at a point which is easily visible by the cardiologist or clinician using the system and can be switched on or off using a conventional switch located on the controller 20. The controller 20 is also plugged into a conventional AC wall outlet from which the power is derived for purposes of running the controller 20, and is also provided with a battery-backed memory which provides an internal clock and timer, and which retains data after the controller 20 is switched off.

Figure 4:
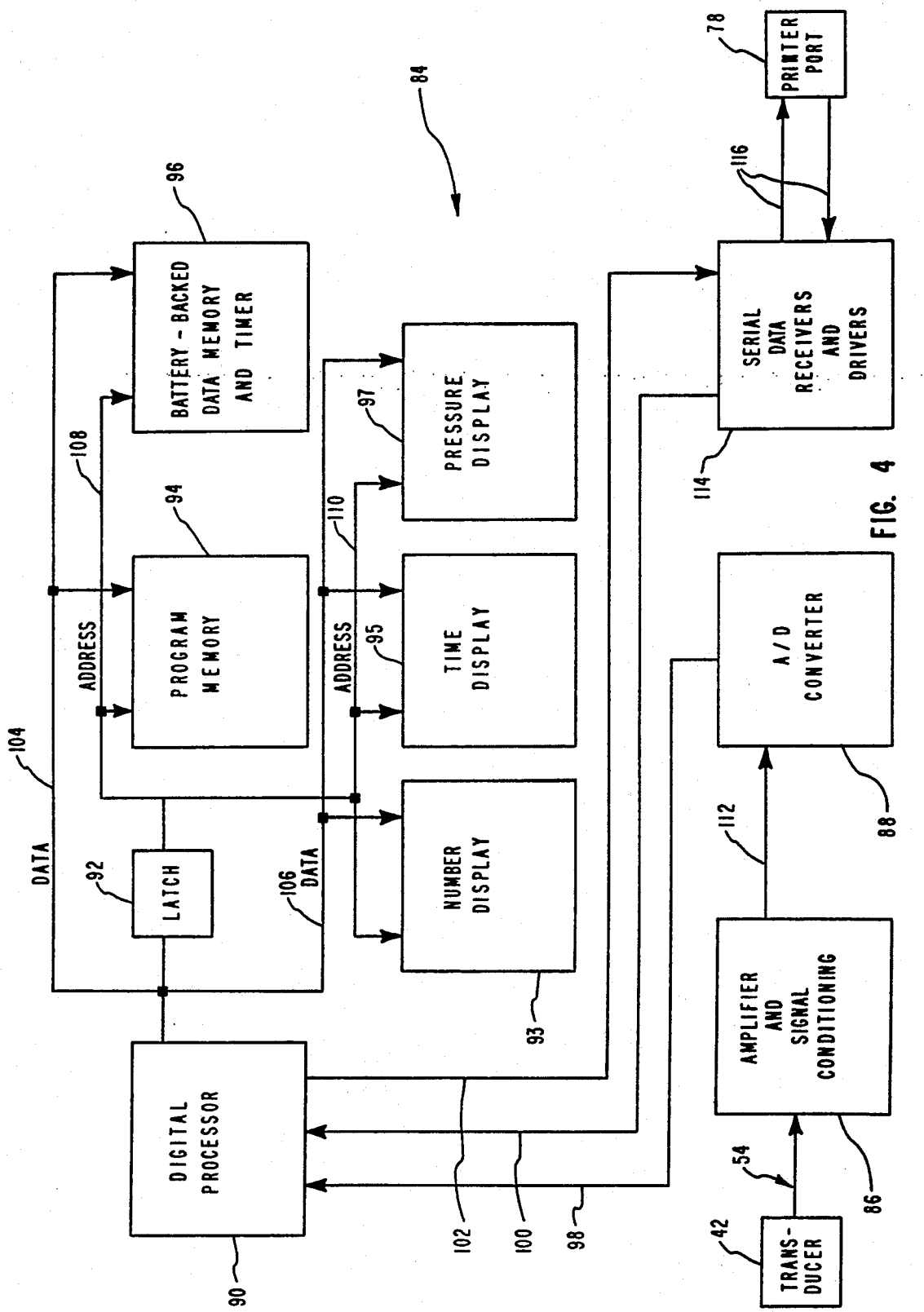
FIG. 4 is a functional block diagram which schematically illustrates the primary components of one presently preferred electronic circuit used in connection with the electronic controller.

With reference next to FIG. 4, the electronic circuit means of the system is more particularly illustrated. In the presently preferred embodiment, the electronic circuit means comprises, by way of example, means for amplifying the electrical signal output by the transducer means; means for converting the amplified signal from an analog to a digital form; digital processor means for processing the digital form of the signal so as to derive therefrom digital data from which the magnitude of the applied pressure, the length of time that pressure is applied to the balloon and whether the applied pressure corresponds to a first or a subsequent inflation of the balloon catheter may be output in a numerical form; data memory means for storing the digital data derived by the digital processor; and program memory means for storing machine-readable instructions utilized by the digital processor means to derive, store, retrieve and display digital data and to optionally display a series of functions for selection at the display means of various control parameters.

With particular reference to the presently preferred embodiment of the electronic circuit means as generally designated at 84 in FIG. 4, the transducer 42 is electrically connected by means of cable 54 to an analog circuit 86 which provides amplification and signal conditioning. As more particularly illustrated in FIG. 5B by the portion of the circuit enclosed by the dashed box 86, the amplifier and signal conditioning circuit 86 is shown in the preferred embodiment as a 100 millivolt full scale differential amplifier with an adjustable differential gain of forty to one, which is provided by amplifiers U10B, U10D, and U10C.

From circuit 86 the amplified signal is then input as schematically represented at line 112 in FIG. 4 and as illustrated at terminal H in FIG. 5B to a conventional analog to digital (A/D) converter circuit 88. The A/D converter 88 serves as a means for converting the amplified signal from an analog to a digital form by outputting a series of corresponding digital signals which identify the analog signal sensed and input by the transducer 42. As shown in reference to FIG. 5A, in the presently preferred embodiment the A/D converter 88 is comprised of an integrated circuit U8. The particular integrated circuit U8 used in the implementation of the electronic circuit means, as well as the identification of each of the parts used in the detailed electrical schematic of FIGS. 5A and 5B, is set forth in Table I at the end of the detailed description. It should be appreciated that the particular circuit components and circuit design which is illustrated in FIGS. 5A and 5B are intended merely as an example of the presently preferred embodiment and the presently understood best mode of implementing the overall functions which are represented by the block diagram of FIG. 4. FIGS. 5A and 5B illustrate in detail the electrical schematic diagram showing the pin numbers and interconnections for each of the integrated circuit components and the other circuit elements used in the implementation of the preferred embodiment. Of course other circuit designs can be devised that would also work satisfactorily using either software driven digital processing circuitry or hardware based circuit design.

With continued reference to FIGS. 4 and 5A-5B, the digitized signal is output by A/D converter 88 as schematically represented by line 98 and as illustrated in greater detail in FIG. 5A to a digital processor means 90. Digital processor means 90 is illustrated in FIG. 5A as integrated circuit U1. The digital processor is controlled by machine-readable instructions stored in program memory 94 which are communicated as schematically illustrated in FIG. 4 by means of a data bus 104 running between digital processor 90 and program memory 94. The particular program instructions carried out by the digital processor U1 are more particularly illustrated and described in reference to the flow chart of FIGS. 6A-6D, as hereinafter more fully described in part two, and are addressed by processor U1 through latch circuit 92 and an address bus schematically represented at line 108 (FIG. 4).

Briefly summarized, the instructions stored in program memory 94 are utilized by digital processor means 90 to derive from the digitized data the fluid pressures applied by the syringe 16 to the balloon catheter and to display the sensed pressures at the digital PRESSURE readout 72 of control panel 64 (see FIG. 2). The applied fluid pressures are also automatically recorded by digital processor means 90 and stored in the data memory 96. The output of the digital data to the display 72 is transmitted by way of bus 106 schematically shown in FIG. 4 and the corresponding electronic circuitry 97 (FIGS. 4 and 5A) which is used to drive the display 72. The processor means 90 can also be programmed to display the positive inflation pressure which is output at the LED display 72 in units of either atmospheres or pounds per square inch as selected by the system user by means of using the menu and select switches 74 and 76, as hereinafter more fully explained.

Processor means 90 can also be utilized according to the programmed instructions contained in memory 94 to monitor and thus assist in the control of the maximum positive inflation pressure to be applied to the balloon catheter by inputting at the PRESSURE readout 72 a maximum positive pressure using the menu and select switches. This control parameter is input from the corresponding display circuitry 97 on bus 106 and bus 104 to the data memory 96. Thereafter, once the maximum positive inflation pressure is reached, the digital processor will cause the PRESSURE display 72 to flash thereby signalling the system user that the maximum positive inflation pressure has been reached. This advantageously assists the system user in more carefully controlling and identifying the procedure used with respect to each inflation event.

In a similar manner, a selected duration for which positive inflation pressure is to be applied to the balloon catheter can also be input at TIME display 70 using the menu and select switches. The corresponding display circuitry 95 thus inputs the selected duration time through data buses 106 and 104 to data memory 96. Accordingly, the programmed instructions contained in memory 94 will thereafter cause the processor means 90 to begin counting the duration once positive inflation pressure begins to be applied. The count will be output by processor 90 at the TIME display readout 70 which will flash once the selected duration has been reached, thereby signalling the system user that positive inflation pressure has been applied for the desired length of time. Again, this significantly enhances the ability of the overall system to carefully assist in controlling the inflation procedures according to the selected parameters.

Data memory 96 is battery-backed so as to retain all data stored therein even when controller 20 is switched off, and so as to provide an internal timer for the date and time data and for clocking any selected maximum duration times input as described above.

Each of the control parameters which are input at the TIME and PRESSURE displays are input and stored as noted above in the data memory 96. In this manner, the appropriate control parameters are utilized by the program stored in memory 94 and are also automatically recorded in the data memory 96 for later reference. In a similar manner, once a positive inflation pressure is applied the processor means 90 will automatically time the duration of the positive pressures and this information will likewise be recorded and stored in the data memory 96 for later reference, along with a numerical identification input from the NUMBER display 68 which identifies whether the particular inflation event is the first time the balloon catheter has been inflated or whether the inflation is a subsequent inflation. In this manner, each time the balloon catheter is inflated it is discretely identified and the maximum inflation pressure and time duration data corresponding to that inflation event are not only displayed but are also automatically recorded and stored in the data memory 96.

A latch circuit 92 is used to control the gating of address data from digital processor 90 to the respective memories 94 and 96 and display circuits 93, 95 and 97 as is conventional in the art. In the detailed schematic of FIG. 5A, the latch circuit 92 is illustrated at integrated circuit U2, while the program memory and data memory circuits 94 and 96 are shown as the integrated circuits U3 and U4, the particular specifications of which are identified in Table I. Integrated circuits for the number, time and pressure display circuits 93, 95 and 97 are also shown in FIG. 5A at integrated circuits U5, U6 and U7 with their corresponding identifications in Table I.

In addition to the digital readout 66 the system of the present invention also provides for output of the recorded data from processor means 90 through serial data lines 100, 102 to a serial data receiver and driver circuit 114, which in turn is connected as schematically illustrated at lines 116 to a printer port 78 to which printer cable 80 is connected. The serial data receivers and drivers are shown as a conventional integrated circuit identified at U9 in FIG. 5B, and which is an RS232 driver and serial transmitter.

The supply voltage used for driving the integrated circuits and other active circuit elements shown in the detailed schematic diagram of FIGS. 5A and 5B is supplied by means of a transformer 120 which is connected at its output to a full wave bridge rectifier 118. The output of rectifier 118 is regulated by integrated circuit U11 which is a voltage regulator. The capacitors C5-C13 serve as noise suppression filters for each of the integrated circuits U1 through U9. With further reference to FIG. 5B, the switch 124 represents the switch on the back of the controller 20 which is used to turn the controller on and off and which connects the controller through a conventional cord and socket plug 122 to an AC outlet.

2. FIGS. 7-9

Figure 7:
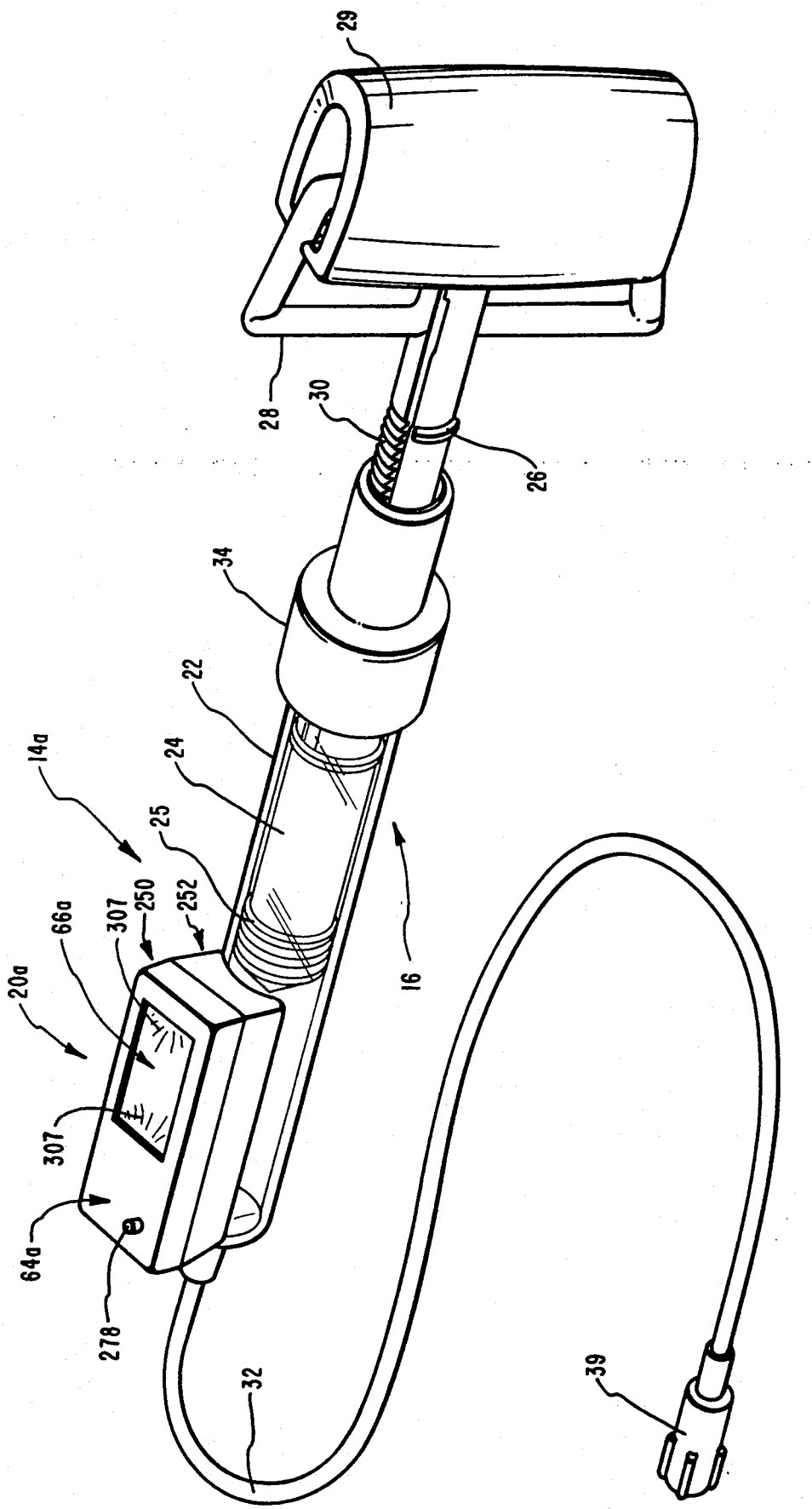
FIG. 7 is a perspective illustration showing a second embodiment of the system of the present invention in which a transducer means together with an electronic controller are all mounted directly onto the syringe barrel so as to form a totally self-contained, disposable syringe system.

FIG. 7 illustrates an alternative embodiment of the syringe system of the present invention. In the embodiment of FIG. 7, the electronic circuit means and display means of the system of the present invention are designed so as to comprise part of a controller which is generally designated at 20a that is battery powered and is mounted directly onto the syringe 16 so as to form a totally self-contained, disposable syringe system 14a. Thus, as generally illustrated in FIG. 7, controller 20a comprises an upper housing assembly which is generally designated at 250 and a lower housing assembly which is generally designated at 252 which are joined together and which are mounted directly onto the end of the syringe barrel 22. The control panel generally designated at 64a is provided with only a single control switch 278, as hereinafter more fully described, which is used to turn the controller 20a on, and which is also used to recall and display maximum inflation pressure and the duration of inflation for the last inflation event.

Figure 8:
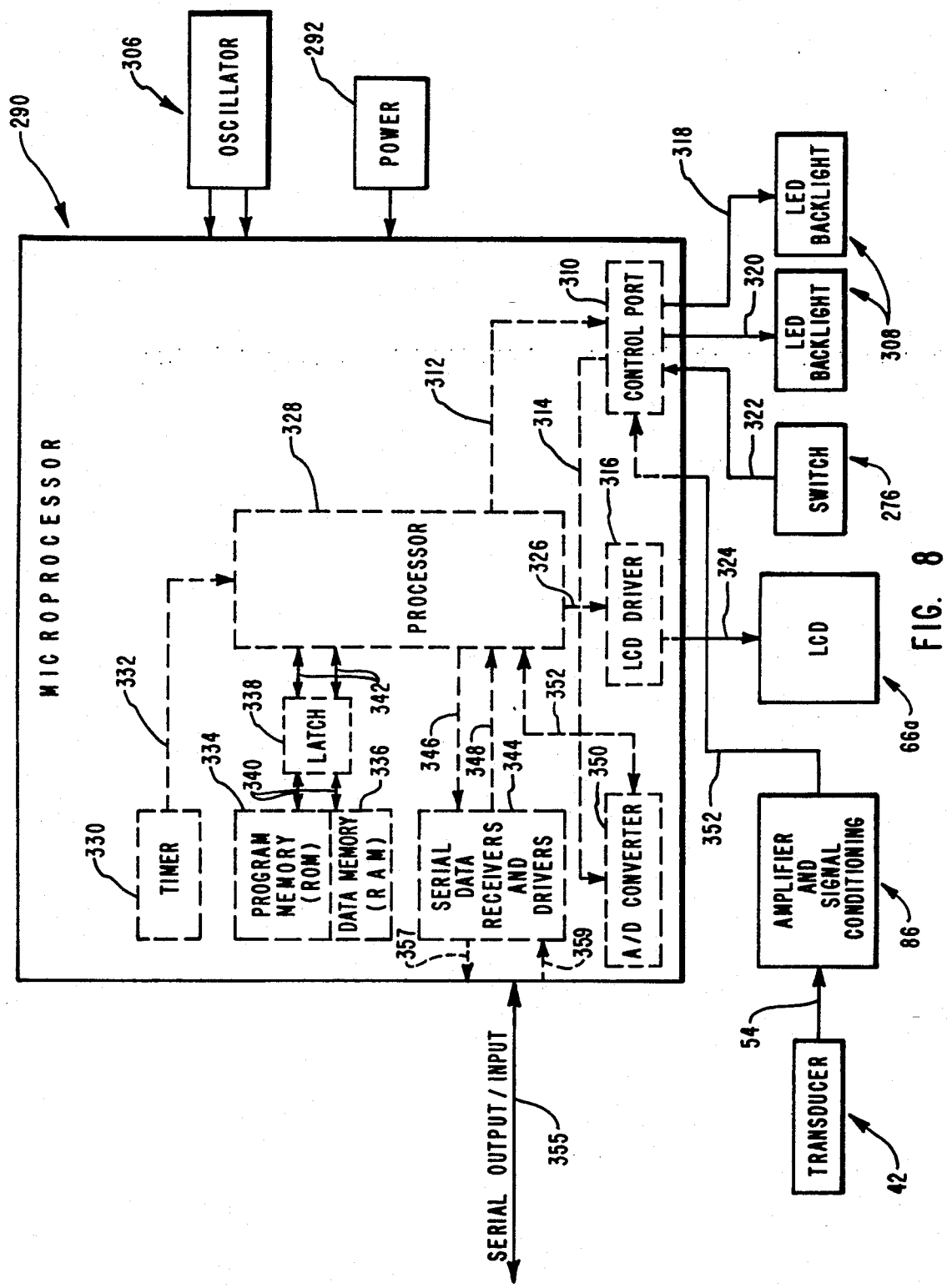
FIG. 8 is a functional block diagram which schematically illustrates the primary components of the digitally controlled electronic circuit used in connection with the syringe system of FIG. 7.

The syringe generally designated at 16 is essentially identical in all respects to the syringe 16 described above in connection with FIGS. 2 and 3 and therefore will not be described in further detail in regard to the embodiment which is illustrated in FIGS. 7-9.

Figure 7B:
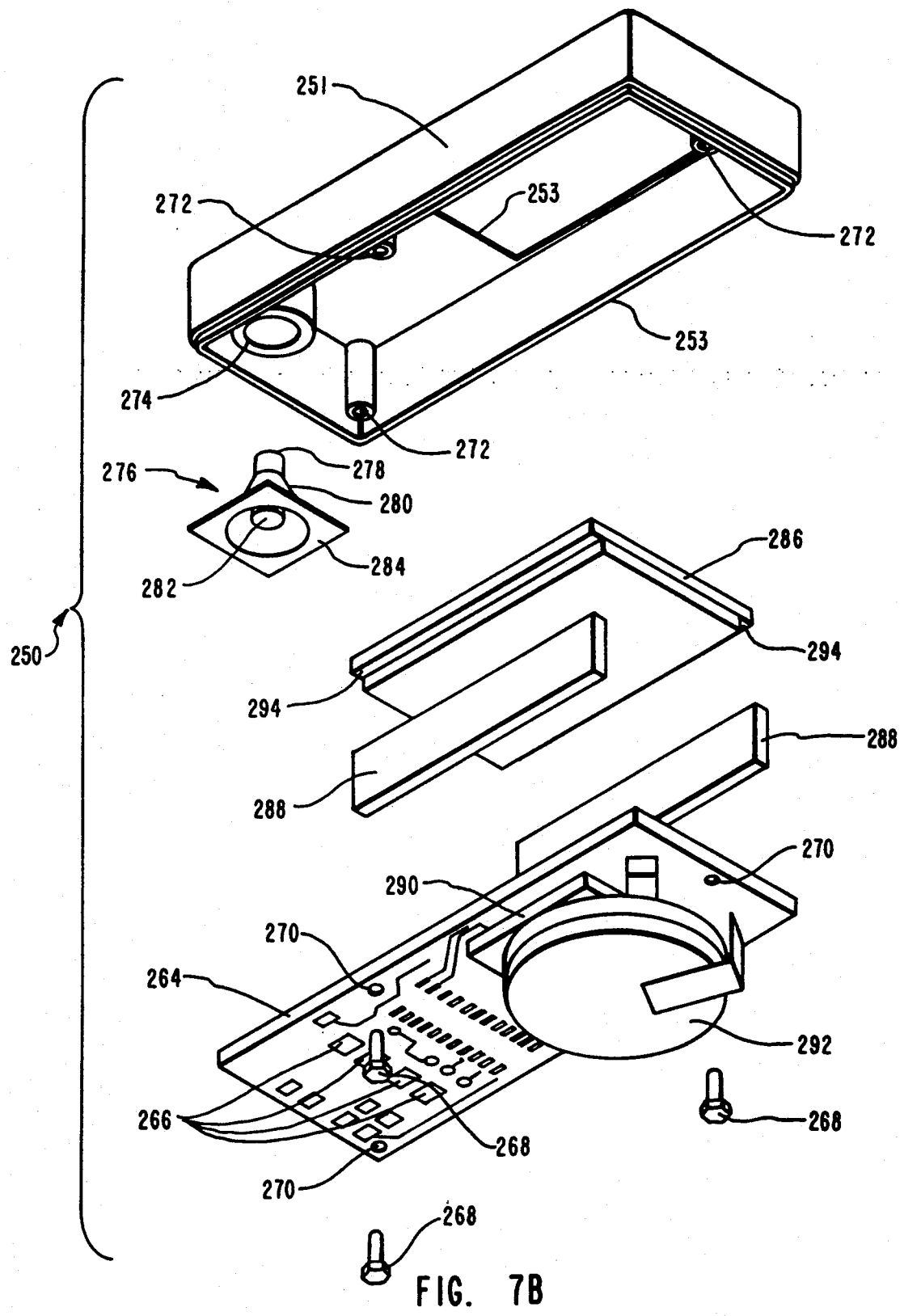
FIG. 7B is an exploded perspective illustration which shows in greater detail some of the primary components and assembly constituting the electronic controller for the embodiment of the syringe system illustrated in FIG. 7.

The manner in which the controller 20a is constructed and mounted to the syringe barrel 22 is more particularly illustrated in reference to FIGS. 7A and 7B, taken together. As shown in FIG. 7A, the lower housing assembly generally designated at 252 is preferably formed as a single molded plastic part. The lower housing assembly 252 is formed with a generally square shaped box portion 254 which is designed to dimentionally fit over the correspondingly shaped transducer housing 40 which is molded as part of the syringe barrel 22.

As in the case of the embodiment described in FIGS. 2 and 3, the integrated circuit which includes the transducer 42 is mounted directly onto a ceramic substrate 44 and is electrically connected to conductive pads 262. A rectangular opening 256 is provided in the square shaped member 254 which fits over the correspondingly shaped transducer housing 40. The rectangular opening 256 in turn is intended to receive a conductive elastomeric or rubber member 260 such that when the member 260 is seated within the rectangular opening 256, the bottom of member 260 will contact the conductive pads 262. The conductive rubber member 260 will then also contact and provide electrical interconnection between the conductive pads 262 and corresponding conductive pads 266 (see FIG. 7B) which are provided on one side of a printed circuit board 264. Printed circuit board 264 contains the microprocessor 290 and a battery 292 which are used to provide power to the electronic circuit components of the controller 20a. The conductive rubber member 260 is a material that is known in the art and is sometimes referred to as a "zebra" or "Z" strip. Accordingly, the conductive rubber Z strip 260 serves as a means for providing an electrical interconnection between ceramic substrate 44 onto which the transducer circuit 42 is mounted and the other electronic components of the controller 20a which are carried on the printed circuit board 264.

With further reference to FIG. 7A, the upper housing assembly 250 of controller 20a carries the printed circuit board 264 onto which is mounted, as noted above, a microprocessor circuit 290, a battery 292, a digital readout such as LCD 294 as well as other electronic components which are required for the circuitry of the controller 20a, as illustrated and described in more detail in connection with FIGS. 9A and 9B.

The upper housing assembly 250 is provided with a rim 253 that extends around its entire periphery (see FIG. 7B) and which is designed to fit into a corresponding channel 255 which is formed around the periphery of the lower housing assembly 252. The two housing assemblies 250 and 252 can be firmly bonded together and the entire controller assembly 20a is then permanently mounted and bonded onto the syringe barrel 22. For this purpose, the lower housing assembly 252 is provided with a corresponding cylindrical shape 258 on its underside so that the lower housing assembly 252 conforms to the cylindrical shape of the syringe barrel 22.

With particular reference to FIG. 7B, the components which are carried by the upper housing assembly 250 are shown in greater detail. The upper housing assembly 250 comprises a generally rectangular shaped molded piece 251 which has a transparent window 253 formed in the upper surface through which the LCD 294 may be viewed. Preferably, except for window 253 the upper and lower housing assemblies 250 and 252 are molded from opaque plastic material.

A resilient control switch generally designated at 276 is comprised, for example, of an elastomeric button switch. The control switch 276 has an upper cylindrical extension 278 that extends through an opening in well 274 which is formed in the upper rectangular member 251 so that the cylindrical portion 278 can be finger-actuated by pressing. The switch 276 also is comprised of an integral conically shaped skirt 280 which terminates in a generally square shaped base 284. Base 284 entirely covers the base of well 274 so that when the entire assembly is completed, the switch 276 is fluid tight and will thus not permit water, saline solution or other liquids to enter the controller through the location of the actuable button 278. Accordingly, the base 278 extends downwardly and rests again the upper side of the printed circuit board 264 so that the actuable button 278 is held in a position which extends through the opening of well 274 into the position as shown in FIG. 7A but at the same time the base 284 also seals the well 274. When the button 278 is pushed downwardly, the circular base 282 of the button switch is pushed into contact with a conductive pad (not shown) on the upper side of the printed circuit board 264 thereby making the necessary electrical contact to activate the electronic components, as hereinafter more fully described. The elastomeric properties of conical skirt 280 will return the button 278 upwardly when it is released.

With continued reference to FIG. 7B, the microprocessor circuit 290 is mounted to the underside of printed circuit board 264 and a battery 292 is mounted over the microprocessor 290 on the same side of the printed circuit board 264. The upper side of printed circuit board 264 carries conductive pads (not shown) which are electrically connected to the LCD 286 by means of conductive rubber Z strips 288 which both vertically support the LCD 286 so that it is held into engagement with the upper portion 251 of the controller housing. Channels 294 are adapted to receive the upper edge of the conductive rubber Z strips 288 to provide electrical contact at LCD 286.

In the preferred assembly of the upper housing assembly 250, the elastomeric button switch 276 is placed into the well 274, the LCD 286 is positioned over the transparent window opening 253, the elongated conductive rubber Z strips 288 are positioned at the side edges of LCD 286 in the corresponding longitudinal recesses 294, and then the printed circuit board 264 is placed over the top of all of those components. Pins or anchors 268 are then inserted through corresponding holes 270 in the printed circuit board and into corresponding receiving holes 272 in the upper portion 251 of the housing. The pins 268 are bonded or otherwise anchored into the holes 272 such as by a press fit or other appropriate means.

The nature of the information displayed on the digital readout 66a is best illustrated in FIG. 7C. As schematically illustrated in that drawing figure, the syringe system 14a is designed to digitally display the maximum inflation pressure, as illustrated at 296, as well as the duration of the inflation as illustrated at 298. Three annunciators are also designed to be displayed. Reference numeral 300 identifies a "LAST INFLATION" annunciator. This annunciator is displayed each time the button 278 is pushed, at which time the maximum inflation pressure 296 and the inflation duration 298 are displayed in connection with the last inflation event.

As hereinafter more fully described in connection with the electronic components, this information is stored in a single register and recalled when the button 278 is pressed, if the system is at zero or negative pressure. For each inflation event (e.g. once pressure increases beyond one-half atmosphere), the inflation pressure 286 and the duration of inflation 298 are displayed as real time parameters which will be continuously incremented during the inflation event while the inflation pressure is being increased. Once the user releases the inflation pressure so that the pressure drops below near zero, the inflation event is determined to be completed, and the maximum pressure and duration for that event can then be recalled and displayed by pressing button 278.

Two additional annunciators as identified at reference numerals 302 and 304 are also designed to be selectively displayed. These annunciators identify, respectively, maximum and minimum pressure values which are programmed into the system. For example, typically minimum pressures which are programmed into the controller would be on the order of −0.4 atmospheres whereas maximum inflation pressures which would typically be programmed would be on the order of 20 to 25 atmospheres in the case of an angioplasty control system. These values could of course be varied depending upon the particular application for the syringe system.

The electronic circuit means of controller 20a are illustrated in further detail in reference to the functional block diagram of FIG. 8, and the accompanying electrical schematic diagram of FIGS. 9A and 9B, which together illustrate one presently preferred implementation of the block diagram of FIG. 8 in its presently understood best mode.

With reference to FIGS. 8 through 9B taken together, the electronic circuit means comprises, by way of example, means for amplifying the electrical signal output by the transducer means; means for converting the amplified signal from an analog to a digital form; digital processor means for processing the digital form of the signal so as to derive therefrom digital data representing the magnitude of the applied pressure and the length of time that the pressure is applied to the balloon of the catheter; data memory means for storing the digital data derived by the digital processor; and program memory means for storing machine-readable instructions utilized by the digital processor means to derive, store, retrieve and display the digital data.

With particular reference to FIG. 8, the transducer 42 in connection with the embodiment of FIGS. 2–5. Transducer 42 is electrically connected as schematically shown at 54 (by means of the conductive rubber Z strip 260 described above) to the circuit components which serve as the amplifier and signal conditioning circuitry as generally designated at 86 in FIG. 8, and also as identified by those circuit components which are enclosed within the dashed box identified by the reference numeral 86 in FIG. 9B. The amplifier and signal conditioning circuit 86 as shown in FIGS. 8 and 9B is once again essentially identical to the corresponding circuit 86 as described above in connection with FIGS. 4-5.

From the amplifier and signal conditioning circuit 86 the amplified analog signal is then input as schematically represented at line 352 to a control port 310 which is internal to the microprocessor's integrated circuitry. From control port 310 the signal is input as schematically indicated at line 314 to an analog to digital (A/D) convertor 350 which is also internal to the microprocessor's integrated circuitry. The A/D convertor 350 serves as a means for converting the amplified signal from the analog to a digital form.

The particular integrated circuit which is used for microprocessor 290 is identified in FIG. 9A as integrated circuit U1 and is also further identified in Table II at the end of the detailed description. It should be appreciated that the particular circuit components and circuit design as illustrated in FIGS. 9A and 9B and as also identified in Table II are intended merely as an example of the presently preferred embodiment and the presently understood best mode of implementing the overall functions which are represented by the block diagram of FIG. 8. FIGS. 9A and 9B illustrate in detail an electrical schematic diagram showing the pin numbers and interconnections for each of the integrated circuit components and the other circuit elements used in the implementation of the block diagram of FIG. 8. Of course other circuit designs could be devised that would work satisfactorily, using either software-based digital processing circuitry or hardware-based circuit designs.

With continued reference to FIGS. 8, 9A and 9B, the digitized signal is input as schematically indicated at line 352 to the digital processor 328. The digital processor 328 is controlled by the programmed instructions stored in program memory (ROM) 344 and which are communicated as schematically illustrated at lines 340 through a latch 328 to the digital processor 328. The particular program instructions carried out by the digital processor 328 are more particularly illustrated and described in reference to the flow chart of FIG. 10, as hereinafter more fully described. The program instructions are addressed by the digital processor 328, as schematically represented by the lines 340 through latch 338.

Briefly summarized, the instructions stored in program memory 334 are utilized by the digital processor 328 to derive from the digitized transducer signal the applied inflation pressure which is being exerted by the syringe 16 on the balloon of the catheter and to display the sensed pressure at the digital pressure readout 66a of controller 20a. As noted above, this is designed to occur in real time as the pressures are being applied. At the same time, the inflation pressure is also timed until it reaches its maximum value and the pressure is then released by withdrawing the syringe plunger. If desired, the inflation pressure and the duration of the inflation pressure can be recalled and displayed for the last inflation event by pressing the button 278 on the controller 20a if the system is at zero or negative pressure.

The data memory means of the electronic circuit means is provided, in the embodiment of FIG. 8, by a scratch pad random access memory (RAM) 336 which is also accessed through latch 338 by digital processor 328. The digital data memory 336 is used to record and store the maximum inflation pressure and the duration of inflation which are recalled when the button 278 is activated.

A timer 330 also communicates as schematically indicated by line 332 with the digital processor 328, and is internal to the integrated circuitry contained on the microprocessor circuit 290. Serial data receivers and drivers 344 also communicate as schematically illustrated at lines 346 and 348 with the digital processor 328, and are internal to the integrated circuitry of the microprocessor 290. The serial data receivers and drivers 344 can be used for outputting a variety of data through a serial communication output/input line as schematically indicated at lines 355, 357 and 359.

An LCD driver 316, also internal to the circuitry of integrated microprocessor circuit 290, is used to control the LCD display 66a as schematically indicated at line 324. Additionally, LED backlights 308 are controlled through control port 310 as schematically indicated at lines 312, 318 and 320. The LED backlights 308 are positioned on opposite ends of the LCD display (see for example FIG. 7) so that the information which is digitally displayed on the LCD 66a is more clearly visible, by lighting the LCD at its opposite ends, as schematically shown at 307. This is particularly helpful in a partially darkened environment such as would typically be the case where an angioplasty procedure is being conducted.

Power for the microprocessor 290 and other circuit components is supplied by the batteries 292 which are also illustrated in connection with the upper housing assembly 250 of FIG. 7B. The batteries 292 advantageously permit elimination of any connecting cables or the like so that the syringe system 14a is totally self-contained and does not require outside connection to any other power source. This advantageously simplifies the overall system 14a and makes maintaining sterility of the syringe system 14a an easier task throughout the entire procedure, particularly if the patient is to be moved from one location to another.

Since the syringe system 14a is battery operated, conservation of the batteries is important. For example, it is not uncommon for an angioplasty procedure to be interrupted for several hours between inflation events while other procedures are performed. Accordingly, to conserve the batteries, the microprocessor 290 is programmed to go into a standby mode. Power to the LED backlights is turned off whenever the microprocessor 290 senses a zero pressure for an arbitrary length of time (as for example 15 minutes). If zero pressure is sensed for a further length of time (as for example 90 minutes), then the LCD is also turned off. Pushing the button 278 will restore the LCD reading and turn the LED backlights back on.

In reference to FIGS. 9A and 9B, the appropriate pin connections and the identification of each corresponding integrated circuit component is illustrated in detail in the schematic diagram of FIGS. 9A and 9B taken in conjunction with the part number identification information set forth in Table II at the end of the description.

II. The Method

Attention is next turned to a detailed description of the presently preferred methods by which the system of the present invention is used to monitor, display and automatically record inflation data, with particular reference to FIGS. 6A-6G and FIG. 10 which illustrate the presently preferred embodiments of the instructions which may be utilized to control the processor means 90 or 290, respectively. As will be appreciated by those of ordinary skill in the art, and as noted above, while the system and method as described in reference to the preferred embodiments herein illustrate the invention as implemented using state of the art digital processing design and corresponding program instructions, the system and method could also be implemented and carried out using a hardware design which accomplishes the necessary electronic processing, which is thus intended to be embraced within the scope of various of the claims as set forth hereinafter.

A. FIGS. 6A–6G

Figure 6A:
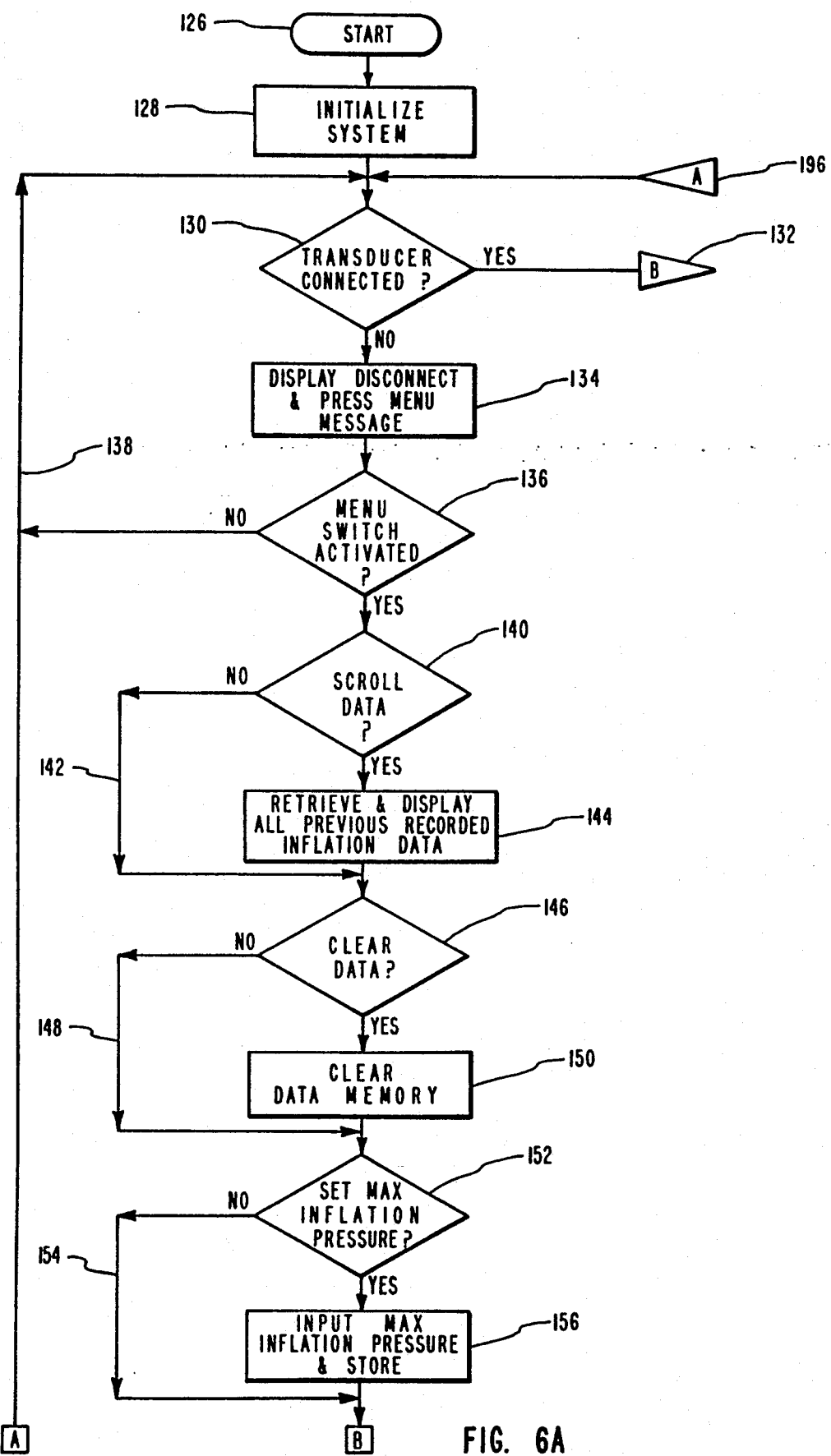
FIGS. 6A through 6D taken together illustrate a flow chart showing one presently preferred method for programming the digital processor of the electronic circuit means in accordance with the method of the present invention.
Figure 6B:
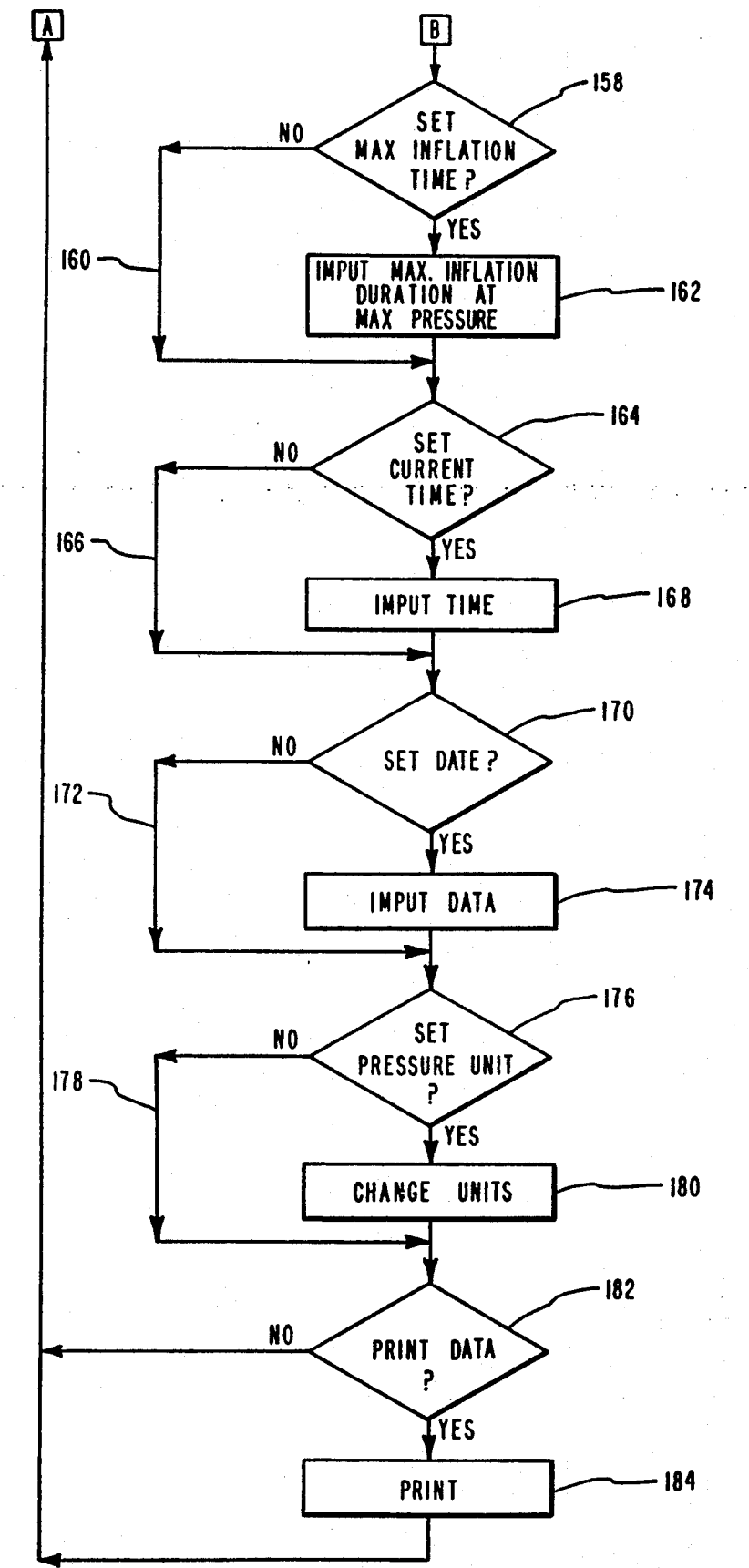

With reference to FIG. 6A, when the controller 20 is turned on the program starts as indicated at step 126 and then immediately moves to step 128 which causes the system to initialize. At this step, the appropriate program instructions are loaded into the digital processor. The system then moves to step 130 where it checks to determine whether the transducer 42 has been electrically connected by means of the cable 54 to the electronic circuitry housed in controller 20. If the transducer is connected the system then moves as indicated at flag 132 to the portion of the programmed instructions illustrated in FIG. 6C. If the transducer 42 has not yet been electrically connected to controller 20, the system causes a message to be output on the digital readout 66 signifying that the transducer is disconnected (e.g. "NO SYRINGE") and instructing the system user to press the menu switch 74, as shown at step 134. The system then moves to step 136 to check whether the menu switch 74 has been activated and if not returns to step 130 as schematically illustrated at 138 and continues in that loop until the menu switch 74 is activated.

Once the menu switch 74 is activated at step 136, the system then moves to step 140 and causes the readout 66 to display a message inquiring whether the data previously recorded by the system is to be scrolled (e.g., inflation pressure and duration corresponding to each inflation number is retrieved and displayed in sequence) at the digital readout 66. If the system user desires to review the previously recorded data, the select switch 76 is activated and the system then implements step 144 which causes all of the previously recorded inflation data for each inflation event to be retrieved in sequence and displayed. If at step 140 the system user does not wish to scroll the previously recorded inflation data, the menu switch 74 is again activated which causes the system to skip step 144 as schematically illustrated at line 142 so as to proceed with the next inquiry as represented at step 146.

At step 146 the system causes a message to be displayed on the digital readout 66 inquiring whether previously recorded inflation data which has been stored in the data memory 96 is to be cleared. If select switch 76 is activated this causes the processor to clear the previously recorded inflation data from data memory 96, as indicated at step 150. If the previously recorded inflation data is not to be cleared from data memory 96, the menu switch 74 is activated which causes the system to skip step 150 as illustrated at line 148 and to move to the next inquiry as represented at step 152.

At step 152 the system causes the digital readout 66 to display an inquiry with respect to whether an upper limit is to be set with respect to the maximum positive inflation pressure to be applied with respect to the next inflation event. If so, the select switch 76 is activated and is used to input the selected maximum positive inflation pressure through the data transfer buses 106 and 104 (see FIG. 4), to the data memory 96 for later reference. If a maximum inflation pressure is not selected at step 52, the menu switch is activated which causes the system to skip step 156 and move to the next inquiry as represented at step 158.

At step 158 the system displays a message at the digital readout 66 inquiring whether the maximum duration for application of positive pressure is to be selected. If so, the select switch is again activated which causes the system to move to step 162 and the select switch 76 is then used to input at the time display 70 the selected duration. This selected duration is input by means of the corresponding time display circuitry 95 (see FIG. 4) through the data transfer buses 106 and 104 to the data memory 96 for later reference.

In a manner similar to that described above in connection with the preceding inquiry steps, the system continues to inquire whether the current time and date are to be displayed, as represented at steps 164 and 170, respectively, and if so, by utilizing the select switch 76 as described above, current date and time may be entered at the time display 70. However, the internal clock that is part of the integrated circuit U4 will typically make it unnecessary to enter these parameters. The system then moves through the series of steps represented at 176, 180, 182, and 184 where it determines the pressure units to be displayed at the pressure display 72 as well as determining whether data is to be printed. After the print inquiry has been responded to by utilization of the appropriate menu or select switch 74 or 76, respectively, the system returns as illustrated at line 138 to step 130.

As will be appreciated from the foregoing, the portion of the program instructions which are carried out according to the flow chart of FIGS. 6 A and 6 B pertains to that part of the program which permits a series of optionally selectable functions to be sequentially displayed for purposes of inputting various control parameters which are later utilized in displaying and automatically recording the data, as well as utilizing these control parameters to alert the system user when selected limits are reached with respect to maximum positive inflation pressure and duration of positive inflation pressures.

Figure 6C:
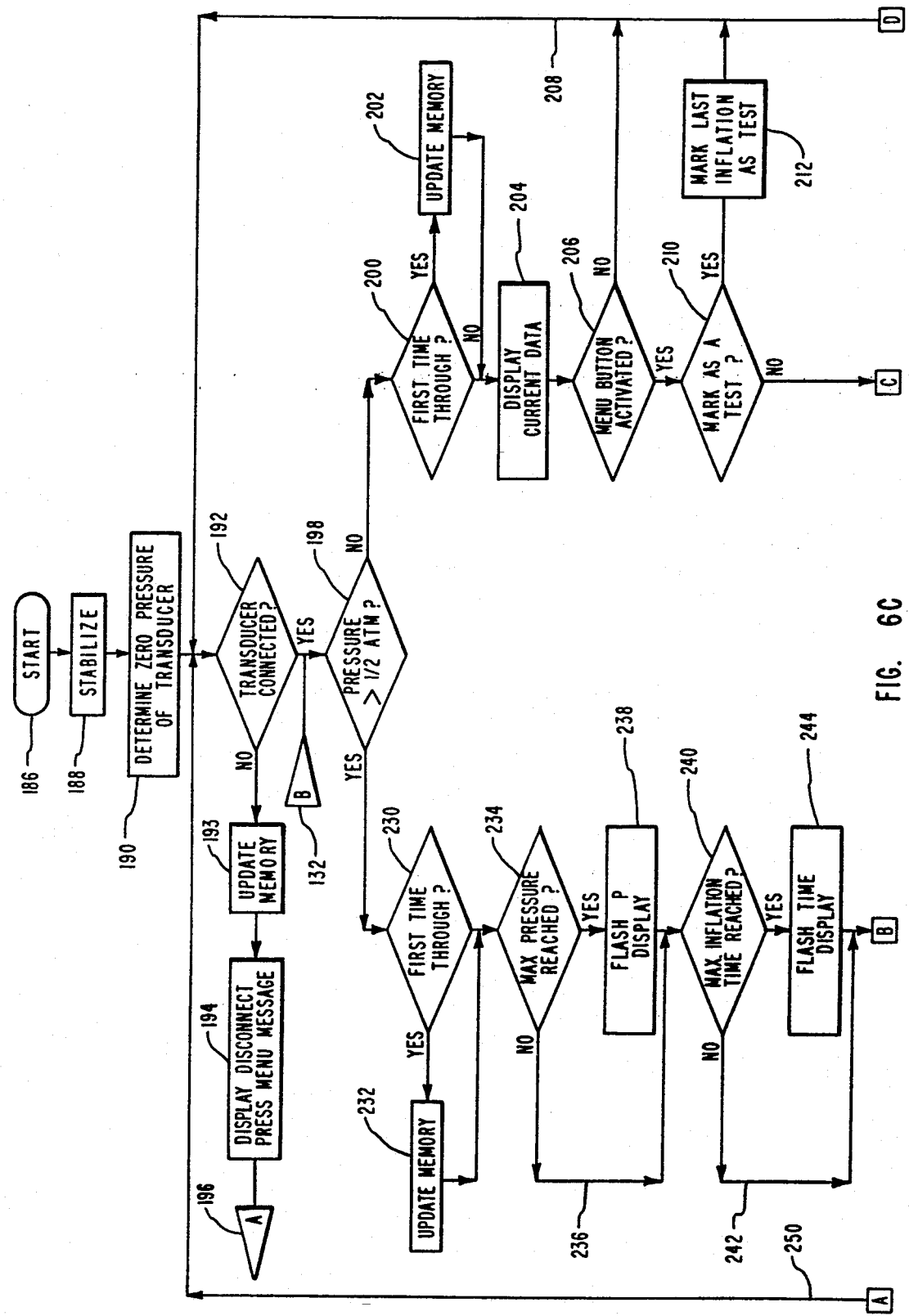
Figure 6D:
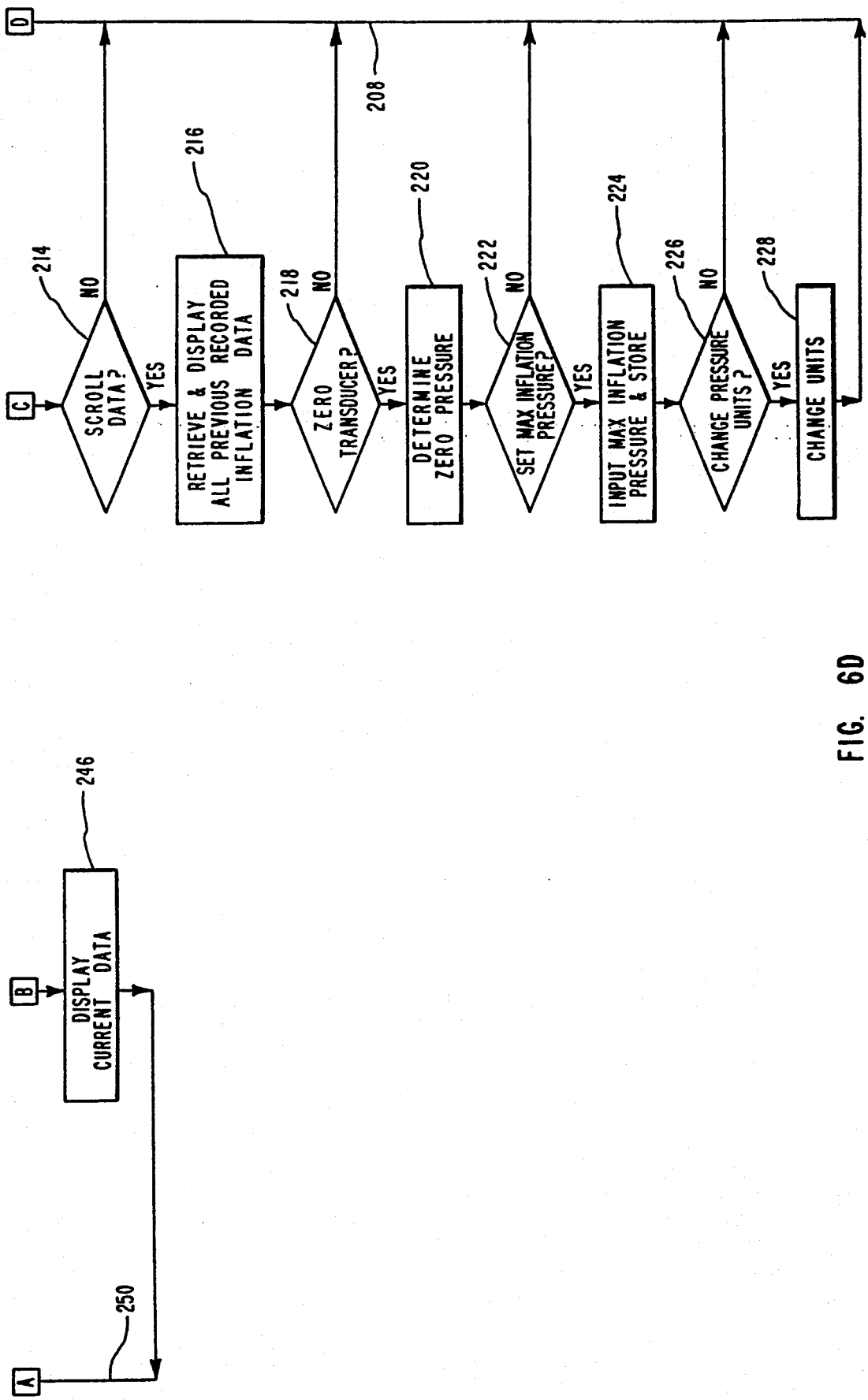

Once the transducer 42 has been connected to controller 20 the system moves to that portion of the program illustrated in FIGS. 6C and 6D where it then starts as schematically indicated at step 186 by moving to step 188 so that the electronic circuitry is permitted to stabilize. At this step the processor delays all operation of the electronic circuitry for a selected period of time to permit the circuit components to reach a steady state so that transient conditions will not introduce any errors into the data. The system then moves to step 190 where it determines the zero pressure of the transducer 42. At this step the processor means 90 determines the reading at transducer 42 with no pressure being applied. This zero pressure reading is then stored and is subsequently subtracted or offset against all other pressure readings to assure accuracy of the data.

At step 192 the system again undergoes a check to determine whether the transducer 42 is still connected to the controller 20. This is a safety precaution to make sure that at all times during the inflation procedure the transducer 42 is electrically connected to the controller 20 so that the data is being accurately input, displayed and recorded. If the transducer is not connected the system first updates the data memory 96 (step 193) so as to mark the time of disconnection and then a message is output as indicated at step 194 which notifies the system user that the transducer is disconnected and instructing the system user to press the menu switch 74. If the transducer 42 is still connected the system then moves to step 198 and begins to monitor the electrical signal from the transducer, which signal has been digitized and input to the digital processor as previously described in connection with FIGS. 4 and 5.

The signal from transducer 42 is monitored based on a sample rate that is a matter of design choice based upon the particular circuit design, which for the illustrated embodiment, is ten times per second. If the pressure which is sensed at transducer 42 is less than one-half atmosphere, the system moves to that portion of the program which commences with step 200. At that step the system first determines whether it is in the first pass through the loop started by step 200 and if so moves to step 202 where the memory is updated. The effect of updating the memory at step 202 is that the time with respect to termination of the last inflation is recorded and stored in the data memory 96. Once that step has been completed, the system then moves to step 204. In the alternative, if at step 200 the system determines that it is not the first pass through this loop of the program, the system moves directly to step 204 and displays the current data with respect to the inflation number, time, and pressure. The system then moves to step 206 where the processor checks the menu switch 74.

If the menu switch is activated in this condition the system moves to the next step 210 where the last inflation data can be marked as an initial test or not, as desired by the system user. If the initial inflation is merely a test it is marked at step 212 prior to returning to step 192, otherwise the system moves to step 214 to determine whether any previously recorded inflation data is to be scrolled. If the data is scrolled the system moves to step 216 and retrieves and displays in sequence all previously recorded inflation data for each prior inflation event, otherwise the system jumps to step 218.

Similarly, the system can also proceed through steps 218, 222, and 226 which will permit the transducer to again be zeroed (step 220), or to set a new maximum positive inflation pressure (step 224) or to change the pressure units (step 228) by entering any of these selections using the select switch 76.

Once the inflation pressure applied to the balloon catheter begins to exceed a predetermined level, as for example about one-half atmosphere by insertion of the syringe plunger, the system moves from step 198 to the program step 230. At that step the system determines whether this is the first time through the part of the program loop which beings with step 230 and if so updates the memory at step 232. The effect of updating the memory at step 232 is that the processor causes the duration of the previous inflation to be recorded. After update memory step 232 has been performed, or in each subsequent pass through step 230, the system then moves to step 234 where the system checks to determine whether the inflation pressure has reached any selected maximum positive inflation pressure input for this inflation event. If the selected maximum inflation pressure is reached the system moves to step 238 and causes the pressure display readout 72 on control panel 64 to begin flashing so as to signal the system user that the selected maximum inflation pressure has been reached. If the selected maximum inflation pressure has not been reached or if none was selected, the system then jumps as illustrated at line 236 to step 240.

At step 240 the system checks to determine whether any selected duration has yet been clocked with respect to a selected duration for application of positive pressure and if so then moves to step 244 so as to cause the time display readout 70 to begin flashing, thereby signalling the system user that the selected duration has been achieved. If no duration is input or if the selected duration has not been reached the system moves to step 246 as indicated at line 242 which causes the system to display the current data with respect to the inflation pressure being applied and the length of time that positive inflation pressure has been applied. The system then returns to the beginning of the loop at step 192.

It will be appreciated that the digital processor U1 of FIG. 5A, which is an 8032 microprocessor as identified in Table I, could be programmed so as to implement the above-described method using any one of a variety of different programming languages and programming techniques. Attached hereto as Appendix A is one such program which was prepared for use with the 8032 microprocessor and the circuit configuration as illustrated in FIGS. 5A and 5B. The attached program comprises a listing of source code and assembly language for the 8032 microprocessor.

Figure 6E:
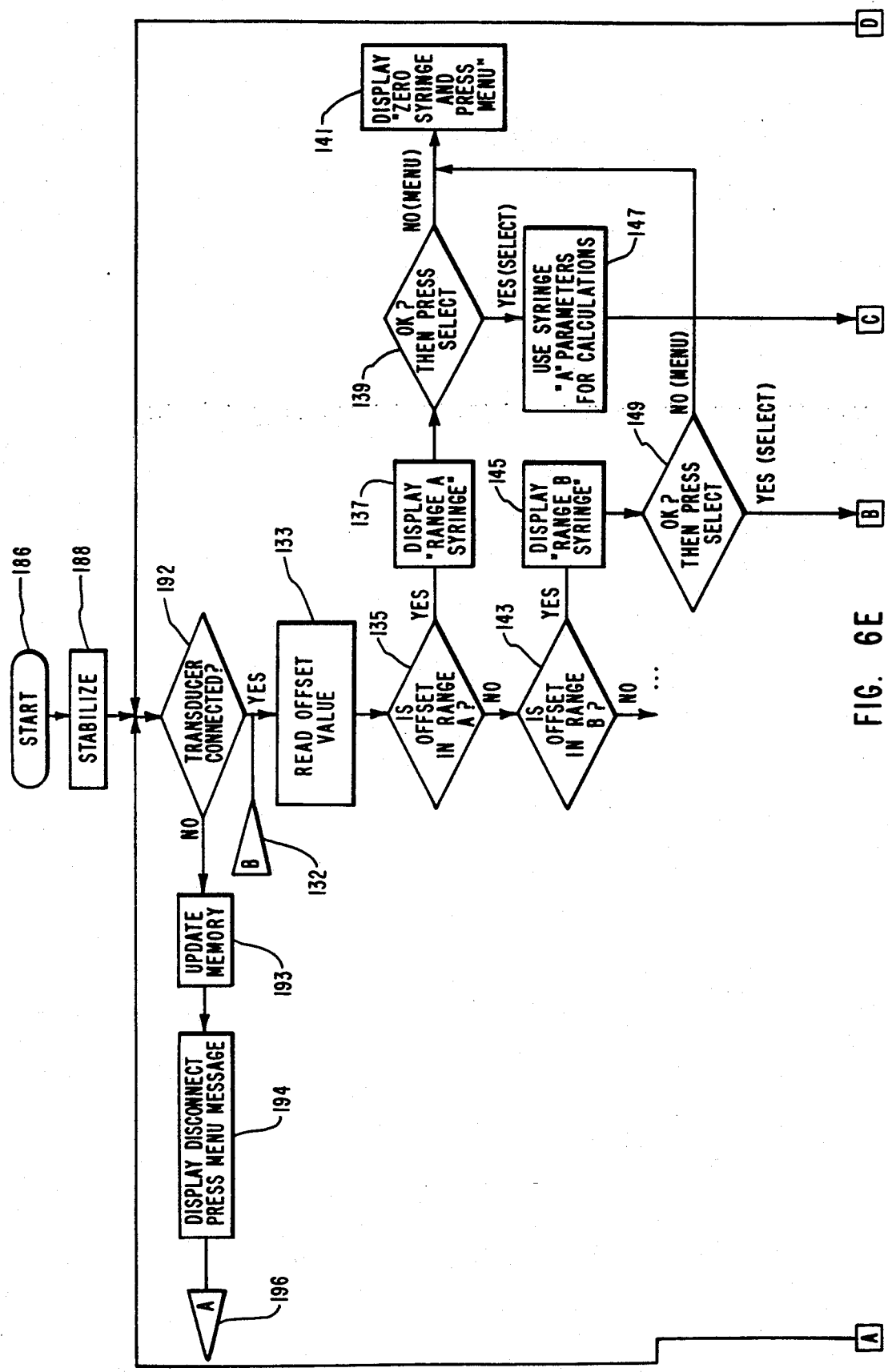
FIGS. 6E through 6G taken together illustrate a flow chart showing a second presently preferred method for programming the digital processor of the electronic circuit means utilized in the syringe system of FIGS. 2-5 in accordance with another method of the present invention.
Figure 6F:
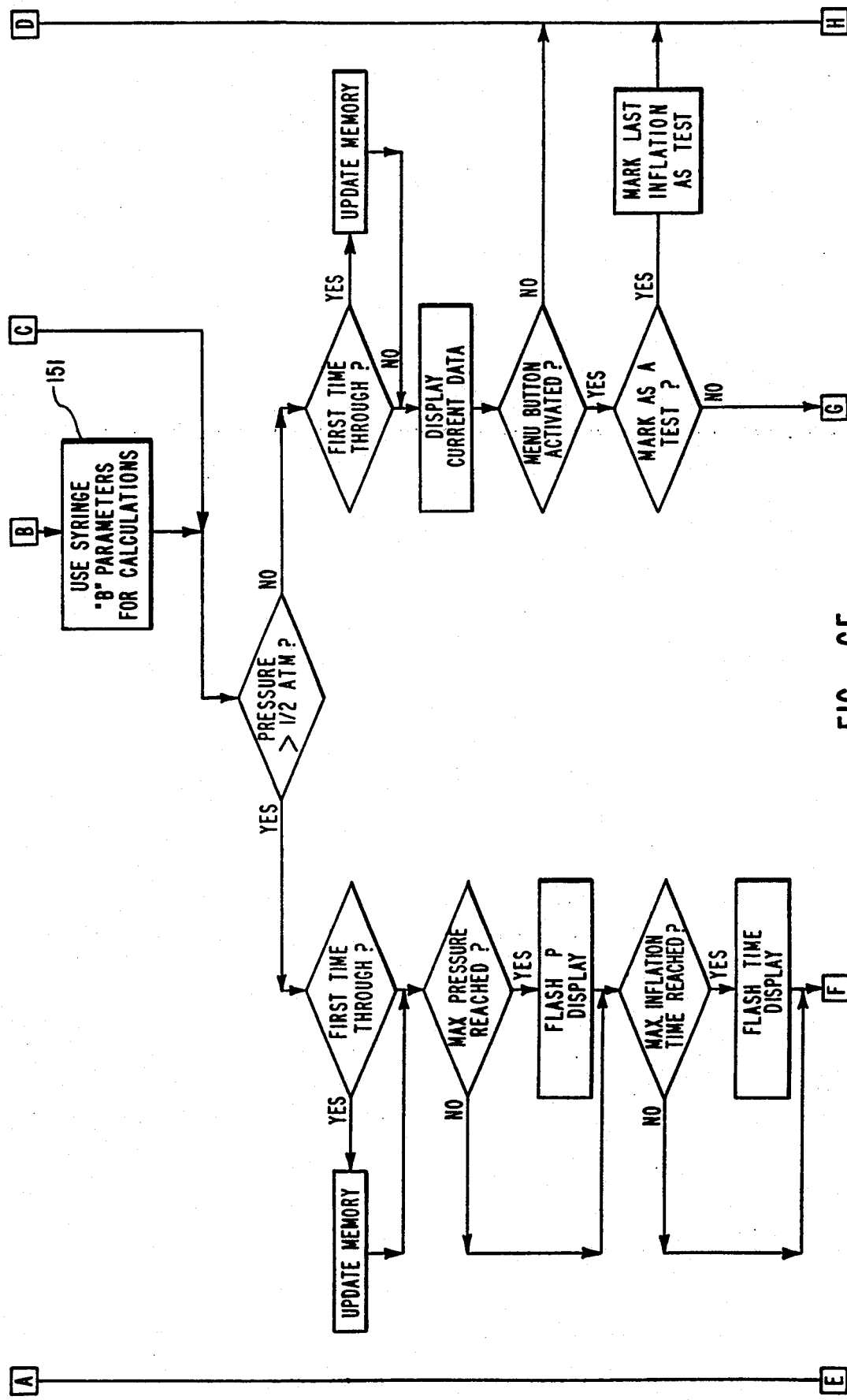
Figure 6G:
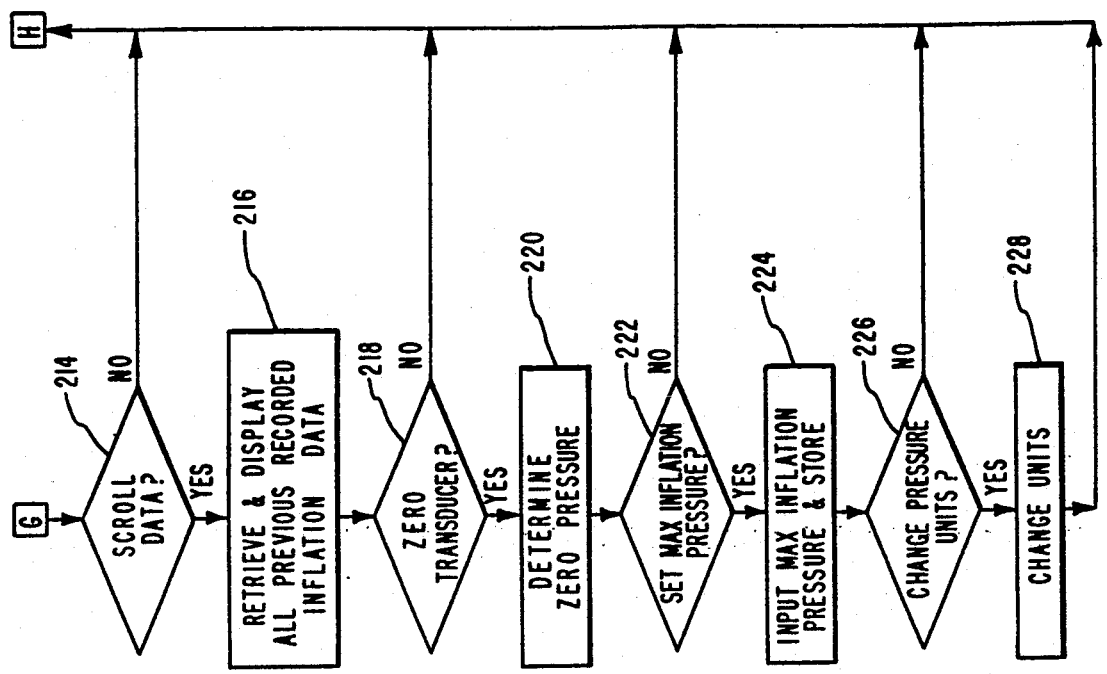
Figure 6G:
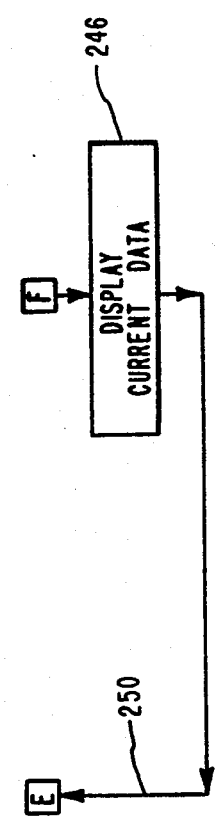

An alternative embodiment for programming and controlling the syringe system 14 is illustrated in FIGS. 6E–6G. Utilizing the programmed instructions of that embodiment of the method, the system is first started and stabilized at steps 186 and 188 as described above. Thereafter, the system then carries out step 192 where it is determined whether the transducer is connected, in the same manner as previously described. If the transducer is not connected the steps 193 and 194 are as described above in connection with the embodiment of the method of FIGS. 6A–6D.

If the transducer is connected the microprocessor 90 then proceeds to read the offset value of the connected transducer as indicated at step 133. The transducer offset value is the actual pressure which is read by the transducer when there is no pressure applied by the syringe system.

This offset is then compared to a plurality of offset values which have previously been stored in the program memory of the microprocessor 90. By taking the difference between the actual offset value and the other previously stored offset values which have been programmed into the microprocessor 90, it can be determined whether the actual measured offset value is within any one of a number of preselected ranges for the offset value.

For example, as illustrated in FIG. 6E at step 135, it may be determined whether the measured offset is within a first range, range A. If so, the system then displays a message at step 137 to the system user which identifies to the user the particular offset range which was identified and the type of syringe which corresponds to that range of offset values. In other words, the transducer 42 may be designed so that it has a selected value of offset at the time the transducer circuit is manufactured.

This can advantageously be used to identify different types of syringes that may be useful for different types of applications or patients. In this manner, the system can identify whether the correct type of syringe has been placed into use for the intended application or the type of patient for which the procedure is being conducted.

Once the system has displayed at step 137 the user message which identifies the type of syringe, the processor 90 then moves to step 139 and requires the system user to verify that the type of syringe identified is the correct type. This is done by pressing the select switch on the control panel. If the syringe is not the correct type of syringe the menu switch is activated and the control panel then displays the zero syringe and press menu instruction and awaits for a new syringe to be connected. Otherwise, the system moves to step 147 where the particular parameters for the type of syringe selected (e.g. sensitivity, signal gain and/or linearity or the like for that type of syringe) are then retrieved from the program memory and used throughout the remaining digital processing steps. The remaining digital processing steps, which are illustrated at FIGS. 6F–6G starting at step 198 are the same as those which have previously been described in connection with the embodiment of FIGS. 6A–6D.

Returning to FIG. 6E, if the system determines at step 135 that the measured offset value is not within a first range, range A, the system then moves to step 143 where a similar determination is made for the next range of offset values, range B. At steps 145, 149 and 151 the system follows the same type of program steps previously described in connection with steps 137, 139 and 141. In this fashion the system continues to check until it determines which selected range of offset values corresponds to the type of transducer which is contained on the syringe that has been connected for use, identifies the user of this and then awaits for the user to confirm that this is the proper type of transducer with the appropriate parameters for the selected procedure or type of patient.

B. FIG. 10

Figure 10:
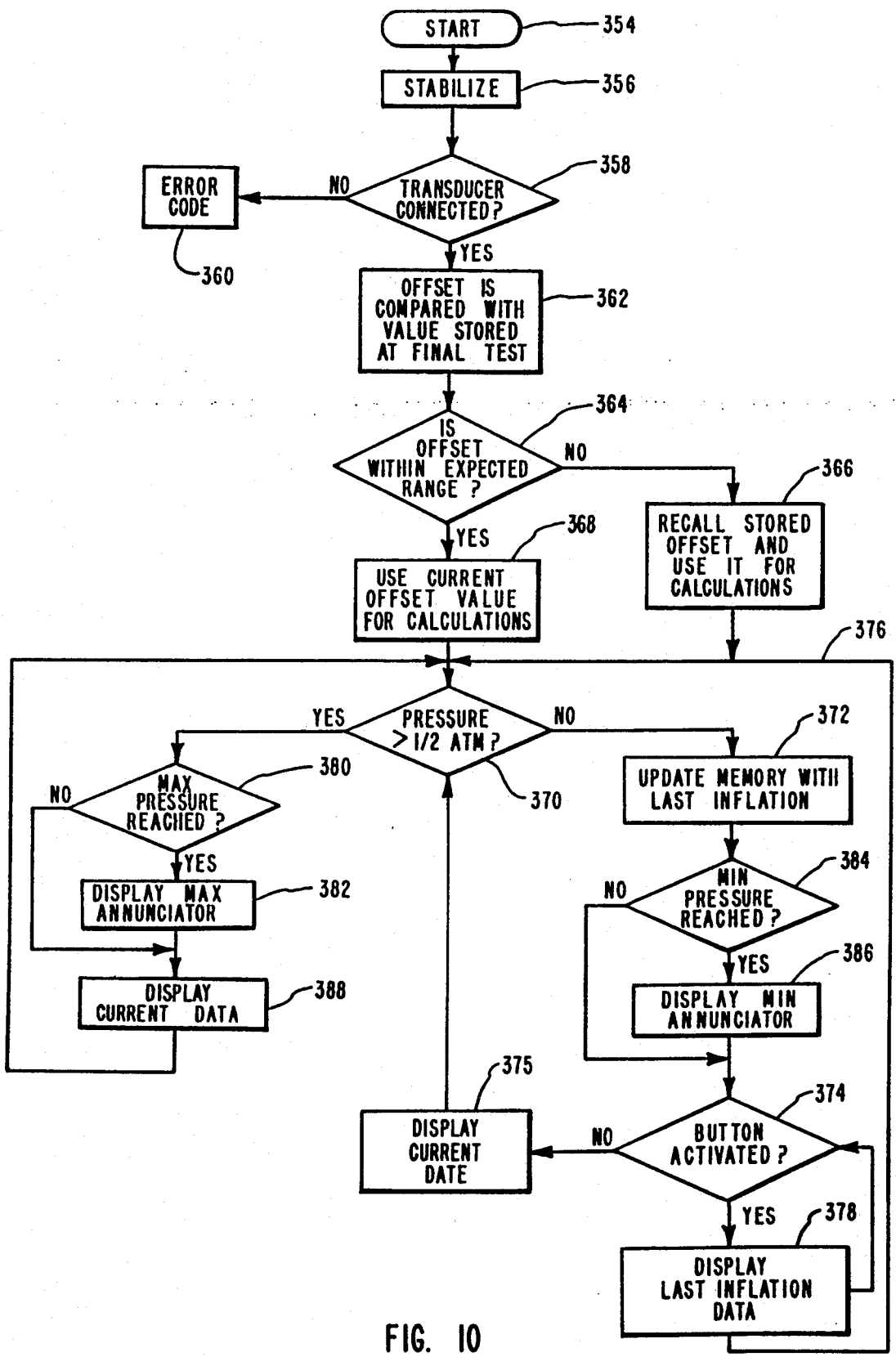
FIG. 10 illustrates a flow chart showing one presently preferred method for programming the digital processor of the electronic circuit means which is utilized for the syringe system in the embodiment of FIG. 7.

The embodiment of the program instructions as illustrated in the flow chart of FIG. 10 is particularly designed for programming the microprocessor 290 which is illustrated and described in connection with the self-contained, totally disposable syringe system 14a of FIGS. 7-9.

Starting at steps 354 and 356, once the button 278 is activated, the system is started and is stabilized as described above. The microprocessor 290 then moves to step 358 where it checks to make certain that the transducer 42 is connected to the rest of the circuitry. If the system detects at step 358 that the transducer is not connected, an error message is displayed at the digital readout 66a as indicated at step 360. The error code simply indicates that the electronic circuitry is faulty.

If the microprocessor 290 detects that the transducer 42 is connected, the microprocessor 290 then moves to step 362. At this step the microprocessor 290 attempts to determine the transducer's offset for the case where no pressure is being applied by the syringe. The preferred setup protocol is for a system user to measure offset at no pressure. If this preferred procedure is followed, then the microprocessor will use the measured offset in all subsequent determinations of pressure. However, if a user forgets to measure the offset at zero pressure, then the system defaults to an offset value that is determined and previously stored at the time the circuit is assembled. In the method as illustrated in FIG. 10, this is shown at step 362, where the microprocessor 290 attempts to determine the transducer's offset for the case where no pressure is being applied by the syringe. If the user has not applied any pressure, the measured offset will be very close to the previously stored offset value, so the microprocessor will determine that at step 364 and will then proceed to use the current offset value as shown at step 368. If, however, the user begins to apply pressure before determining the zero offset, that will also be detected at step 364 and the microprocessor 290 will then move to step 366 and will default to the use of the previously stored offset value in all subsequent determinations of pressure.

By testing each transducer as it is manufactured and connected to the electronic circuitry of the controller 20a, and by storing the offset value which is determined when the final testing of the circuit is performed, it is possible to provide protection against any failure to take into account the transducer's offset with respect to the actual pressure measurements which are subsequently displayed when using the syringe system 14a. Thus, in accordance with the above-described program steps, if a system user forgets to zero the transducer of the syringe system and simply begins to immediately apply inflation pressure, the system is designed to default to the previously stored offset value and use that as the appropriate offset with respect to the pressures which are being sensed and displayed. If, on the other hand, the system user does follow proper procedure and zeros the transducer of the syringe system, then the actual offset value which is detected will be used to adjust the inflation pressures which are monitored.

With continued reference to FIG. 10, once either the actual or previously stored offset value has been identified for use as described, the microprocessor 290 then moves to step 370 and if the inflation pressure is greater than a predetermined value, the microprocessor then moves to step 380 where the electronic circuitry begins to monitor the inflation pressure. If a preprogrammed maximum value has been reached (typically 20-25 atmospheres for angioplasty), as indicated at step 382 the "max" annunciator is displayed. Otherwise, microprocessor 290 jumps to step 388 and the digital display simply begins displaying the current inflation pressure as it is sensed, along with the duration of the inflation.

The microprocessor 290 returns to step 370 where the same procedure as described above is followed until the system determines at step 370 that the inflation pressure is less than one-half an atmosphere. At that point, the microprocessor 290 then moves to step 372 where the digital data memory is updated with respect to the last inflation event by storing the maximum inflation pressure and the duration of the inflation. The system continues with step 384 where it determines whether a preprogrammed minimum pressure (typically about −0.4 atmospheres) has been reached. If the minimum pressure is reached the "min" annunciator is displayed as at step 386, otherwise that step is jumped. The system then determines whether the button 278 has been activated, as indicated at step 374, and if so the digital data for the last inflation event is displayed at step 378. If the button 278 is not activated the system continues to display the current data at step 375 and then returns to step 370 as previously described.

As in the case of the other embodiments, the digital processor 290 could be programmed so as to implement the above described method using any of a variety of different programming languages or programming techniques. Attached hereto as Appendix B is an example of a program which has been prepared for use with the microprocessor as identified in Table II and as illustrated in FIGS. 9A and 9B. The attached program comprises a listing of source code and assembly language for the microprocessor.

The invention may be embodied in other specific forms without departing from its spirit or essential characteristics. Accordingly, the described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

TABLE I

| Schematic Reference | Part |
|---|---|
| X1 | 11.059 MHz |
| C3 | 10 Mfd |
| R1 | 8.2K |
| U1 | 8032 |
| U2 | 74HC573 |
| C5, C7, C14 | .01 Mfd |
| C1, C2 | 33 pf |
| P1 | CONNECTOR DB25F AMP 745389-1 |
| U4 | DS1243 |
| U5, U6, U7 | DL3416 SIEMENS |
| U8 | ADC0834 TI |
| U9 | MAX233 |
| D1 | IN5291 |
| U3 | 27256 |
| U11 | UA7805UC FAIRCHILD |
| C4 | 4700 Mfd |
| PCB 1 | Printed circuit board |
| JP3 | Female RJ-11 (6 pos-4 wire) |
| JP1 | HEADER 4 |
| J1 | AC line cord |
| R17 | MMSI TRANSDUCER |
| U10 | LM324 |
| R5 | 10K DIP |
| R7, R9, R10, R11 | 10K DIP |
| K6 | 10K-15T VRN 752-208-103 |
| R12, R13 | 100K |
| R2 | 10K |
| C6, C8, C9, C10, C11, C12, C13 | .01 Mfd |
| C15, C16 | .2 Mfd |
| T1 | Toltek Custom transformer |
| D2 | GI 2KBP04 |
| F1 | .25 AMP |
| SW1 | Micro Switch & Cover |

TABLE II

| Schematic Reference | Part |
|---|---|
| Y1 | CST 4.19 MHZ (KYOCERA) |
| U2 | LM324DT (SGS) |
| B1, B2 | CR20162HM (Panasonic) |
| RN1 | 100K (CTS) |
| R1, R3, R4, R6, R8 | NRC12100KFTR (NIC) |
| R2 | NRC127.32KFTR (NIC) |
| R5 | NRC121MEGFTR (NIC) |
| U1 | NEC75328GC173/3B9 (NEC) |
| D1, D2, D3, D4 | MTBL3410 (MARKTECH) |

APPENDIX A

```
/* IFCODE1.C Intelliflator source code for compiling and linking for the 80C32 small memory,reentrant model.

Copyright 1988, 1989 by Merit Medical Systems, Inc. All rights reserved.

This is an unpublished work which contains confidential information that is proprietary to Merit Medical Systems, Inc. Any unauthorized use, duplication or disclosure is strictly prohibited. */ include <stdio.h>   /* required for printf, putchr */

/* #define host_debug */ ifdef host_debug
define clear_bit(x) putchar('0')
#define set_bit(x) putchar('1')
#define read_bit(x) ((printf(#x)),(getch()-48))
#define read_XDATA(x) ((printf("read_X=")),(getch()))
#define write_XDATA(y,x) printf("%c",x)
#define output(y,x) printf("port_one_initialized\n")
#else
#include <io51.h>    /* required for bit_set, read_X */
#endif
```

```c
#define SERIAL_RATE 0xFD   /*   0xFD =  9600 bps
                                0xFA =  4800 bps
                                0xF4 =  2400 bps
                                0xE8 =  1200 bps  */ define TRUE 1
define FALSE 0
#define LF 10   /* ASCII Line feed */
#define pres '0'    /* ch 0 on a/d for pressure */
#define bat '3'     /* ch 3 on a/d for Battery voltage */
#define nleg '1'    /* ch 1 on a/d for negative transducer leg */
#define pleg '2'    /* ch 2 on a/d for positive transducer leg */
#define swatch 0x1FFF  /* swatch scratch address */
#define syr_max 0x1FFE /* the maximum syringe number in memory */
#define next_mem 0x1FFC /* storage location for hi pointer to next available
                           memory address, lo memory = 0x1FFD */
#define disp_addr_base 0x9FFB  /* left display position, RT = 9FF0
                                  Caution: overlaps data RAM at 1FF0-1FFB */
#define menu_switch read_bit(P1_6_bit)
#define set_switch read_bit(P1_7_bit)
define no_syringe 100  /* the a/d of nleg above which is no syringe plugged in */ const char ver[] = "  031189V1.0";
const char header_string[] = "\nMerit Medical INTELLIFLATOR";
const char patient_string[]= "Patient Name:_____\n";
const char trailer[] = "*****************************************\n\n\n\n";
const char syrnumstring[] = "Syringe Number ";
const char mem_err[] = "Memory Error\n";
const char test_header[] = "#T  DATE     TIME  INF  SEC ATM\n";
const char printed[] = "Printed: ";

int p;          /* positionof presentmemory pointer */
char dt_string[23]; /* date time and temp string for printout */
char p_s[38];   /* print output string */
char c[5];          /* five ascii characters */
char d[12];         /* the twelve display characters */
char raw_d_t[8];    /* raw date and time from/to swatch */
int tempint;    /* temporary global integer for debugging */
char pflag;         /* syringe inflated flag */
char dt;        /* dt=1, date updating;dt = 0 time updating */

/* structure of memory storage record
    m[0] char syr_num     syringe number, range 1 to 255
    m[1] char type        type of storage entry :
                    "I" = inflation
                    "D" = delay between inflations
                    "N" = syringe change
                    "T" = test inflation
```

```
                            "Z" = syringe re-zeroed
                            "X" = syringe disconnected
    m[2-18] char dt_string[17]     date and time string
    m[19]   char inf_nmbr   equal to inf_nmbr
    m[20-21] int  inf_sec   equal to inf_sec
    m[22] char  pressure       equal to (char)pressure in atmospheres
                                        or zero for
*/
char pres_high;      /* highest pressure reached during inflation */
char syr_now;  /* the current syringe date to be printed or stored */
float zero_pres;  /* syringe reading for zero pressure */
char units ;  /* display units  1=ATM, 0=PSI */
float max_pres ;  /* maximum pressure in tenths of ATM units*/
float pressure;       /* syringe pressure */
char etmin;       /* ellapsed time minutes */
char etsec;       /* ellapsed time seconds */
char inf_nmbr;    /* inflation number */
int infsec;       /* inflation time */
long period_begin;/* the beginning of a period in seconds */
char first;          /*  indicates pre-inflation period */
char hist_flag;    /* indicates historisis on inflation  */ extern void dt_read();
extern void menu();
extern void delay(int d);
extern void int_to_ascii(int n);
extern void swatch_attn();
extern void swatch_read();
extern void swatch_write();
extern void ad_to_ascii(char n);
extern void get_pressure();
extern void output_char(char c);
extern void output_string(char * msg);
extern void clear_data();
extern char read_ad(char n);

void stabilization();
void display();
void roll_dot();
void time_convert();
void date_convert();
void test_out();
void digit_set(char n);
void start_period();
long swatch_to_seconds();
void initialize();
void get_dtstring();
void print_format(int t);
```

```c
void output_syringe_data(char s);
void store_memory_string(char typ, char p);
void scroll_data();
void print_data();

/* ------------------------------------------------ */
void display(ch1,ch2,ch3,ch4,ch5,ch6,ch7,ch8,ch9,ch10,ch11,ch12)
     /* write ch1-ch12 to dl3416 positions 1-12 */ char ch1,ch2,ch3,ch4,ch5,ch6,ch7,ch8,ch9,ch10,ch11,ch12;
         /* characters to be displayed */
{
#ifdef host_debug
printf("\n");
#endif
     write_XDATA(disp_addr_base-0,ch1);
     write_XDATA(disp_addr_base-1,ch2);
     write_XDATA(disp_addr_base-2,ch3);
     write_XDATA(disp_addr_base-3,ch4);
     write_XDATA(disp_addr_base-4,ch5);
     write_XDATA(disp_addr_base-5,ch6);
     write_XDATA(disp_addr_base-6,ch7);
     write_XDATA(disp_addr_base-7,ch8);
     write_XDATA(disp_addr_base-8,ch9);
     write_XDATA(disp_addr_base-9,ch10);
     write_XDATA(disp_addr_base-10,ch11);
     write_XDATA(disp_addr_base-11,ch12);
#ifdef host_debug
printf("\n");
#endif
}

/* ------------------------------------------------ */
void stabilization()
{
int i;

display('S','T','A','B','I','L','I','Z','I','N','G',' ');
     for(i=0;i<5;delay(30000),i++);
}
/* ------------------------------------------------ */ void digit_set(char n)   /* blinks,displays and changes time/date */
{
char temp;
```

```
do
    {
    temp = d[n];
    d[n] = ' ';
    display(d[0],d[1],d[2],d[3],d[4],d[5],d[6],d[7],' ','0','K','?');
    delay(500);
    if ( set_switch == 0 )
        {
    temp++;
    switch(n)
    {
        case 0:
            if(dt == 1)
                {
                if (temp > 49)
                    temp = 48;
                }
            else
                {
                if (temp >50)
                    temp = 48;
                }
            break;
        case 3:
            if(dt == 1)
                {
                if (temp > 51)
                    temp = 48;
                }
            else
                {
                if (temp >53)
                    temp = 48;
                }
            break;
        case 6:
            if(dt ==1)
                {
                if(temp > 57)
                    temp = 48;
                }
            else
                {
                if (temp > 53)
                    temp = 48;
                }
            break;
```

```
                    default:
                        {
                        if( temp >57)
                            temp =48;
                        }
                    }
                do
                    {
                    }while (set_switch == 0);
                } d[n] = temp;
        display(d[0],d[1],d[2],d[3],d[4],d[5],d[6],d[7],' ','O','K','?');
        delay(500);
        } while ( menu_switch == 1 );
do
    {
    }while (menu_switch == 0);
    delay(1000);
}
/* ---------------------------------------------- */ void roll_dot()  /* rotates a dot through the display */
    {
    int n;
    if (read_XDATA(syr_max) >= 90 || read_XDATA(next_mem) >0x1AF4)
                            /* 300 entries out of 355 */
        {
        display('N','O',' ','M','E','M','O','R','Y',' ',' ',' ');
        delay(20000);
        goto R_D1;
        }
    while(TRUE)
    {
        for(n=0;n<12;n++)
        {
            display('N','O',' ','S','Y','R','I','N','G','E',' ',' ');
            delay(100);
            if ( read_ad(nleg) < no_syringe)
                goto EXIT;
            if (menu_switch == 0 )
                {
R_D1:           menu();
                if(read_XDATA(0x00) == 0)
                    goto EXIT4; /* data cleared skip print */
                do          /* print data */
                {
                display('P','R','I','N','T',' ','D','A','T','A',' ','?');
```

```c
    delay(1000);
if (set_switch == 0 )
    {
    syr_now = read_XDATA(syr_max);
    if(syr_now == 0)
        {
        display('N','O',' ',' ','D','A','T','A',' ',' ',' ',' ',' ',' ');
        delay(5000);
        goto EXIT4;
        }
    do
        {
        }while(set_switch ==0);
    do
        {
        display('P','R','I','N','T',' ',' ','A','L','L',' ',' ','?',' ');
        if(set_switch == 0)
            {
            syr_now = 1;
            do
                {
                print_data();
                syr_now++;
                }while (syr_now <= read_XDATA(syr_max));
            goto EXIT4;
            }
        }while (menu_switch == 1);
    syr_now = read_XDATA(syr_max);
    do
        {
        }while(menu_switch == 0);
    do
        {
        ad_to_ascii(syr_now);
        display('S','Y','R','I','N','G','E',':',c[1],c[2],' ',' ');
        do
            {
            }while (set_switch == 0 );
        delay(500);
        if (set_switch == 0 )
            {
            syr_now--;
            if (syr_now == 0 )
                syr_now = read_XDATA(syr_max);
            }
        }while (menu_switch == 1 );
    print_data();
    }
```

```c
            }while( menu_switch == 1 );
        do
        {
        }while(menu_switch == 0);
        }
    EXIT4: ;
    }
}
EXIT: ;
syr_now = 1 + read_XDATA(syr_max);

write_XDATA(syr_max,syr_now);
store_memory_string('N',0);
zero_pres = 0;
}

/* ---------------------------------------------- */
void print_data()
{
    display('P','R','I','N','T','I','N','G',' ',' ',' ',' ',' ');
    output_string(header_string);
    output_string(ver);
    output_char(LF);
    get_dtstring();
    output_string(printed);
    output_string(dt_string);
    output_char(LF);
    output_string(patient_string);
    output_syringe_data(syr_now);
    output_string(trailer);
}
/* ---------------------------------------------- */
void store_memory_string(char typ, char p)
                    /* stores a 23 char string with
                       of type typ information for pressure p.
                    */
{
int i;
int n;
p_s[0] = syr_now;
p_s[1] = typ;
get_dtstring();
for(i=0;i<17;p_s[2+i]=dt_string[i],i++);
switch(typ)
{
    case 'I' :
    case 'D' :
        p_s[19] = inf_nmbr;
```

```
            p_s[20] = (char)(infsec/256);
            p_s[21] = (char)(infsec%256);
            p_s[22] = p;
            break;
        default :
            for(i=0;i<4;p_s[19+i]=0,i++);
    }
    n = ((256) * (read_XDATA(next_mem))) + (read_XDATA(next_mem+1));
    if ( typ == 'T')
        {
        if (read_XDATA(n-22) == 'I')
            write_XDATA(n-22,'T');
        }
    else
        {
        for(i=0;i<23;i++)
            write_XDATA(n+i,p_s[i]);
        n = n + 23;
        write_XDATA(next_mem,(char)(n/256));
        write_XDATA(next_mem+1,(char)(n%256));
        }
}
/* ---------------------------------------------- */
void scroll_data()

{
int i;
p = ((256) * (read_XDATA(next_mem))) + (read_XDATA(next_mem+1));
if (p == 0)
    {
    display('N','O',' ','D','A','T','A',' ',' ',' ',' ',' ',' ');
    goto EXIT6;
    }
p -=23;
while(read_XDATA(p) == syr_now)
    {
    for(i=0;i<23;dt_string[i]=read_XDATA(p+i),i++);
switch(dt_string[1])
{
case 'D':
case 'I':
case 'T':
    {
    d[0]=dt_string[1];
    d[1]=' ';
    etmin = (char)((dt_string[20]*256+dt_string[21])/60);   /* Inf sec */
    etsec = (char)((dt_string[20]*256+dt_string[21])%60);
    ad_to_ascii(etmin);
```

```c
d[2] = c[1];
d[3] = c[2];
ad_to_ascii(etsec);
if ( c[1] == ' ')
     c[1] = '0';
d[4] =':';
d[5] = c[1];
d[6] = c[2];
d[7] = ' ';
if (dt_string[1] == 'D')
    {
    d[8] = ' ';
    d[9] = 'N';
    d[10]= 'E';
    d[11]= 'G';
    }
else
    {
    pressure=(float)dt_string[22];
    if ( units == 1)
        {
        ad_to_ascii((char)pressure);
        d[8] = c[0];
        d[9] = c[1];
        d[10] = '.';
        d[11] = c[2];
        }
    else
        {
        d[8] = ' ';
        int_to_ascii((int)(pressure * 1.4696));
        switch (c[4])
        {
        case 49 :
                c[4] = 48;
                break;
        case 51 :
                c[4] = 50;
                break;
        case 53 :
                c[4] = 52;
                break;
        case 55 :
                c[4] = 54;
                break;
        case 57 :
                c[4] = 56;
                break;
        }
```

```
                    d[9] = c[2];
                    d[10] = c[3];
                    d[11] = c[4];
                    } /* end if/else */
                } /* end D/I if/else */
            break;
            } /* switch I/D/T */
        case 'Z':
            {
            d[0] ='Z';
            d[1] ='E';
            d[2] ='R';
            d[3] ='O';
            for(i=0;i<9;d[4+i]=' ',i++);
            break;
            }
        case 'R':
            {
            d[0] ='R';
            d[1] ='E';
            d[2] ='A';
            d[3] ='D';
            d[4] ='Y';
            d[5] =' ';
            d[6] =' ';
            d[7] =' ';
            d[8] =' ';
            d[9] =' ';
            d[10]=' ';
            d[11]=' ';
            break;
            }
        case 'X':
            {
            d[0] ='D';
            d[1] ='I';
            d[2] ='S';
            d[3] ='C';
            d[4] ='O';
            d[5] ='N';
            d[6] ='N';
            d[7] ='E';
            d[8] ='C';
            d[9] ='T';
            d[10]=' ';
            d[11]=' ';
            break;
            }
```

```c
    default:
        {
        d[0] ='E';
        d[1] ='N';
        d[2] ='D';
        d[3] =' ';
        d[4] ='O';
        d[5] ='F';
        d[6] =' ';
        d[7] ='D';
        d[8] ='A';
        d[9] ='T';
        d[10]='A';
        d[11]=' ';
        display(d[0],d[1],d[2],d[3],d[4],d[5],d[6],d[7],d[8],d[9],d[10],d[11]);
        delay(2000);
        goto EXIT6;
        }
    } /* outer switch */
    display(d[0],d[1],d[2],d[3],d[4],d[5],d[6],d[7],d[8],d[9],d[10],d[11]);
    delay(2000);
    do
        {
            if(menu_switch == 0)
                goto EXIT6;
            } while(set_switch ==1);
        p -= 23;
        }/* end while */
EXIT6:;
do
{
}while(menu_switch == 0);
}

/* ---------------------------------------------- */
void time_convert()
    {
    d[1] = (raw_d_t[3] & 0x0F ) + 48;
    d[0] = ((raw_d_t[3] & 0x3F) >> 4 ) +48;
    d[2] = ':';
    d[4] = (raw_d_t[2] & 0x0F ) + 48;
    d[3] = (raw_d_t[2] >> 4 ) + 48;
    d[5] = ':';
    d[7] = (raw_d_t[1] & 0x0F ) + 48;
    d[6] = (raw_d_t[1] >> 4 ) +48;
    }
/* ---------------------------------------------- */
```

```c
void date_convert()
    {
    d[1] = (raw_d_t[6] & 0x0F ) + 48;
    d[0] = (raw_d_t[6] >> 4 ) +48;
    d[2] = '/';
    d[4] = (raw_d_t[5] & 0x0F ) +48;
    d[3] = (raw_d_t[5] >> 4 ) + 48;
    d[5] = '/';
    d[7] = (raw_d_t[7] & 0x0F ) + 48;
    d[6] = (raw_d_t[7] >> 4 ) + 48;
    }
/* ---------------------------------------------- */
long swatch_to_seconds() /* converts a swatch reading of
                            date,hour, minute and seconds to seconds */
{
long t;
    t = (((raw_d_t[5] >> 4)*10 + (raw_d_t[5] &0x0F )) * 86400)
      + ((((raw_d_t[3] & 0x3F) >> 4)*10 + (raw_d_t[3] &0x0F )) * 3600)
      + (((raw_d_t[2] >> 4)*10 + (raw_d_t[2] &0x0F )) * 60)
      + (((raw_d_t[1] >> 4)*10 + (raw_d_t[1] &0x0F )));
    return t;
}
/* ---------------------------------------------- */
void get_dtstring() /* gets and converts date and time to print string
                       format dt_string */
{
int i;
    swatch_read();
    date_convert();
    for (i=0;i<8;i++)
        dt_string[i] = d[i];
    time_convert();
    for (i=0;i<8;i++)
        dt_string[9+i] = d[i];
    dt_string[8]=' ';
    dt_string[17] = '\n';
    dt_string[18] = 0x00;
}

/* ---------------------------------------------- */
void start_period() /* assigns the current time to period_begin */

{
swatch_read();
period_begin = swatch_to_seconds();
}

/* ---------------------------------------------- */
```

```c
void test_out()  /* displays battery and pressure */

{
int i;
int j;
display('T','E','S','T',' ','R','O','U','T','I','N','E');
do
    {
do
        {
        }while (menu_switch == 0);
    ad_to_ascii(read_ad(bat));
    d[2] = c[0];
    d[3] = c[1];
    d[4] = c[2];
    ad_to_ascii(read_ad(pres));
    d[9] = c[0];
    d[10] = c[1];
    d[11] = c[2];
    display('B',':',d[2],d[3],d[4],' ',' ','P',':',d[9],d[10],d[11]);
    delay(1000);
    }while (set_switch == 1);
do
    {
    do
        {
        }while (set_switch == 0);
    ad_to_ascii(read_ad(pleg));
    d[2] = c[0];
    d[3] = c[1];
    d[4] = c[2];
    ad_to_ascii(read_ad(nleg));
    d[9] = c[0];
    d[10] = c[1];
    d[11] = c[2];
    display('+',':',d[2],d[3],d[4],' ',' ','-',':',d[9],d[10],d[11]);
    delay(1000);
    if ( menu_switch == 0 )
        {
        do
            {
            }while (menu_switch == 0);
        display('P','R','I','N','T','I','N','G',' ',' ',' ',' ');
        ad_to_ascii(read_ad(bat));
        p_s[9] = c[0];
        p_s[10] = c[1];
        p_s[11] = c[2];
        ad_to_ascii(read_ad(pres));
```

```
        p_s[2] = c[0];
        p_s[3] = c[1];
        p_s[4] = c[2];
        ad_to_ascii(read_ad(pleg));
        p_s[16] = c[0];
        p_s[17] = c[1];
        p_s[18] = c[2];
        ad_to_ascii(read_ad(nleg));
        p_s[23] = c[0];
        p_s[24] = c[1];
        p_s[25] = c[2];
        p_s[0]='P';
        p_s[1]=':';
        p_s[5]=' ';
        p_s[6]=' ';
        p_s[7]='B';
        p_s[8]=':';
        p_s[12]=' ';
        p_s[13]=' ';
        p_s[14]='+';
        p_s[15]=':';
        p_s[19]=' ';
        p_s[20]=' ';
        p_s[21]='-';
        p_s[22]=':';
        p_s[26]='\n';
        p_s[27]=0x00;
        output_string(p_s);
        }
if(set_switch == 0)
        {
        output_char(LF);
        output_string(test_header);
        for(i=0;i<20;i++)
            {
            for(j=0;j<31;p_s[j]=' ',j++);
            for(j=0;j<23;p_s[j] = read_XDATA(j+23*i),j++);
            int_to_ascii((256*(int)p_s[20])+((int)p_s[21]));
            p_s[23] = c[0];
            p_s[24] = c[1];
            p_s[25] = c[2];
            p_s[26] = c[3];
            p_s[27] = c[4];
            ad_to_ascii(p_s[19]);
            p_s[19] = c[0];
            p_s[20] = c[1];
            p_s[21] = c[2];
            ad_to_ascii(p_s[22]);
```

```
            p_s[28] = c[0];
            p_s[29] = c[1];
            p_s[30] = c[2];
            p_s[22] = '-';
            p_s[31]='\n';
            p_s[32]=0x00;
            if(p_s[0] == 0)
                {
                    output_char('*');
                    output_char(LF);
                }
            else
                {
                p_s[0] +=48;
                output_string(p_s);
                }
            }
        if((menu_switch==0)&&(set_switch==0))
            clear_data();
        }
}while (TRUE);
}
/* ------------------------------------------------ */
void initialize()  /* initialize the hardware */

{
/* initialize timer 1 as baud rate generater for serial interface */
output(PCON, 0x00);       /* set SMOD bit to divide by two */
output(TMOD, 0x20);       /* Select mode 2 for Timer 1 */
output(TH1, SERIAL_RATE); /* set timer 1 reload rate for correct bps */
output(TCON, 0x40);       /* set TR1 to enable Timer 1*/
/* initialize serial transmitter and receiver */
output(SCON, 0x70);       /* select serial mode 1 and enable receiver */
output(SBUF, 0x00);       /* output one byte to set TI */
/* initialize Port 1 */
output(P1,0xFE);          /* initialize port with a/d clock low */
}
/* ------------------------------------------------ */
void output_syringe_data(char s)  /* prints all information form memory
                                     for syringe "s"  */
{
int i;
p = 0;    /* start at beginning */
while (read_XDATA(p) != s)
    {
    p = p + 23;
    if (p > 0x1FF0 ) /* 355 entries */
```

```
            {
            display ('M','E','M','O','R','Y',' ','E','R','R','O','R');
            output_string(mem_err);
            output_char(c[1]);
            output_char(c[2]);
            output_char(LF);
            delay(20000);
            goto EXIT5;
            }
        }
output_string(syrnumstring);
ad_to_ascii(s);
output_char(c[1]);
output_char(c[2]);
output_char(' ');
output_char(' ');
for (i=0;i<8;p_s[i]=read_XDATA(p+2+i),i++);
p_s[i] = '\n';
p_s[i+1] = 0x00;
output_string(p_s);
while (read_XDATA(p) == s)
    {
    print_format(p);
    output_string(p_s);
    p = p + 23;
    if ( p > 0x1FF0 )
        goto EXIT5;
    }
EXIT5: ;
}
/* --------------------------------------------- */
void print_format(int t)  /* formats the memory 32 byte array into
                             the p_s[40] print string
    format: TYPEXXs#NNsMM:SSsPP.PsATMssHH:MM:SS
    or                sPPPsPSI                      */

{
int i;
for (i=0;i<23;i++)
    dt_string[i]=read_XDATA(t+i);
dt=dt_string[1];
switch(dt)
{
case 'I':
case 'D':
case 'T':
    switch(dt_string[1])
        {
        case 'I':
```

```c
            p_s[0]='I';
            p_s[1]='N';
            p_s[2]='F';
            p_s[3]='L';
            p_s[4]='A';
            p_s[5]='T';
            p_s[6]='E';
            break;
    case 'D':
            p_s[0]='D';
            p_s[1]='E';
            p_s[2]='F';
            p_s[3]='L';
            p_s[4]='A';
            p_s[5]='T';
            p_s[6]='E';
            break;
    case 'T':
            p_s[0]='T';
            p_s[1]='e';
            p_s[2]='s';
            p_s[3]='t';
            p_s[4]=' ';
            p_s[5]=' ';
            p_s[6]=' ';
            break;
    }/*end of dt_string[1] switch */
p_s[7] =' ';
p_s[8] ='#';
ad_to_ascii(dt_string[19]);   /* inflation number */
p_s[9] = c[1];
p_s[10] = c[2];
p_s[11] =' ';
etmin = (char)((dt_string[20]*256+dt_string[21])/60);  /* Inf sec */
etsec = (char)((dt_string[20]*256+dt_string[21])%60);
ad_to_ascii(etmin);
p_s[12] = c[1];
p_s[13] = c[2];
ad_to_ascii(etsec);
if(c[1] == ' ')
    c[1] = '0';
p_s[14] =':';
p_s[15] = c[1];
p_s[16] = c[2];
p_s[17] =' ';
pressure=(float)dt_string[22];
    if (dt_string[1]== 'D')
```

```c
    {
    p_s[18] = ' ';
    p_s[19] = ' ';
    p_s[20] = ' ';
    p_s[21] = ' ';
    p_s[22] = ' ';
    p_s[23] = 'N';
    p_s[24] = 'E';
    p_s[25] = 'G';
    }
else
    {
    if ( units == 1)
        {
        ad_to_ascii((char)pressure);
        p_s[18] = c[0];
        p_s[19] = c[1];
        p_s[20] = '.';
        p_s[21] = c[2];
        p_s[22] = ' ';
        p_s[23] = 'A';
        p_s[24] = 'T';
        p_s[25] = 'M';
        }
    else
        {
        p_s[18] = ' ';
        int_to_ascii((int)(pressure * 1.4696));
        switch (c[4])
        {
        case 49 :
                c[4] = 48;
                break;
        case 51 :
                c[4] = 50;
                break;
        case 53 :
                c[4] = 52;
                break;
        case 55 :
                c[4] = 54;
                break;
        case 57 :
                c[4] = 56;
                break;
        }
```

```
                        p_s[19] = c[2];
                        p_s[20] = c[3];
                        p_s[21] = c[4];
                        p_s[22] =' ';
                        p_s[23] ='P';
                        p_s[24] ='S';
                        p_s[25] ='I';
                    }
            }
        break;  /* end of case IP switch */
    case 'R' :
            p_s[0]='R';
            p_s[1]='e';
            p_s[2]='a';
            p_s[3]='d';
            p_s[4]='y';
            for(i=0;i<21;p_s[5+i]=' ',i++);
            break;
    case 'N' :
            p_s[0]='N';
            p_s[1]='e';
            p_s[2]='w';
            p_s[3]=' ';
            p_s[4]='S';
            p_s[5]='y';
            p_s[6]='r';
            p_s[7]='i';
            p_s[8]='n';
            p_s[9]='g';
            p_s[10]='e';
            p_s[11]=' ';
            p_s[12]=' ';
            p_s[13]=' ';
            for(i=0;i<12;p_s[14+i]=' ',i++);
            break;
    case 'Z' :
            p_s[0]='Z';
            p_s[1]='e';
            p_s[2]='r';
            p_s[3]='o';
            p_s[4]=' ';
            p_s[5]='S';
            p_s[6]='y';
            p_s[7]='r';
            p_s[8]='i';
            p_s[9]='n';
            p_s[10]='g';
            p_s[11]='e';
```

```c
            p_s[12]=' ';
            p_s[13]=' ';
            for(i=0;i<12;p_s[14+i]=' ',i++);
            break;
case 'X' :
            p_s[0]='D';
            p_s[1]='i';
            p_s[2]='s';
            p_s[3]='c';
            p_s[4]='o';
            p_s[5]='n';
            p_s[6]='n';
            p_s[7]='e';
            p_s[8]='c';
            p_s[9]='t';
            p_s[10]=' ';
            p_s[11]=' ';
            p_s[12]=' ';
            p_s[13]=' ';
            for(i=0;i<12;p_s[14+i]=' ',i++);
            break;
} /* end of dt switch */
p_s[26] = ' ';
p_s[27] = ' ';
for (i=0;i<8;p_s[28+i]=dt_string[11+i],i++);
p_s[36] = '\n';
p_s[37] = 0x00;
}
/* ---------------------------------------------- */
void main()   /* Main Inteliflator Program */

{
int i;
display(' ',' ',' ',' ',' ',' ',' ',' ',' ',' ',' ',' ');
delay(3000);  /* stabilization delay */
initialize();
display('I','N','T','E','L','L','I','F','L','A','T','R');
delay(20000); /* turn on stabilization delay */
if ( (menu_switch == 0) && (set_switch == 0 ))
     test_out();
display(ver[0],ver[1],ver[2],ver[3],ver[4],ver[5],ver[6],ver[7],ver[8],ver[9],ver[10],ver[11]);

RESTART:

delay(15000); /* more stabilization delay */
```

```
units = 1;
max_pres = 100.0;
swatch_read();
raw_d_t[4] = (raw_d_t[4] & 0xDF); /* turn on osc of swatch */
swatch_write();
zero_pres =0;
roll_dot();
stabilization();
display('A','U','T','O','-','Z','E','R','O','I','N','G');

#ifdef host_debug
zero_pres = 20;
#else
for(i=0;i<1000;zero_pres = (zero_pres + (float)read_ad(pres)),i++);
zero_pres = zero_pres/1000;
                    /* auto_zero avg of one thousand readings */
store_memory_string('Z',0);
#endif
start_period();
inf_nmbr = 0;
etsec = 0;
etmin =0;
pflag=0;
first=0;
hist_flag = 0;

while(TRUE)
    {
    pressure = 0;
get_pressure();
if (pressure < 0)
    hist_flag = 0;
if (read_ad(nleg) >= no_syringe)
    {
    if(pflag)
        store_memory_string('I',pres_high);
    else
        store_memory_string('D',0);
    store_memory_string('X',0);
    do
        {
        display('S','Y','R','I','N','G','E',' ',' ',' ',' ',' ');
        delay(2000);
        display('D','I','S','C','O','N','N','E','C','T','E','D');
        delay(2000);
        display('P','R','E','S','S',' ','-','M','E','N','U','-');
        delay(4000);
        }while (menu_switch == 1);
```

```
          goto RESTART;
          }
if ((pressure > 7) || (hist_flag))
          {
          if (! pflag)
                    {
                    if (first == 0)
                              store_memory_string('R',0);
                    else
                              store_memory_string('D',0);
                    etsec = 0 ;
                    etmin = 0;
                    start_period();
                    pres_high = 0;
                    inf_nmbr++;
                    first =1;
                    hist_flag++;
                    pflag++;
                    }
          ad_to_ascii(inf_nmbr);
          d[0]=c[1];
          d[1]=c[2];
          ad_to_ascii(etmin);
          d[2] = ' ';
          d[3] = c[2];
          d[4] = ':';
          ad_to_ascii(etsec);
          d[5] =c[1];
          if ( d[5] ==' ')
                    d[5] = '0';
          d[6] = c[2];
          d[7] = ' ';
          if ( units == 1)
                    {
                    int_to_ascii((int)pressure);
                    d[8] = c[2];
                    d[9] = c[3];
                    d[10] = '.';
                    d[11] = c[4];
                    }
          else
                    {
                    d[8] = ' ';
                    int_to_ascii((int)(pressure * 1.4696));
                    switch (c[4])
                    {
                    case 49 :
                              c[4] = 48;
```

```
                    break;
        case 51 :
                c[4] = 50;
                break;
        case 53 :
                c[4] = 52;
                break;
        case 55 :
                c[4] = 54;
                break;
        case 57 :
                c[4] = 56;
                break;
        } d[9] = c[2];
        d[10] = c[3];
        d[11] = c[4];
        } display(d[0],d[1],d[2],d[3],d[4],d[5],d[6],d[7],d[8],d[9],d[10],d[11]);
delay(1600);
if (pressure > max_pres)
    display(' ',' ',' ',' ',' ',' ',' ',' ',' ',' ',' ',' ');
delay(800);
swatch_read();
infsec = (int)(swatch_to_seconds() - period_begin);
etmin = (char)(infsec/60);
etsec = (char)(infsec % 60);
if(pres_high < (char)pressure)
    pres_high = (char)pressure;
}
else
    {
    if (pflag)
        {
        store_memory_string('I',pres_high);
        etmin =0;
        etsec = 0;
        pflag = 0;
        start_period();
        }
    ad_to_ascii(inf_nmbr);
    d[0]=c[1];
    d[1]=c[2];
    ad_to_ascii(etmin);
    d[3]=c[1];
    if(d[3] == ' ')
```

```
                d[3] = '0';
            d[4]=c[2];
            ad_to_ascii(etsec);
            d[6]=c[1];
            if(d[6] == ' ')
                d[6] = '0';
            d[7]=c[2];
            if (first == 0)
                {
                swatch_read();
                time_convert();
                display(d[0],d[1],d[2],d[3],d[4],' ',' ','R','E','A','D','Y');
                }
            else
                {
                if (pressure < 0 )
                    display(d[0],d[1],' ',d[3],d[4],':',d[6],d[7],' ','N','E','G');
                else
                    display(d[0],d[1],' ',d[3],d[4],':',d[6],d[7],' ',' ',' ','0');
                delay(2400);
                swatch_read();
                infsec = (int)(swatch_to_seconds() - period_begin);
                etmin = (char) (infsec/60);
                etsec = (char) (infsec % 60);
                }
            if (menu_switch == 0 )
                menu();
            }
        }
} /* end of main */

/* IFCODE2.C Second module of the Intelliflator code */ include <io51.h>   /* required for bit_set, read_X */
define TRUE 1
define FALSE 0
#define LF 10   /* ASCII Line feed */
#define pres '0'    /* ch 0 on a/d for pressure */
#define bat '3'         /* ch 3 on a/d for Battery voltage */
#define nleg '1'    /* ch 1 on a/d for negative transducer leg */
#define pleg '2'    /* ch 2 on a/d for positive transducer leg */
#define swatch 0x1FFF /* swatch scratch address */
#define menu_switch read_bit(P1_6_bit)
#define set_switch read_bit(P1_7_bit)
define no_syringe 100 /* the a/d of nleg above which is no syringe plugged in */ const char pattern[8] = {0xC5,0x3A,0xA3,0x5C,0xC5,0x3A,0xA3,0x5C};
```

```c
extern char raw_d_t[8]; /* raw date and time from/to swatch */
extern char c[5];    /* five ascii characters */
extern float pressure;  /* syringe pressure */
extern float zero_pres; /* syringe reading for zero pressure */
extern char d[12]; /* display character array */
extern char inf_nmbr;
extern char units;
extern float max_pres;
extern char dt;

extern void display();
extern void store_memory_string(char typ,char p);
extern void date_convert();
extern void time_convert();
extern void scroll_data();
extern void digit_set(char n);

void dt_read();
void menu();
void delay(int d);
void int_to_ascii(int n);
void swatch_attn();
void swatch_read();
void swatch_write();
void ad_to_ascii(char n);
void get_pressure();
void output_char(char c);
void output_string(char * msg);
void clear_data();
char read_ad(char n);

/* ------------------------------------------------- */
void menu() /* menu handler */

{
int i;
if (zero_pres != 0 )   /* skip this section if a syrings isnt plugged in */
    {
    do
    {
    display('M','A','R','K',' ','A','S',' ','T','E','S','T');
    delay(1000);
    }while ( menu_switch == 0 );

do     /* mark last inflation as "test" */
        {
        if ( set_switch == 0 )
            {
```

```
                    store_memory_string('T',0);
/*                  if(inf_nmbr != 0)
                        inf_nmbr--;
*/
#ifdef host_debug
                    printf("test inflation\n");
#endif
                    goto EXITMENU;  /* bypass rest of menu if only test marking */
                    }
        get_pressure();
        if ( pressure > 7 )
            goto EXITMENU;
        }while ( menu_switch == 1 );
        } /* if zero_pres */
        do
        {
        }while (menu_switch == 0 );

/* _._._._._._._._._._._._._._._._._._._._._._ */ do      /* scroll through stored data */
            {
            display('S','C','R','O','L','L',' ',' ','D','A','T','A','?');
            if ( set_switch == 0 )
                {
                scroll_data();  /* scroll data past display one line per P1_7 push in reverse order */
                goto EXITMENU;
                }
            if ( zero_pres != 0 )
                {
                get_pressure();
                if ( pressure > 7 )
                goto EXITMENU;
                }

}while ( menu_switch == 1 );
        delay(1000);
        do
        {
        }while (menu_switch == 0 );

/* _._._._._._._._._._._._._._._._._._._._._._ */
        if (zero_pres == 0 )
            {
        do      /* clear the stored inflation data */
            {
            display('C','L','E','A','R',' ','D','A','T','A',' ','?');
            if ( set_switch == 0 )
```

```c
            {
                display('A','R','E',' ',' ','Y','O','U',' ',' ','S','U','R','E');
                do
                    {
                    }while (set_switch == 0 );
                delay(1000);
                do
                    {
                        if ( set_switch == 0 )
                            {
                            display('D','A','T','A',' ',' ','C','L','E','A','R','E','D');
                            clear_data();
                            delay(5000);
                            goto EXITMENU;
                            }
                    }while (menu_switch == 1 );
                goto EXIT2;
                }
            }while ( menu_switch == 1 );
        delay(1000);
        do
            {
            }while (menu_switch == 0 );
        } /* zero_pres */
EXIT2:
/* _ _ _ _ _ _ _ _ _ _ _ _ _ _ _ _ _ _ _ _ _ _ _ _ _ _ _ _ _ _ _ _ _ */
if (zero_pres != 0 )  /* don't do if no syringe */
    {
    do   /* re-zero syringe */
        {
        display('Z','E','R','O',' ',' ','S','Y','R','I','N','G','E');
        if (set_switch == 0 )
            {
            display('A','R','E',' ',' ','Y','O','U',' ',' ','S','U','R','E');
            do
                {
                }while (set_switch == 0 );
            delay(1000);
            do
                {
                if (set_switch == 0 )
                    {
                    display('Z','E','R','O','I','N','G',' ',' ',' ',' ',' ',' ');
                    zero_pres = 0;
                    for(i=0;i<1000;zero_pres = (zero_pres + (float)read_ad(pres)),i++);
                    zero_pres = zero_pres/1000;
                    /* auto_zero avg of one thousand readings */
```

```
                    store_memory_string('Z',0);
                    do
                        {
                        }while (set_switch == 0 );
                    goto EXITMENU;
                    }
                }while (menu_switch == 1);
            goto EXIT3;
            }
        get_pressure();
        if ( pressure > 7 )
            goto EXITMENU;
        }while (menu_switch == 1 );
    } /* if not zero */
EXIT3:
/* -_-_-_-_-_-_-_-_-_-_-_-_-_-_-_-_-_-_-_- */
    do      /* set the maximum pressure limit */
        {
        if (units == 1)
            {
            int_to_ascii((int)max_pres);
            display('M','A','X','(','A','T','M',')',c[2],c[3],'.',c[4]);
            }
        else
            {
            int_to_ascii((int)(max_pres * 1.4696));
            if (c[4] > 52)
                {
                c[3]++;
                if (c[3] > 57 )
                    {
                    c[2]++;
                    if ( c[2] < 48 )
                        c[2] = 49;
                    c[3] = 48;
                    }
                }
            c[4] = 48;
            display('M','A','X','(','P','S','I',')',' ',c[2],c[3],c[4]);
            }
        do
            {
            }while (set_switch == 0 );
        delay(500);
        if ( set_switch == 0 )
            {
            max_pres = max_pres + 5;
```

```c
            if (max_pres > 200 )
                max_pres = 10;
            }
        if ( zero_pres != 0 )
            {
            get_pressure();
            if ( pressure > 7 )
            goto EXITMENU;
            }
        }while ( menu_switch == 1 );
    do
    {
    }while (menu_switch == 0 );
/* -_-_-_-_-_-_-_-_-_-_-_-_-_-_-_-_ */
if (zero_pres == 0)
    {
    do      /* set new time into swatch */
        {
        swatch_read();
        time_convert();
        display(d[0],d[1],d[2],d[3],d[4],d[5],d[6],d[7],' ','0','K','?');
        if( set_switch == 0 )
            {
                dt = 0; /* set time mode */
                do
                    {
                    }while (set_switch == 0 );
                delay(1000);
                digit_set(0);
                digit_set(1);
                digit_set(3);
                digit_set(4);
                digit_set(6);
                digit_set(7);
                swatch_read();
                raw_d_t[3] = (((d[0]-48)&0x0F)<<4)|((d[1]-48)&0x0F);
                raw_d_t[2] = (((d[3]-48)&0x0F)<<4)|((d[4]-48)&0x0F);
                raw_d_t[1] = (((d[6]-48)&0x0F)<<4)|((d[7]-48)&0x0F);
                swatch_write();
            }
        }while ( menu_switch == 1 );
    } /* zero_pres */
    do
        {
        }while (menu_switch == 0 );
        delay(1000);
/* -_-_-_-_-_-_-_-_-_-_-_-_-_-_-_-_ */
```

```c
if (zero_pres == 0 )
    {
    do      /* set new date into swatch */
        {
        swatch_read();
        date_convert();
        display(d[0],d[1],d[2],d[3],d[4],d[5],d[6],d[7],' ','O','K','?');
        if( set_switch == 0 )
            {
                dt = 1; /* set date mode */
                do
                    {
                    }while (set_switch == 0 );
                delay(1000);
                digit_set(0);
                digit_set(1);
                digit_set(3);
                digit_set(4);
                digit_set(6);
                digit_set(7);
                swatch_read();
                raw_d_t[6] = (((d[0]-48)&0x0F)<<4)|((d[1]-48)&0x0F);
                raw_d_t[5] = (((d[3]-48)&0x0F)<<4)|((d[4]-48)&0x0F);
                raw_d_t[7] = (((d[6]-48)&0x0F)<<4)|((d[7]-48)&0x0F);
                swatch_write();
            }
        }while ( menu_switch == 1 );
        delay(1000);
    } /* zero_pres */
    do
    {
    }while (menu_switch == 0 );
/* ---------------------------------- */ do      /* set inflation pressure units */
        {
        if(units == 1)
            {
            display(' ','P','R','E','S',' ','=',' ','A','T','M',' ');
            do
            {
            }while ( set_switch == 0 );
            delay(500);
            if ( set_switch == 0 )
                units = 0;
            }
        else
            {
```

```
                display(' ','P','R','E','S',' ','=',' ','P','S','I',' ');
                do
                {
                }while ( set_switch == 0 );
                delay(500);
                if ( set_switch == 0 )
                    units = 1;
                }
            if ( zero_pres != 0 )
                {
                get_pressure();
                if ( pressure > 7 )
                    goto EXITMENU;
                }
            }while ( menu_switch == 1);

do
    {
    }while (menu_switch == 0 );
/* -_-_-_-_-_-_-_-_-_-_-_-_-_-_-_ */
EXITMENU:
    do
    {
    }while (menu_switch == 0 );
    delay(1000);
} /* end of menu */
/* ---------------------------------------------- */
/* ---------------------------------------------- */
void delay(int d)
    {
    int t;
    for(t = 0;t<d;t++);
    }
/* ---------------------------------------------- */
void int_to_ascii(int n)
    {
        if (n/10000 < 1)
            c[0] = ' ';
        else
            {
                c[0] = 48 + (n/10000);
                c[1] = n/10000;
                n=n-(c[1] * 10000);
            }
        if (n/1000 < 1 )
            if ( c[0] == ' ')
                c[1] = ' ';
            else
```

```c
                    c[1] = '0';
        else
            {
                c[1] = 48 + (n/1000);
                c[2] = n/1000;
                n = n-(c[2] * 1000);
            }
        if (n/100 < 1 )
            if ( c[1] == ' ')
                c[2] = ' ';
            else
                c[2] = '0';
        else
            {
                c[2] = 48 + (n/100);
                c[3] = n/100;
                n = n-(c[3] * 100);
            }
        if (n/10 < 1 )
            if ( c[2] == ' ')
                c[3] = ' ';
            else
                c[3] = '0';
        else
            {
                c[3] = 48 + (n/10);
                c[4] = n/10;
                n = n-(c[4] * 10);
            }
        c[4] = 48 + n;
    }
/* ---------------------------------------------- */
void swatch_attn()

{
    int i,j;
    char out;

out = read_XDATA(swatch);   /* dummy read to set chip pointer */
    for(i=0;i<8;i++)
        {
        out = pattern[i];
        for(j=0;j<8;j++)
            {
            write_XDATA(swatch,out);
            out = out >> 1;
            }
        }
```

```c
    }
/* ------------------------------------------------- */ void dt_read()
    {
    char cin,cinr;
    int i,j;

swatch_attn();
    for(i=0;i<8;i++)
        {
        cin =0;
        for(j=0;j<8;j++)
            {
            cinr = read_XDATA(swatch);
            cinr = cinr & 0x01;
            cinr = cinr << j;
            cin = cin | cinr;
            }
        raw_d_t[i] = cin;
        }
    }
/* ------------------------------------------------- */
void swatch_read()
    {
    char t[8];
    int i;
    char OK;

do
        {
        OK = 0;
        dt_read();
        for(i=0;i<8;t[i]=raw_d_t[i],i++);
        dt_read();
        for (i=1;i<8;i++)   /* skip 1/00 sec */
            {
            if (t[i] != raw_d_t[i])
                OK++;
            }
        }while (OK != 0);   /* continue reading swatch till it agrees */

}

/* ------------------------------------------------- */ void swatch_write()

{
```

```c
    char cout;
    int i,j;

swatch_attn();
    for (i=0;i<8;i++)
        {
        cout = raw_d_t[i];
        if(i == 3)
            cout = cout & 0x3F;
        if(i == 4)
            cout = 0x10;
        for(j=0;j<8;j++)
            {
            write_XDATA(swatch,cout);
            cout = cout >> 1;
            }
        }
    }
/* ------------------------------------------------ */
void ad_to_ascii(char n)
{
    if  (n/100 < 1)
        c[0] = ' ';
    else
        {
        c[0] = 48 + (n/100);
        c[1] = n/100;
        n = n - (c[1] * 100);
        }
    if ( n/10 < 1 )
        if ( c[0] == ' ')
            c[1] = ' ';
        else
            c[1] = '0';
    else
        {
        c[1] = 48 + (n/10);
        c[2] = n/10;
        n = n - (c[2] * 10);
        }
    c[2] = 48 + n;
}
/* ------------------------------------------------ */
void get_pressure()   /* reads syringe pressure */

{
int i;
#ifdef host_debug
```

```c
    printf("pressure=");
    pressure = getch();
#else
        for(i=0;i<10;i++)
            pressure = (pressure + (float)read_ad(pres));
#endif
        pressure = pressure/10;
        pressure = pressure - zero_pres;
        if (pressure > 200)
            pressure = 200;
}
/* -------------------------------------------- */
void output_char(char c)  /* output character to serial interface */

{
while ((read_bit(P1_3_bit))||(!read_bit_and_clear(TI_bit)));
        /* wait for CTS and transmit buffer empty */
output(SBUF,c);    /* output character to transmitter */
}
/* -------------------------------------------- */
void output_string(char * msg )  /* output string at pointer to serial interface */

{
while(*msg)
    {
    output_char(*msg++);
    }
}
/* -------------------------------------------- */
void clear_data()  /* clears data memory and resets syr pointer to zero  */
{
int i;
for(i=0;i<0x2000;i++)
    write_XDATA(i,0);
}
/* -------------------------------------------- */
char read_ad(char n)

{
char adout = 0;

#ifdef host_debug
printf("input a/d for %c",n);
adout = getch();
else clear_bit(P1_1_bit);    /* cs low */
    set_bit(P1_2_bit);      /* start bit DI */
```

```c
set_bit(P1_0_bit);       /* clock rise (DI read) */
clear_bit(P1_0_bit);     /* clock fall */
set_bit(P1_2_bit);       /* Single ended measurement */
set_bit(P1_0_bit);       /* DI read */
clear_bit(P1_0_bit);     /* clock fall */
switch(n)
{
case '0' :
    clear_bit(P1_2_bit);    /* O/S = 0 */
    set_bit (P1_0_bit);
    clear_bit(P1_0_bit);
    clear_bit(P1_2_bit);    /* select = 0 */
    set_bit(P1_0_bit);
    clear_bit(P1_0_bit);
    break;
case '1' :
    set_bit(P1_2_bit);      /* O/S = 1 */
    set_bit (P1_0_bit);
    clear_bit(P1_0_bit);
    clear_bit(P1_2_bit);    /* select = 0 */
    set_bit(P1_0_bit);
    clear_bit(P1_0_bit);
    break;
case '2' :
    clear_bit(P1_2_bit);    /* O/S = 0 */
    set_bit (P1_0_bit);
    clear_bit(P1_0_bit);
    set_bit(P1_2_bit);      /* select = 1 */
    set_bit(P1_0_bit);
    clear_bit(P1_0_bit);
    break;
case '3' :
    set_bit(P1_2_bit);      /* O/S = 1 */
    set_bit (P1_0_bit);
    clear_bit(P1_0_bit);
    set_bit(P1_2_bit);      /* select = 1 */
    set_bit(P1_0_bit);
    clear_bit(P1_0_bit);
    break;
}
set_bit(P1_2_bit);          /* set up port for input */
set_bit(P1_0_bit);          /* dummy rear for A/D */
clear_bit(P1_0_bit);
set_bit(P1_0_bit);
if ( read_bit(P1_2_bit))
    adout = adout + 128;
clear_bit(P1_0_bit);
set_bit(P1_0_bit);
```

```
    if ( read_bit(P1_2_bit))
        adout = adout + 64;
    clear_bit(P1_0_bit);
    set_bit(P1_0_bit);
    if ( read_bit(P1_2_bit))
        adout = adout + 32;
    clear_bit(P1_0_bit);
    set_bit(P1_0_bit);
    if ( read_bit(P1_2_bit))
        adout = adout + 16;
    clear_bit(P1_0_bit);
    set_bit(P1_0_bit);
    if ( read_bit(P1_2_bit))
        adout = adout + 8;
    clear_bit(P1_0_bit);
    set_bit(P1_0_bit);
    if ( read_bit(P1_2_bit))
        adout = adout + 4;
    clear_bit(P1_0_bit);
    set_bit(P1_0_bit);
    if ( read_bit(P1_2_bit))
        adout = adout + 2;
    clear_bit(P1_0_bit);
    set_bit(P1_0_bit);
    if ( read_bit(P1_2_bit))
        adout = adout + 1;
        clear_bit(P1_0_bit);
    set_bit(P1_1_bit);              /* de-select */
#endif
    return adout;
}
```

APPENDIX B

COPYRIGHT 1990-1991 by Merit Medical Systems, Inc.

PROGRAM: MONARCH
Version:    1.0

```
NAME Monarch

VENT0   MBE=1, RBE=0, MAIN      ; SET UP THE MAIN ROUTINE.
     VENT1   MBE=1, RBE=0, INTERRUPT ; SET UP THE MAIN INTERRUPT ROUTINE.

AD_VALUE MACRO CHANNEL,VARIABLE
     GETI SEL15              ; SELECT A NEW MEMORY BANK.
     X = #CHANNEL             ; LOAD THE CHANNEL NUMBER.
     A = #08H                 ; SEE PAGE 5-164.
     ADM = XA                 ; SELECT CHANNEL AND BEGIN THE A/D CONVERSION.
     NOP                      ; WAIT AT LEAST 4 MACHINE CYCLES...
```

```
        NOP                     ; ...BEFORE TESTING EOC...
        NOP                     ; ...(SEE PAGE 5-167 OF USERS MANUAL).
        NOP
        NOP
        REPEAT
        UNTIL_BIT(EOC)          ; WAIT UNTIL EOC IS SET.
        XA = SA                 ; GET THE A/D VALUE FROM THE CONVERSION REGISTER.
        GETI SEL0
        VARIABLE = XA           ; SAVE THE A/D VALUE IN THE SPECIFIED VARIABLE.
        ENDM

DISPLAY MACRO VALUE,DIGIT,TABLE
        PUSH HL                 ; SAVE HL AND XA.
        PUSH XA
        HL = #DIGIT             ; POINT TO THE DIGIT.
        X = #TABLE              ; GET THE TABLE NUMBER (0 OR 2).
        A = VALUE               ; GET THE VALUE (0 TO F).
        CALL !WRT_DGT           ; EXECUTE THE TABLE LOOK-UP, WRITE THE DIGIT.
        POP XA                  ; RESTORE XA AND HL.
        POP HL
        ENDM

DMP_REG4 MACRO REGISTER
        GETI SEL15              ; SELECT A NEW MEMORY BANK.
        A = REGISTER            ; MOVE THE VALUE OF THE REGISTER INTO XA.
        X = #00H                ; BLANK OUT X.
        GETI SEL0               ; SELECT A NEW MEMORY BANK.
        HL = #00H               ; POINT TO XA.
        CALL !DUMP_BYTE         ; SEND THE VALUE TO THE PC.
        ENDM

DMP_REG8 MACRO REGISTER
        GETI SEL15              ; SELECT A NEW MEMORY BANK.
        XA = REGISTER           ; MOVE THE VALUE OF THE REGISTER INTO XA.
        GETI SEL0               ; SELECT A NEW MEMORY BANK.
        HL = #00H               ; POINT TO XA.
        CALL !DUMP_BYTE         ; SEND THE VALUE TO THE PC.
        ENDM

RES_ACMLTR MACRO
        GETI SEL0               ; SELECT A NEW MEMORY BANK.
        POP XA
        MOV ASWORK+2,XA
        POP XA
        MOV ASWORK,XA
        POP XA
        MOV ACMLTR+2,XA
        POP XA
        MOV ACMLTR,XA
        POP HL
        POP DE
        POP BC
        POP XA
        ENDM

SAV_ACMLTR MACRO
        GETI SEL0               ; SELECT A NEW MEMORY BANK.
        PUSH XA
        PUSH BC
        PUSH DE
        PUSH HL
        MOV XA, ACMLTR
        PUSH XA
        MOV XA, ACMLTR+2
        PUSH XA
        MOV XA, ASWORK
```

```
        PUSH XA
        MOV XA, ASWORK+2
        PUSH XA
        ENDM

SBTRCT8 MACRO OP1,OP2
        ACMLTR = OP1 (XA)           ; OP1 AND OP2 ARE ONLY 8 BITS.
        ASWORK = OP2 (XA)
        XA = #00H
        ACMLTR+2 = XA               ; BLANK OUT THE HIGH 8 BITS.
        ASWORK+2 = XA
        CALL !SUB16                 ; COMPUTE OP1-OP2. SET CY IF LESS THAN ZERO.
        ENDM

SBTRCT16 MACRO OP1,OP2
        ACMLTR = OP1 (XA)           ; OP1 AND OP2 ARE 16 BIT VARIABLES.
        ASWORK = OP2 (XA)
        ACMLTR+2 = OP1+2 (XA)
        ASWORK+2 = OP2+2 (XA)
        CALL !SUB16                 ; COMPUTE OP1-OP2. SET CY IF LESS THAN ZERO.
        ENDM

REGSEG      DSEG 0 AT 0H    ; DEFINE THE REGISTER SEGMENT.
RGSTRS:     DS 08H          ; ALLOCATE 8 NIBBLES OF MEMORY FOR REGISTERS.
FLGSEG0     DSEG 0 AT 08H   ; DEFINE A SEGMENT FOR USER DEFINED FLAGS.
FLAG0:      DS 5H           ; ALLOCATE AREA FOR FLAGS IN MEMORY BANK 0.
A2D_S       EQU 08H.0       ; THIS FLAG IS SET IF A2D > A2D_L.
BTN1        EQU 08H.1       ; CURRENT BUTTON STATUS.
BTN2        EQU 08H.2       ; LAST STATUS OF THE BUTTON.
BTN3        EQU 08H.3       ;
CMPT_FOFST  EQU 09H.0       ; FLAG INDICATING THAT THE FINAL OFFSET IS TO BE COMPUTED.
ERR_BIT     EQU 09H.1       ; FLAG USED TO SHOW STATUS OF VARIOUS ERRORS.
INFLATING   EQU 09H.2       ; FLAG INDICATING THAT AN INFLATION IS IN PROGRESS.
INTRPTD     EQU 09H.3       ; FLAG INDICATING THAT THERE HAS BEEN AN INTERRUPT.
LED_ENBL    EQU 0AH.0       ; LED ENABLE FLAG.
LED_ON      EQU 0AH.1       ; FLAG INDICATING THAT THE LEDs ARE ON.
MAX_ON      EQU 0AH.2       ; FLAG INDICATING THAT THE MAXIMUM ANNUNCIATOR SHOULD BE SET.
MIN_ON      EQU 0AH.3       ; FLAG INDICATING THAT THE MINIMUM ANNUNCIATOR SHOULD BE SET.
NEG_PRES    EQU 0BH.0       ; FLAG INDICATING THAT THE PRESSURE IS LESS THAN 0.
NEW_PRES    EQU 0BH.1       ; FLAG INDICATING IF A NEW PRESSURE HAS BEEN COMPUTED (USED IN FOFFSET).
PSI         EQU 0BH.2       ; DISPLAY IN PSI?
STANDBY     EQU 0BH.3       ; STANDBY ENABLE FLAG.
TRM_ENBL    EQU 0CH.0       ; FLAG INDICATING THAT THE ERROR ROUTINE IS ENABLED.
Z_FLAG      EQU 0CH.1       ; FLAG INDICATING THAT THE ABS(PRSR) <= ZWINDOW (.1 ATM).

VRBLS       DSEG 0 AT 10H   ; DEFINE A SEGMENT FOR VARIABLES.
DIVDA:      DS 4H           ; DEFINE WORK AREA FOR DIVISION.
DIVDB:      DS 4H           ; DEFINE WORK AREA FOR DIVISION.
DIVDC:      DS 4H           ; DEFINE WORK AREA FOR DIVISION.
MULTC:      DS 4H           ; DEFINE WORK AREA FOR MULTIPLICATION.
MULTB:      DS 4H           ; DEFINE WORK AREA FOR MULTIPLICATION.
MULTA:      DS 4H           ; DEFINE WORK AREA FOR MULTIPLICATION.
ACMLTR:     DS 4H           ; DEFINE WORK AREA FOR ADDITION/SUBTRACTION.
ASWORK:     DS 4H           ; DEFINE WORK AREA FOR ADDITION/SUBTRACTION.
A1:         DS 4H           ;
A2:         DS 4H           ;            ┌ (A1/256)*A2D+C1+OFFSET, FOR A2D <= CH_MODEL
C1:         DS 4H           ; PRESSURE = ┤
C2:         DS 4H           ;            └ (A2/256)*A2D+C2+OFFSET, FOR A2D > CH_MODEL
OFFSET:     DS 4H           ;
GEL:        DS 4H           ; SEE 'FOFFSET' ROUTINE FOR COMPUTATION AND UTILIZATION OF 'OFFSET' AND 'GEL'.
BGN_INFL:   DS 4H           ; PRESSURE THRESHOLD FOR BEGINNING AN INFLATION.
DSPL_MAX:   DS 4H           ; THE MAXIMUM PRESSURE WHICH MAY BE DISPLAYED.
DSPL_MIN:   DS 4H           ; THE MINIMUM PRESSURE WHICH MAY BE DISPLAYED.
END_INFL:   DS 4H           ; PRESSURE THRESHOLD FOR ENDING AN INFLATION
PRSR:       DS 4H           ; THE CURRENT PRESSURE VALUE (UNITS ARE .1 ATM, FORMAT IS BINARY).
PRSR_M:     DS 4H           ; THE MAXIMUM PRESSURE OF THE CURRENT INFLATION.
A2D:        DS 2H           ; CURRENT A/D RESULT.
A2D_L:      DS 2H           ; THE LAST A/D RESULT
A2D_MAX:    DS 2H           ; THE A/D THRESHOLD VALUE WHICH WILL TRIGGER THE MAXIMUM PRESSURE ANNUNCIATOR.
```

```
A2D_MIN:        DS 2H       ; THE A/D THRESHOLD VALUE WHICH WILL TRIGGER THE MINIMUM PRESSURE ANNUNCIATOR.
BSP_CNTR:       DS 2H       ; THE BUTTON IS CHECKED WHEN BSP_CNTR >= BSP_VAL.
BSP_VAL:        DS 2H       ; THE BUTTON SAMPLE FREQ.  f = 1/(.00195*BSP_VAL) Hz.
CH_MODEL:       DS 2H       ; THE A/D VALUE WHICH DEFINES THE BOUNDARY BETWEEN TWO LINEAR MODELS.
EROT_TMR:       DS 2H       ; USED AS A TIMEOUT TIMER IN THE ERROR ROUTINE.
ERR:            DS 2H       ; THE ERROR NUMBER
EXCTN:          DS 2H       ; THE EXCITATION VOLTAGE OF THE A/D.
EXTN_MIN:       DS 2H       ; THE LOWEST EXCITATION VOLTAGE ALLOWED.
LDOT_VAL:       DS 2H       ; LED POWER-DOWN VALUE: UNITS ARE MINUTES.
LED_CNTR:       DS 2H       ; THE LED IS TURNED ON WHEN LED_CNTR >= LED_VAL.
LED_VAL:        DS 2H       ; THIS DEFINES THE LED FREQ.  f = 1/(.00195*LED_VAL) Hz.
NLEG:           DS 2H       ; NLEG VALUE.
NLEG_MAX:       DS 2H       ; THE GREATEST NLEG VOLTAGE ALLOWED.
NLEG_MIN:       DS 2H       ; THE SMALLEST NLEG VOLTAGE ALLOWED.
PLEG:           DS 2H       ; PLEG VALUE.
PLEG_MAX:       DS 2H       ; THE GREATEST PLEG VOLTAGE ALLOWED.
PLEG_MIN:       DS 2H       ; THE SMALLEST PLEG VOLTAGE ALLOWED.
PRSR_CNTR:      DS 2H       ; PRESSURE IS SAMPLED AND DISPLAYED WHEN PRSR_CNTR >= PRSR_VAL
PRSR_VAL:       DS 2H       ; THIS DEFINES THE PRESSURE FREQ.  f = 1/(.00195*PRSR_VAL) Hz.
RZWINDOW:       DS 2H       ; THIS IS THE RE-ZERO WINDOW.
SAV_BS:         DS 2H       ; BACKUP FOR MEMORY BANK SELECT REGISTER.
SAV_HL:         DS 2H       ; BACKUP FOR REGISTER HL.
SAV_SIO:        DS 2H       ; BACKUP FOR THE SHIFT REGISTER.
SAV_XA:         DS 2H       ; BACKUP FOR REGISTER XA.
TMOT_TMR:       DS 2H       ; TIME-OUT TIMER: UNITS ARE MINUTES.
TMOT_VAL:       DS 2H       ; TIME-OUT VALUE: UNITS ARE MINUTES.
WTCH_DOG:       DS 2H       ; WATCH DOG COUNTER.
ZWINDOW:        DS 2H       ; THIS IS THE ZERO WINDOW VALUE.
BAND_VAL:       DS 1H       ; THE 'BANDING' VALUE.
BTN_CNTR:       DS 1H       ; THIS STORES THE NUMBER OF TIMES THE BUTTON HAS BEEN PUSHED.
BTN_VAL:        DS 1H       ; IF BTN_CNTR >= BTN_VAL, THE CHIP IS POWERED DOWN.
ERRCNT:         DS 1H       ; SERIAL DATA TRANSFER ERROR COUNTER.

DSP_VAR         DSEG 1 AT 10
BCD_WRK:        DS 3H       ; DEFINE AREA FOR BINARY-TO-DECIMAL CONVERSION.
                            ; THESE THREE NIBBLES MUST BE ON THE SAME MEMORY ROW.
P0_DSPL:        DS 1H       ; CURRENT PRESSURE: ATM OR PSI, TENTHS DIGIT.
P1_DSPL:        DS 1H       ; CURRENT PRESSURE: ATM OR PSI, ONES DIGIT.
P2_DSPL:        DS 1H       ; CURRENT PRESSURE: ATM OR PSI, TENS DIGIT.
P0_LAST:        DS 1H       ; LAST PRESSURE: ATM OR PSI, TENTHS DIGIT.
P1_LAST:        DS 1H       ; LAST PRESSURE: ATM OR PSI, ONES DIGIT.
P2_LAST:        DS 1H       ; LAST PRESSURE: ATM OR PSI, TENS DIGIT.
T0_DSPL:        DS 1H       ; CURRENT TIME: MINUTES, ONES DIGIT.
T1_DSPL:        DS 1H       ; CURRENT TIME: MINUTES, TENS DIGIT.
T2_DSPL:        DS 1H       ; CURRENT TIME: SECONDS, ONES DIGIT.
T3_DSPL:        DS 1H       ; CURRENT TIME: SECONDS, TENS DIGIT.
T0_LAST:        DS 1H       ; LAST TIME: MINUTES, ONES DIGIT.
T1_LAST:        DS 1H       ; LAST TIME: MINUTES, TENS DIGIT.
T2_LAST:        DS 1H       ; LAST TIME: SECONDS, ONES DIGIT.
T3_LAST:        DS 1H       ; LAST TIME: SECONDS, TENS DIGIT.
TWO_1:          DS 1H       ; DEFINE VARIABLES FOR COMPARISON...
FIVE_1:         DS 1H       ; ...AND MATH OPERATIONS (IN BANK 1).
SIX_1:          DS 1H
TEN_1:          DS 1H
BACKUP          DSEG 1 AT 0D0H
CNSTNTS:        DS 1AH
FLGSEG1         DSEG 1 AT 0EAH
FLAG1:          DS 2H       ; ALLOCATE AREA FOR FLAGS IN MEMORY BANK 1.
HALF_SEC        EQU 01EAH.0 ; FLAG FOR HALF SECOND COUNTS.
DIGITS          DSEG 1 AT 0ECH
DIGIT7:         DS 3H
DIGIT6:         DS 3H
DIGIT5:         DS 3H
DIGIT4:         DS 3H
DIGIT3:         DS 3H
DIGIT2:         DS 3H
DIGIT1:         DS 2H
COLON           EQU 1F2H.2
MAX             EQU 1FFH.2
MIN             EQU 1FFH.1
DECIMAL         EQU 1FBH.2
L_INFLTN        EQU 1F7H.0
```

```
CSEGI CSEG IENT
POPMB:  POP BS              ; RESTORE THE MEMORY BANK.
PUSHMB: PUSH BS             ; SAVE THE MEMORY BANK.
SEL0:   SEL MB0             ; SELECT MEMORY BANK 0
SEL1:   SEL MB1             ; SELECT MEMORY BANK 1
SEL15:  SEL MB15            ; SELECT MEMORY BANK 15

MAIN CSEG XBLOCKA
        GOTO INIT_RAM
        RAM_RET:
        CALL !INIT_VAR      ; INITIALIZE VARIABLES AND CONSTANTS.
        CALL !INIT_CLK      ; INITIALIZE CLOCKS AND TIMERS.
        CALL !INIT_PRT      ; INITIALIZE PORTS.
        CALL !INIT_LCD      ; INITIALIZE THE LCD CONTROLS.
        CALL !TRNDCR_CHK    ; IF VALID TRANSDUCER NOT DETECTED, STANDBY UNTIL
                            ; ...BUTTON PUSHED AND VALID TRANSDUCER CONNECTED.
        EI                  ; ENABLE THE MASTER INTERRUPT FLAG (ENABLE ALL INTERRUPTS).
        EI IEW              ; ENABLE THE WATCH TIMER INTERRUPT (EVERY 0.5 SECONDS).
        EI IEBT             ; ENABLE THE BASIC INTERRUPT TIMER.
        WHILE(FOREVER)
           WTCH_DOG = #00H (XA) ; CLEAR THE WATCHDOG VARIABLE.
           CALL !SHUTDOWN   ; PLACE SYSTEM IN STANDBY?.
           CALL !CALIBRATE  ; CALIBRATE?
           CALL !TMR_INC    ; SERVICE THE INFLATION DISPLAY CLOCK.
           CALL !BTN_CNT    ; COUNT THE NUMBER OF TIMES THE BUTTON IS PUSHED.
           CALL !PRESSURE   ; UPDATE PRESSURE.
        ENDW

BAND CSEG XBLOCKA

GETI PUSHMB         ; SAVE THE MEMORY BANK
        GETI SEL0           ; SELECT A NEW MEMORY BANK.
        SBTRCT8 A2D_L, A2D  ; COMPUTE A2D_L - A2D
        IF_BIT(!CY)         ; IF RESULT IS NOT NEGATIVE...
           CALL !TWOS_CMP   ; ...GET THE NEGATIVE VALUE.
           CLR1 A2D_S       ; ...INDICATE THAT A2D <= A2D_L.
        ELSE                ; ELSE
           SET1 A2D_S       ; ...INDICATE THAT A2D > A2D_L.
        ENDIF
        XA = #00H           ; INITIALIZE THE HIGH BYTE OF ASWORK
        ASWORK+2 = XA
        A = BAND_VAL        ; LOAD THE LOW BYTE OF ASWORK WITH BAND_VAL.
        ASWORK = XA
        CALL !ADD16         ; ADD BAND_VAL AND -ABS(A2D_L-A2D).
        IF_BIT(CY)          ; IF BAND_VAL - ABS(A2D_L-A2D) < 0...
           SET1 LED_ENBL    ; ...ENABLE THE LEDs (THE LEDs MAY ALREADY BE ENABLED).
           TMOT_TMR = #00H (XA) ; ...RESET THE TIME-OUT TIMER.
           ACMLTR = A2D (XA) ; ...UPDATE A2D_L BY USING THE...
           ASWORK = BAND_VAL (A) ; ...BANDING-CHAIN METHOD. THIS CAN BE...
           XA = #00H        ; ...UNDERSTOOD BY VISUALIZING THE VALUES...
           ACMLTR+2 = XA    ; ...'A2D' AND 'A2D_L' AS BEING CONNECTED BY...
           ASWORK+1 = A     ; ...A CHAIN OF LENGTH 'BAND_VAL'. AS 'A2D'...
           ASWORK+2 = XA    ; ...MOVES EITHER UP OR DOWN, 'A2D_L' IS DRAGGED...
           IF_BIT(A2D_S)    ; ...ALONG. THEREFORE, 'A2D_L' WILL ALWAYS EQUAL...
              CALL !SUB16   ; ...A2D ± BAND_VAL. WHETHER IT IS + OR - WILL...
           ELSE             ; ...DEPEND ON WHETHER A2D IS 'DRAGGING' 'A2D_L'...
              CALL !ADD16   ; ...DOWN OR UP.
           ENDIF            ;
           A2D_L = ACMLTR (XA) ; ...UPDATE A2D_L.
        ENDIF
        GETI POPMB          ; RESTORE THE MEMORY BANK
        RET

BTN_CNT CSEG XBLOCKA

GETI PUSHMB         ; SAVE THE MEMORY BANK
        GETI SEL0           ; SELECT A NEW MEMORY BANK.
        SBTRCT8 BSP_CNTR,BSP_VAL
        IF_BIT(CY)          ; IF BSP_CNTR - BSP_VAL < 0...
```

```
            GOTO btn_end          ; ...EXIT THIS ROUTINE.
        ENDIF
        BSP_CNTR = #00H (XA)      ; RESET THE COUNTER.
        IF_BIT(!BTN2)
          CLR1 BTN3
        ELSE
          SET1 BTN3
        ENDIF
        IF_BIT(!BTN1)
          CLR1 BTN2
        ELSE
          SET1 BTN2
        ENDIF
        IF_BIT(!PORT0.0 && !PORT0.0)   ; CHECK FOR SWITCH BOUNCE.
          CLR1 BTN1
        ELSE
          SET1 BTN1
        ENDIF
        IF_BIT(!BTN1 && !BTN2)    ; DETECT FALLING EDGE AND...
          IF_BIT(BTN3 && !PORT0.0) ; ...DETECT SWITCH BOUNCE.
            BTN_CNTR ++            ; ...INCREMENT THE BTN_CNTR.
            NOP
            SET1 LED_ENBL          ; ...ENABLE THE LEDs.
            TMOT_TMR = #00H (XA)   ; ...RESET THE TIME-OUT TIMER.
            CALL !LCD_MAIN         ; ...UPDATE THE LCDs
          ENDIF
        ENDIF
        IF_BIT(BTN1 && BTN2)      ; DETECT RISING EDGE AND...
          IF_BIT(!BTN3 && PORT0.0) ; ...DETECT SWITCH BOUNCE.
            CALL !LCD_MAIN         ; ...UPDATE THE LCDs
          ENDIF
        ENDIF
btn_end:
        GETI POPMB                ; RESTORE THE MEMORY BANK
        RET

CLR_DSPL CSEG XBLOCKA

GETI PUSHMB               ; SAVE THE MEMORY BANK
        GETI SEL1                 ; SELECT A NEW MEMORY BANK.
        XA = #00H
        P0_DSPL = A
        P1_DSPL = A
        P2_DSPL = A
        T0_DSPL = A
        T1_DSPL = A
        T2_DSPL = A
        T3_DSPL = A
        P0_LAST = A
        P1_LAST = A
        P2_LAST = A
        T0_LAST = A
        T1_LAST = A
        T2_LAST = A
        T3_LAST = A
        A = #0000B                ; SET VALUE TO WRITE TO DISPLAY MEMORY.
        CALL !DSPL_INDEX          ; TURN ALL LCD SEGMENTS OFF.
        GETI POPMB                ; RESTORE THE MEMORY BANK
        RET

C_BCKUP CSEG XBLOCKA

GETI PUSHMB               ; SAVE THE MEMORY BANK
        GETI SEL1                 ; SELECT MEMORY BANK 1
        DE = #A1                  ; POINT TO CONSTANT AREA IN MEMORY BANK 0
        HL = #CNSTNTS             ; POINT TO CONSTANT AREA IN MEMORY BANK 1
        REPEAT
          MOV A,@DE               ; GET VALUE FROM MEMORY BANK 0.
          MOV @HL,A               ; BACKUP VALUE IN MEMORY BANK 1.
          L++                     ; INCREMENT L.
          NOP                     ; NOP IN CASE OF SKIP.
          E++                     ; INCREMENT E AND SKIP THE NEXT INSTRUCTION ON CARRY.
```

```
        UNTIL(FOREVER)
        H++                     ; POINT THE NEXT ROWS OF MEMORY.
        NOP
        D++
        NOP
        REPEAT
          MOV A,@DE             ; GET VALUE FROM MEMORY BANK 0.
          MOV @HL,A             ; BACKUP VALUE IN MEMORY BANK 1.
          L++                   ; INCREMENT L.
          NOP                   ; NOP IN CASE OF SKIP.
          E++                   ; INCREMENT E AND SKIP THE NEXT INSTRUCTION ON CARRY.
        UNTIL(L == #0BH)
        GETI POPMB              ; RESTORE THE MEMORY BANK
        RET

C_VRFY CSEG XBLOCKA

GETI PUSHMB             ; SAVE THE MEMORY BANK
        GETI SEL1               ; SELECT MEMORY BANK 1
        DE = #A1                ; POINT TO CONSTANT AREA IN MEMORY BANK 0
        HL = #CNSTNTS           ; POINT TO CONSTANT AREA IN MEMORY BANK 1
        REPEAT
          A = @DE               ; GET VALUE FROM BANK 0
          IF(A != @HL)          ; IF BANK 0 NOT EQUAL TO BANK 1...
            GETI SEL0           ; ...SELECT MEMORY BANK 0
            SET1 TRM_ENBL       ; ...ENABLE PROGRAM TERMINATION...
            ERR = #06H (XA)     ; ...LOAD ERROR CODE...
            CALL !ERROR         ; ...TERMINATE PROGRAM.
          ENDIF
          L++                   ; INCREMENT COLUMN ADDRESS OF BOTH BANKS.
          NOP
          E++                   ; INCREMENT AND SKIP THE NEXT INSTRUCTION IF CARRY RESULTS.
        UNTIL(FOREVER)
        H++                     ; INCREMENT ROW ADDRESS...
        NOP                     ;
        D++                     ;
        NOP                     ; ...OF BOTH BANKS.
        REPEAT
          A = @DE               ; GET VALUE FROM BANK 0
          IF(A != @HL)          ; IF BANK 0 NOT EQUAL TO BANK 1...
            GETI SEL0           ; ...SELECT MEMORY BANK 0
            SET1 TRM_ENBL       ; ...ENABLE PROGRAM TERMINATION...
            ERR = #06H (XA)     ; ...LOAD ERROR CODE...
            CALL !ERROR         ; ...TERMINATE PROGRAM.
          ENDIF
          L++                   ; INCREMENT COLUMN ADDRESS OF BOTH BANKS.
          NOP
          E++                   ; INCREMENT AND SKIP THE NEXT INSTRUCTION IF CARRY RESULTS.
        UNTIL(L == #0BH)
        A = #02D                ; GET THE VALUE.
        HL = #TWO_1             ; POINT TO RAM.
        IF(A != @HL)            ; IF VALUE NOT EQUAL TO RAM...
          GETI SEL0             ; ...SELECT MEMORY BANK 0
          SET1 TRM_ENBL         ; ...ENABLE PROGRAM TERMINATION...
          ERR = #06H (XA)       ; ...LOAD ERROR CODE...
          CALL !ERROR           ; ...TERMINATE PROGRAM.
        ENDIF

A = #05D                ; GET THE VALUE.
        HL = #FIVE_1            ; POINT TO RAM.
        IF(A != @HL)            ; IF VALUE NOT EQUAL TO RAM...
          GETI SEL0             ; ...SELECT MEMORY BANK 0
          SET1 TRM_ENBL         ; ...ENABLE PROGRAM TERMINATION...
          ERR = #06H (XA)       ; ...LOAD ERROR CODE...
          CALL !ERROR           ; ...TERMINATE PROGRAM.
        ENDIF

A = #06D                ; GET THE VALUE.
        HL = #SIX_1             ; POINT TO RAM.
        IF(A != @HL)            ; IF VALUE NOT EQUAL TO RAM...
```

```
        GETI SEL0              ; ...SELECT MEMORY BANK 0
        SET1 TRM_ENBL          ; ...ENABLE PROGRAM TERMINATION...
        ERR = #06H (XA)        ; ...LOAD ERROR CODE...
        CALL !ERROR            ; ...TERMINATE PROGRAM.
    ENDIF

A = #010D                  ; GET THE VALUE.
    HL = #TEN_1                ; POINT TO RAM.
    IF(A != @HL)               ; IF VALUE NOT EQUAL TO RAM...
        GETI SEL0              ; ...SELECT MEMORY BANK 0
        SET1 TRM_ENBL          ; ...ENABLE PROGRAM TERMINATION...
        ERR = #06H (XA)        ; ...LOAD ERROR CODE...
        CALL !ERROR            ; ...TERMINATE PROGRAM.
    ENDIF
    GETI POPMB                 ; RESTORE THE MEMORY BANK
    RET

CLR_TIME CSEG XBLOCKA

GETI PUSHMB                ; SAVE THE MEMORY BANK
    GETI SEL15                 ; SELECT A NEW MEMORY BANK.
    WM = #00H (XA)
    WM = #00000100B (XA)
    GETI SEL1                  ; SELECT A NEW MEMORY BANK.
    A = #00H
    T0_DSPL = A
    T1_DSPL = A
    T2_DSPL = A
    T3_DSPL = A
    GETI POPMB                 ; RESTORE THE MEMORY BANK
    RET

DSPL_INDEX CSEG XBLOCKA

GETI PUSHMB                ; SAVE THE MEMORY BANK
    GETI SEL1                  ; SELECT A NEW MEMORY BANK.

HL = #DIGITS               ; POINT TO THE FIRST LOCATION OF DISPLAY MEMORY.
    REPEAT
        REPEAT
            @HL = A            ; WRITE VALUE IN A TO DISPLAY MEMORY POINTED TO BY HL.
            L++                ; INCREMENT, SKIP THE NEXT INSTRUCTION ON A CARRY.
        UNTIL(FOREVER)
        H++                    ; INCREMENT, SKIP THE NEXT INSTRUCTION ON A CARRY.
    UNTIL(FOREVER)
    GETI POPMB                 ; RESTORE THE MEMORY BANK
    RET

ERROR CSEG XBLOCKA

DI                         ; DISABLE THE MASTER INTERRUPT FLAG.
    GETI PUSHMB                ; SAVE THE MEMORY BANK
    GETI SEL0                  ; SELECT MEMORY A NEW MEMORY BANK.
    SAV_XA = XA                ; SAVE THE XA REGISTER.
    SAV_HL = HL (XA)           ; SAVE THE HL REGISTER.
    POP XA                     ; COPY THE MEMORY BANK REGISTER FROM...
    PUSH XA                    ; ...THE STACK INTO XA...
    SAV_BS = XA                ; ...THEN INTO RAM.
    GETI SEL15                 ; SELECT A NEW MEMORY BANK.
    XA = SIO                   ; COPY THE SHIFT REGISTER INTO XA.
    GETI SEL0                  ; SELECT A NEW MEMORY BANK.
    SAV_SIO = XA               ; COPY THE SHIFT REGISTER INTO RAM.
```

```
      SET1 ERR_BIT
      GETI SEL1                    ; SELECT A NEW MEMORY BANK.
      CLR1 COLON
      CLR1 MAX
      CLR1 MIN
      CLR1 DECIMAL
      CLR1 L_INFLTN
      A = #0000B                   ; BLANK OUT THE LEADING DIGIT.
      DIGIT1+0 = A
      DIGIT1+1 = A

DIGIT2+0 = #0000B (A)        ; WRITE OUT AN 'E'.
      DIGIT2+1 = #0111B (A)
      DIGIT2+2 = #0110B (A)
      DIGIT3+0 = #0000B (A)        ; WRITE OUT AN 'r'.
      DIGIT3+1 = #0010B (A)
      DIGIT3+2 = #0100B (A)
      GETI SEL0                    ; SELECT A NEW MEMORY BANK.
      EROT_TMR = #00H (XA)         ; USE 'EROT_TMR' AS TEMPORARY ARGUMENT.
      DISPLAY EROT_TMR,DIGIT4,0
      DISPLAY EROT_TMR,DIGIT5,0
      DISPLAY ERR+1,DIGIT6,0
      DISPLAY ERR,DIGIT7,0
      GETI SEL0                    ; SELECT A NEW MEMORY BANK.
      IF_BIT(TRM_ENBL)             ; IF TERMINATE OPTION ENABLED...
        GETI SEL15                 ; ...SELECT A NEW MEMORY BANK.
        XA = #00H
        PCC = A                    ; ...MINIMUM SPEED MODE.
        PORT8 = A                  ; ...TURN OFF THE LEDs AND OP-AMP.
        GETI SEL0                  ; ...SELECT A NEW MEMORY BANK.
        EROT_TMR = #00H (XA)       ; ...CLEAR THE ERROR TIMEOUT TIMER.
        WHILE(FOREVER)             ; ENDLESS LOOP.
          REPEAT
            CALL !DUMP_CHIP        ; IF REQUESTED, DUMP RAM AND REGISTERS TO THE PC.
          UNTIL_BIT(IRQW)          ; WAIT FOR THE HALF SECOND INTERRUPT.
          CLR1 IRQW                ; CLEAR THE HALF SECOND INTERRUPT.
          HL = #EROT_TMR           ; POINT TO THE ERROR TIMEOUT TIMER.
          CALL !INC8               ; INCREMENT THE ERROR TIMEOUT TIMER.
          IF_BIT(CY)               ; IF EROT_TMR = 0 (AFTER 2 min & 8 sec)...
            CALL !POWER_ER         ; ...POWER DOWN UNTIL A BUTTON IS PUSHED.
          ENDIF
        ENDW
      ENDIF
err_end:
      GETI POPMB
      EI                           ; ENABLE THE MASTER INTERRUPT FLAG.
      RET

FOFFSET CSEG XBLOCKA

GETI PUSHMB                  ; SAVE THE MEMORY BANK
      GETI SEL0                    ; SELECT A NEW MEMORY BANK.
      IF_BIT(!CMPT_FOFST)
        GOTO fend
      ENDIF
      XA = #00H                    ; CLEAR THE CURRENT OFFSET.
      OFFSET = XA
      OFFSET+2 = XA IF_BIT(!NEW_PRES)            ; IF A NEW PRESSURE HAS NOT BEEN OBTAINED...
        SET1 NEW_PRES              ; ...SET THE NEW PRESSURE FLAG.
        GOTO fend                  ; ...EXIT THIS ROUTINE AND GO GET A NEW PRESSURE.
      ENDIF
      CLR1 CMPT_FOFST
      ACMLTR = PRSR (XA)           ; LOAD THE ACMLTR WITH PRSR
      ACMLTR+2 = PRSR+2 (XA)
      IF_BIT((ACMLTR+3).3)         ; IF THE PRESSURE IS NEGATIVE (TWOS COMPLIMENT)...
        CALL !TWOS_CMP             ; ...COMPUTE THE ABSOLUTE VALUE OF PRESSURE...
      ENDIF
      ASWORK = ACMLTR (XA)              ; GET ABS(PRSR)
```

```
        ASWORK+2 = ACMLTR+2 (XA)
        ACMLTR = RZWINDOW (XA)          ; GET THE RE-ZERO WINDOW VALUE.
        ACMLTR+2 = #00H (XA)
        CALL !SUB16
        IF_BIT(!CY)                     ; IF RZWINDOW - ABS(PRSR) >= 0...
          ACMLTR = PRSR (XA)            ; ...LOAD THE CURRENT PRESSURE READING.
          ACMLTR+2 = PRSR+2 (XA)
          CALL !TWOS_CMP                ; ...GET TWOS COMPLIMENT.
          OFFSET = ACMLTR (XA)          ; ...STORE THE FINAL OFFSET.
          OFFSET+2 = ACMLTR+2 (XA)
        ELSE                            ; IF RZWINDOW - ABS(PRSR) < 0...
          OFFSET = GEL (XA)             ; ...USE GET AS FINAL OFFSET.
          OFFSET+2 = GEL+2 (XA)
        ENDIF
fend:
        GETI POPMB
        RET

INFLT_BGN CSEG XBLOCKA

GETI PUSHMB                     ; SAVE THE MEMORY BANK
        GETI SEL0                       ; SELECT A NEW MEMORY BANK.
        SBTRCT16 PRSR,BGN_INFL
        IF_BIT(!CY)                     ; IF PRSR - BGN_INFL >= 0 THEN...
          SET1 INFLATING                ; ...SET INFLATING FLAG.
          XA = #00H
          PRSR_M = XA                   ; ...CLEAR THE MAX PRESSURE VALUE.
          PRSR_M+2 = XA
          CALL !CLR_TIME                ; ...CLEAR THE TIMER.
        ENDIF
        GETI POPMB                      ; RESTORE THE MEMORY BANK
        RET

INFLT_END CSEG XBLOCKA

GETI PUSHMB                     ; SAVE THE MEMORY BANK
        GETI SEL0                       ; SELECT A NEW MEMORY BANK.
        SBTRCT16 END_INFL,PRSR
        IF_BIT(!CY)                     ; IF END_INFL - PRSR >= 0 THEN...
          CLR1 INFLATING
          GETI SEL1
          T0_LAST = T0_DSPL (A)         ; SAVE THE INFLATION TIME DISPLAY.
          T1_LAST = T1_DSPL (A)
          T2_LAST = T2_DSPL (A)
          T3_LAST = T3_DSPL (A)
          CALL !CLR_TIME                ; CLEAR THE TIMER.
        ENDIF
        GETI POPMB                      ; RESTORE THE MEMORY BANK
        RET

INFLT_STAT CSEG XBLOCKA

GETI PUSHMB                     ; SAVE THE MEMORY BANK
        GETI SEL0                       ; SELECT A NEW MEMORY BANK.
        IF_BIT(INFLATING)               ; IF CURRENTLY INFLATING...
          CALL !INFLT_END               ; ...SEE IF PRESSURE IS <= END_INFL
          CALL !PRES_MAX                ; ...SEE IF THE CURRENT PRESSURE IS THE MAXIMUM FOR THIS INFLATION.
        ELSE                            ; ELSE (CURRENTLY DEFLATING)...
          CALL !INFLT_BGN               ; ...SEE IF PRESSURE IS => BGN_INFL
        ENDIF
        GETI POPMB
        RET

INIT_CLK CSEG XBLOCKA

GETI PUSHMB                     ; SAVE THE MEMORY BANK.
        GETI SEL15                      ; SELECT A NEW MEMORY BANK.
        CLR1 SCC.3                      ; SET THE SYSTEM...
```

```
        CLR1 SCC.0              ; ...CONTROL CLOCK (PAGE 5-31).
        PCC = #0010B (A)        ; SET THE PROCESSOR CLOCK CONTROL REGISTER (PAGE 5-30).
        BTM = #1111B (A)        ; SET THE BASIC INTERVAL TIMER MODE REGISTL   AGE 5-44).
        WM = #00000100B (XA)    ; SET THE WATCH MODE REGISTER (PAGE 5-53).
        GETI POPMB
        RET

INIT_LCD CSEG XBLOCKA

GETI PUSHMB             ; SAVE THE MEMORY BANK
        GETI SEL15              ; SELECT A NEW MEMORY BANK.
        LCDM = #00101001B (XA)  ; SET THE DISPLAY MODE REGISTER (PAGE 5-126).
        LCDC = #0101B (A)       ; SET THE DISPLAY CONTROL REGISTER (PAGE 5-129).
        GETI POPMB
        RET

INIT_PRT CSEG XBLOCKA

GETI PUSHMB             ; SAVE THE MEMORY BANK
        GETI SEL15              ; SELECT A NEW MEMORY BANK.
        POGA = #00000011B (XA)
        POGB = #00000000B (XA)
        XA = #00H
        PMGA = XA               ; SET ALL PORTS AS INPUT....
        PMGB = XA               ;
        PMGC = #00000001B (XA)  ; ...EXCEPT FOR PORT 8.
        PORT8 = #0000B (A)      ; TURN LEDs AND OP-AMP OFF.
        GETI POPMB
        RET

INIT_RAM CSEG XBLOCKA
        GETI SEL0               ; SELECT MEMORY BANK 0.
        XA = #00H
        HL = #04H
        REPEAT
          REPEAT
            @HL = A             ; CLEAR MEMORY DESIGNATED BY THE POINTER @HL.
            L++                 ; INCREMENT AND SKIP THE NEXT INSTRUCTION ON A CARRY.
          UNTIL(FOREVER)
          H++                   ; INCREMENT AND SKIP THE NEXT INSTRUCTION ON A CARRY.
        UNTIL(FOREVER)
        GETI SEL1               ; SELECT MEMORY BANK 1.
        HL = #00H
        REPEAT
          REPEAT
            @HL = A             ; CLEAR MEMORY DESIGNATED BY THE POINTER @HL.
            L++                 ; INCREMENT AND SKIP THE NEXT INSTRUCTION ON A CARRY.
          UNTIL(FOREVER)
          H++                   ; INCREMENT AND SKIP THE NEXT INSTRUCTION ON A CARRY.
        UNTIL(FOREVER)
        GETI SEL15              ; SELECT A NEW MEMORY BANK.
        SP = #STACK (XA)        ; SET THE STACK POINTER.
        STKLN 94                ; SET THE STACK LENGTH (IN DECIMAL NIBBLES).
        GETI SEL0               ; SELECT MEMORY BANK 0 FOR THE MAIN LOOP.
        GOTO RAM_RET

INIT_VAR CSEG XBLOCKA

GETI PUSHMB             ; SAVE THE MEMORY BANK.
        GETI SEL0               ; SELECT A NEW MEMORY BANK.
        A1 = #00DH (XA)         ; DEFINE LOW AND HIGH NIBBLE (RESPECTIVELY) OF A1.
        A1+2 = #01H (XA)        ; THIS NUMBER MUST BE A POSITIVE VALUE.
        C1 = #0F8H (XA)         ; DEFINE LOW AND HIGH NIBBLE (RESPECTIVELY) OF C1.
        C1+2 =#0FFH (XA)        ; THIS NUMBER MAY BE POSITIVE OR NEGATIVE.
                                ; IF NEGATIVE, THE FORMAT IS 2s COMPLIMENT.

A2 = #08H (XA)          ; DEFINE LOW AND HIGH NIBBLE (RESPECTIVELY) OF A1.
```

```
        A2+2 = #01H (XA)        ; THIS NUMBER MUST BE A POSITIVE VALUE.
        C2 = #0FAH (XA)         ; DEFINE LOW AND HIGH NIBBLE (RESPECTIVELY) OF C1.
        C2+2 =#0FFH (XA)        ; THIS NUMBER MAY BE POSITIVE OR NEGATIVE.
                                ; IF NEGATIVE, THE FORMAT IS 2s COMPLIMENT.
        CH_MODEL = #067H (XA)   ; THE A/D VALUE WHICH IS THE BOUNDARY FOR THE TWO...
                                ; ...LINEAR MODELS.
        GEL = #00H (XA)         ; DEFINE LOW AND HIGH NIBBLE (RESPECTIVELY) OF C1.
        GEL+2 =#00H (XA)        ; THIS NUMBER MAY BE POSITIVE OR NEGATIVE.
                                ; IF NEGATIVE, THE FORMAT IS 2s COMPLIMENT.
        SET1 TRM_ENBL           ; ENABLE TERMINATION WHEN AN ERROR OCCURS.
        CLR1 PSI                ; DISPLAY IN ATMOSPHERES, NOT PSI.
        TMOT_VAL = #040D (XA)   ; SET DEFAULT FOR TIMEOUT (UNITS ARE MINUTES).
        LDOT_VAL = #07D (XA)    ; SET DEFAULT FOR LED POWER-DOWN (UNITS ARE MINUTES).
        SET1 LED_ENBL           ; THE LED ENABLE FLAG.
        BSP_VAL = #015D (XA)    ; SET THE BUTTON PUSH SAMPLE RATE.
        BTN_VAL = #05H (A)      ; SET DEFAULT # OF BUTTON PUSHES (IN 1 SEC) FOR POWER-DOWN.
        BAND_VAL = #02H (A)     ; SET DEFAULT FOR A2D BAND VALUE.

A2D_MAX = #0FEH (XA)    ; SET DEFAULT FOR MAXIMUM A/D THRESHOLD VALUE.
        A2D_MIN = #03H (XA)     ; SET DEFAULT FOR MINIMUM A/D THRESHOLD VALUE.

DSPL_MAX = #0FFH (XA)   ; DSPL_MAX (IN UNITS OF .1 ATM).
        DSPL_MAX+2 = #00H (XA)
        DSPL_MIN = #0F7H (XA)   ; DSPL_MIN (IN UNITS OF .1 ATM).
        DSPL_MIN+2 = #0FFH (XA)

EXTN_MIN = #0250D (XA)
        NLEG_MAX = #056H (XA)   ; .3170 * 255 + 5
        NLEG_MIN = #012H (XA)   ; .0922 * 255 - 5
        PLEG_MAX = #059H (XA)   ; .3287 * 255 + 5
        PLEG_MIN = #017H (XA)   ; .1130 * 255 - 5

LED_VAL = #010D (XA)    ; SET LED DUTY PARAMETER.
        PRSR_VAL = #0100D (XA)  ; SET PRESSURE SAMPLING FREQUENCY PARAMETER.
        ZWINDOW = #02H (XA)     ; SET THE ZERO WINDOW.
        RZWINDOW = #03H (XA)    ; SET THE RE-ZERO WINDOW.
        BGN_INFL = #07H (XA)    ; SET THE PRESSURE THRESHOLD WHICH BEGINS A NEW INFLATION.
        BGN_INFL+2 = #00H (XA)
        END_INFL = #00H (XA)    ; SET THE PRESSURE THRESHOLD WHICH ENDS AN INFLATION.
        END_INFL+2 = #00H (XA)
        GETI SEL1               ; SELECT A NEW MEMORY BANK.
        SET1 HALF_SEC
        TWO_1 = #02H (A)
        FIVE_1 = #05H (A)
        SIX_1 = #06D (A)
        TEN_1 = #10D (A)
        GETI POPMB              ; RESTORE THE MEMORY BANK.
        RET

INTERRUPT CSEG XBLOCKA

GETI PUSHMB
        SAV_ACMLTR
        GETI SEL15              ; SELECT A NEW MEMORY BANK.
        BTM = #1111B (A)        ; SET TIMER FOR 1.95 ms
        GETI SEL0               ; SELECT A NEW MEMORY BANK
        SET1 INTRPTD            ; SET FLAG INDICATING THAT THERE HAS BEEN AN INTERRUPT
        HL = #LED_CNTR          ; INCREMENT LED_CNTR.
        CALL !INC8
        HL = #PRSR_CNTR         ; INCREMENT THE PRSR_CNTR.
        CALL !INC8
        HL = #BSP_CNTR          ; INCREMENT THE BUTTON SAMPLE PERIOD COUNTE
        CALL !INC8
        SBTRCT8 LED_CNTR, LED_VAL
        IF_BIT(CY)              ; IF LED_CNTR - LED_VAL < 0...
          CLR1 LED_ON           ; ...CLEAR THE LED FLAG.
          GETI SEL15            ; ...SELECT A NEW MEMORY BANK.
          CLR1 PORT8.2          ; ...TURN THE LEDs OFF
          CLR1 PORT8.1
        ELSE
          LED_CNTR = #00H (XA)  ; ...RESET THE LED COUNTER
```

```
      IF_BIT(LED_ENBL)      ; ...IF THE LEDs ARE ENABLED
        SET1 LED_ON         ; ...SET THE LED FLAG
        GETI SEL15          ; ...SELECT A NEW MEMORY BANK.
        SET1 PORT8.2        ; ...TURN THE LEDs ON.
        SET1 PORT8.1
      ENDIF
    ENDIF
    GETI SEL0               ; SELECT A NEW MEMORY BANK.
    HL = #WTCH_DOG          ; INCREMENT THE WATCHDOG COUNTER.
    CALL !INC8
    ACMLTR = #0F0H (XA)
    SBTRCT8 ACMLTR, WTCH_DOG
    IF_BIT(CY)              ; IF #F0H - WATCH DOG TIMER < 0...
      SET1 TRM_ENBL         ; ...ENABLE PROGRAM TERMINATION...
      ERR = #07H (XA)       ; ...LOAD ERROR CODE...
      CALL !ERROR           ; ...DISPLAY THE ERROR CODE.
    ENDIF
    RES_ACMLTR
    GETI POPMB
    RETI

LCD_ANUN CSEG XBLOCKA

GETI PUSHMB             ; SAVE THE MEMORY BANK.
    GETI SEL1               ; SELECT A NEW MEMORY BANK.
    CLR1 L_INFLTN           ; TURN OFF THE 'LAST INFLATION' ANNUNCIATOR.
    GETI SEL0               ; SELECT A NEW MEMORY BANK.
    IF_BIT(NEG_PRES)
      GETI SEL1             ; SELECT A NEW MEMORY BANK.
      DIGIT2+0 = #0000B (A) ; WRITE OUT A DASH TO THE DIGIT.
      DIGIT2+1 = #0010B (A)
      DIGIT2+2 = #0000B (A)
    ENDIF
    GETI SEL0               ; SELECT A NEW MEMORY BANK
    IF_BIT(MAX_ON)
      GETI SEL1             ; SELECT A NEW MEMORY BANK
      SET1 MAX              ; SET THE MAXIMUM ANNUNCIATOR.
      CALL !LCD_BLINK       ; MAKE THE PRESSURE DIGITS FLASH ON AND OFF.
    ELSE
      GETI SEL1             ; SELECT A NEW MEMORY BANK
      CLR1 MAX              ; CLEAR THE MAXIMUM ANNUNCIATOR.
    ENDIF
    GETI SEL0               ; SELECT A NEW MEMORY BANK
    IF_BIT(MIN_ON)
      GETI SEL1             ; SELECT A NEW MEMORY BANK
      DIGIT2+0 = #0000B (A) ; WRITE OUT A DASH TO THE DIGIT.
      DIGIT2+1 = #0010B (A)
      DIGIT2+2 = #0000B (A)
      DIGIT3+0 = #0000B (A) ; WRITE OUT A DASH TO THE DIGIT.
      DIGIT3+1 = #0010B (A)
      DIGIT3+2 = #0000B (A)
      SET1 MIN              ; SET THE MINIMUM ANNUNCIATOR.
      CALL !LCD_BLINK       ; MAKE THE PRESSURE DIGITS FLASH ON AND OFF.
    ELSE
      GETI SEL1             ; SELECT A NEW MEMORY BANK
      CLR1 MIN              ; CLEAR THE MINIMUM ANNUNCIATOR.
    ENDIF
    GETI POPMB              ; RESTORE THE MEMORY BANK.
    RET

LCD_BLINK CSEG XBLOCKA

GETI PUSHMB             ; SAVE THE MEMORY BANK.
    GETI SEL1               ; SELECT A NEW MEMORY BANK.
    IF_BIT(HALF_SEC)
      A = #00H
      DIGIT1+0 = A
      DIGIT1+1 = A
      DIGIT2+0 = A
```

```
        DIGIT2+1 = A
        DIGIT2+2 = A
        DIGIT3+0 = A
        DIGIT3+1 = A
        DIGIT3+2 = A
      ENDIF
      GETI POPMB              ; RESTORE THE MEMORY BANK.
      RET

LCD_CURR CSEG XBLOCKA

GETI PUSHMB             ; SAVE THE MEMORY BANK.
      GETI SEL1               ; SELECT A NEW MEMORY BANK.
      DISPLAY T0_DSPL,DIGIT7,0    ; INVOKE A MACRO.
      DISPLAY T1_DSPL,DIGIT6,0    ; INVOKE A MACRO.
      DISPLAY T2_DSPL,DIGIT5,0    ; INVOKE A MACRO.
      DISPLAY T3_DSPL,DIGIT4,0    ; INVOKE A MACRO.
      DISPLAY P0_DSPL,DIGIT3,0    ; WRITE OUT THE FIRST DIGIT OF PRESSURE.
      GETI SEL0               ; WRITE OUT THE SECOND DIGIT OF PRESSURE.
      IF_BIT(!NEG_PRESS)      ; IF PRESSURE IS NOT NEGATIVE...
        GETI SEL1             ; SELECT A NEW MEMORY BANK.
        DISPLAY P1_DSPL,DIGIT2,0  ; INVOKE A MACRO
      ENDIF
      GETI SEL1               ; SELECT A NEW MEMORY BANK.
      DISPLAY P2_DSPL,DIGIT1,2    ; WRITE OUT THE THIRD DIGIT OF PRESSURE.
      CALL !LCD_ANUN          ; HANDLE CURRENT ANNUNCIATORS.
      GETI POPMB              ; RESTORE THE MEMORY BANK.
      RET

LCD_MAIN CSEG XBLOCKA

GETI PUSHMB             ; SAVE THE CURRENT MEMORY BANK.
      GETI SEL15              ; SELECT A NEW MEMORY BANK.
      PCC = #0011B (A)
      GETI SEL0               ; SELECT A NEW MEMORY BANK.
      IF_BIT(ERR_BIT)
        GOTO lcdm_end
      ENDIF
      IF_BIT(INFLATING || PORT0.0)  ; IF CURRENTLY INFLATING OR BUTTON UP.
        CALL !LCD_CURR        ; ...DISPLAY CURRENT DATA.
      ELSE                    ; ELSE
        CALL !LCD_PREV        ; ...DISPLAY THE PREVIOUS INFLATION.
      ENDIF
      IF_BIT(PSI)             ; IF PSI REQUESTED...
        GETI SEL1             ; SELECT A NEW MEMORY BANK.
        CLR1 DECIMAL
      ELSE
        GETI SEL1             ; SELECT A NEW MEMORY BANK.
        SET1 DECIMAL          ; TURN A DECIMAL POINT ON.
      ENDIF
      SET1 COLON              ; TURN THE COLON ON
lcdm_end:
      GETI SEL15              ; SELECT A NEW MEMORY BANK.
      PCC = #0010B (A)
      GETI POPMB              ; RESTORE THE MEMORY BANK.
      RET

LCD_PREV CSEG XBLOCKA

GETI PUSHMB             ; SAVE THE MEMORY BANK.
      GETI SEL1               ; SELECT A NEW MEMORY BANK.
      DISPLAY T0_LAST,DIGIT7,0    ; INVOKE A MACRO.
      DISPLAY T1_LAST,DIGIT6,0    ; INVOKE A MACRO.
      DISPLAY T2_LAST,DIGIT5,0    ; INVOKE A MACRO.
      DISPLAY T3_LAST,DIGIT4,0    ; INVOKE A MACRO.
      DISPLAY P2_LAST,DIGIT1,2    ; INVOKE A MACRO
      DISPLAY P1_LAST,DIGIT2,0    ; INVOKE A MACRO
      DISPLAY P0_LAST,DIGIT3,0    ; INVOKE A MACRO
```

```
        SET1 L_INFLTN              ; TURN ON THE 'LAST INFLATION' ANNUNCIATOR.
        CLR1 MIN                   ; TURN THE MINIMUM INDICATOR OFF.
        GETI POPMB                 ; RESTORE THE MEMORY BANK.
        RET

MODEL CSEG XBLOCKA

GETI PUSHMB                ; SAVE THE MEMORY BANK
        GETI SEL0                  ; SELECT A NEW MEMORY BANK.
        SBTRCT8 A2D, CH_MODEL
        IF_BIT(CY)                 ; IF A2D - CH_MODEL < 0
          GETI SEL0                ; ...SELECT A NEW MEMORY BANK.
          MULTC = A1 (XA)          ; ...LOAD THE MODEL SCALER.
          MULTC+2 = A1+2 (XA)      ;
          ACMLTR = C1 (XA)         ; ...LOAD THE MODEL OFFSET.
          ACMLTR+2 = C1+2 (XA)     ;
        ELSE                       ; ELSE
          GETI SEL0                ; ...SELECT A NEW MEMORY BANK.
          MULTC = A2 (XA)          ; ... LOAD THE MODEL SCALER.
          MULTC+2 = A2+2 (XA)      ;
          ACMLTR = C2 (XA)         ; LOAD THE MODEL OFFSET.
          ACMLTR+2 = C2+2 (XA)     ;
        ENDIF
        MULTA = A2D (XA)           ; GET THE A/D READING.
        XA = #00H
        MULTA+2 = XA
        MULTB = XA                 ; INITIALIZE THE MULTB WORK SPACE.
        MULTB+2 = XA
        CALL !MULT16               ; MULTIPLY THE A/D READING BY THE SCALER.
        ASWORK = MULTB+2 (XA)      ; DIVIDE (A*A2D) BY 256D BY SHIFTING RIGHT....
        ASWORK+2 = MULTA (XA)      ; ...TWO NIBBLES (ONE BYTE).
        CALL !ADD16                ; ADD C TO (A/256D)*A2D.
        ASWORK = OFFSET (XA)
        ASWORK+2 = OFFSET+2 (XA)
        CALL !ADD16                ; ADD OFFSET TO (A/256D)*A2D+C.
        PRSR = ACMLTR (XA)
        PRSR+2 = ACMLTR+2 (XA)
        GETI POPMB                 ; RESTORE THE MEMORY BANK
        RET

POWER CSEG XBLOCKA

GETI PUSHMB                ; SAVE THE MEMORY BANK.
        DI                         ; DISABLE MASTER INTERRUPT FLAG (p.7-9).
        EI IE4                     ; ENABLE BUTTON TO POWER UP.
        DI IEW                     ; DISABLE THE WATCH TICK INTERRUPT.
        GETI SEL15                 ; SELECT A NEW MEMORY BANK.
        XA = #00H                  ; LOAD XA REGISTER WITH ZERO.
        PCC = A                    ; SELECT THE MINIMUM PROCESSOR SPEED.
        LCDM = XA                  ; TURN THE...
        LCDC = A                   ; ...LCDs OFF.
        WM = XA                    ; CLEAR THE WATCH MODE REGISTER
        POGA = XA                  ; DISABLE ALL I/O PORT...
        POGB = XA                  ; ...PULL-UP RESISTORS.
        PMGA = XA                  ; PLACE ALL INPUT/OUTPUT PORTS...
        PMGB = XA                  ; ...IN HIGH IMPEDANCE MODE (INPUT)...
        PMGC = #00000001B (XA)     ; ...EXCEPT PORT 8.
        PORT8 = #0000B (A)         ; TURN OFF THE LEDs AND OP-AMP.
        REPEAT
          BTM = #1011B (A)         ; SET FOR 31.3 ms WAIT.
          REPEAT
          UNTIL_BIT(IRQBT)
        UNTIL_BIT(PORT0.0 && PORT0.0)
        CALL !C_BCKUP              ; BACKUP THE MODEL CONSTANTS INTO A SEPARATE MEMORY BANK.
        CLR1 IRQ4                  ; CLEAR THE BUTTON INTERRUPT REQUEST FLAG.
        CLR1 IRQBT                 ; CLEAR THE BASIC INTERVAL TIMER REQUEST FLAG.
        CLR1 IRQCSI                ; CLEAR THE SERIAL COMMUNICATION INTERRUPT REQUEST.
        CLR1 IRQW                  ; CLEAR THE WATCH TICK INTERRUPT REQUEST FLAG.
        BTM = #1000B (A)           ; SET FOR 250 ms DELAY AFTER STANDBY MODE RELEASED.
```

```
            STOP                    ; PLACE THE SYSTEM IN STANDBY MODE.
            NOP                     ; THIS NOP MUST FOLLOW THE STOP.
            SET1 BTM.3              ; WAIT.
            REPEAT
            UNTIL_BIT(IRQBT)
            CALL !INIT_CLK          ; RESET THE CLOCKS AND TIMERS.
            CALL !INIT_PRT          ; RESET THE PORTS.
            CALL !INIT_LCD          ; RESET THE LCD CONTROLS.
            REPEAT
              BTM = #1011B (A)      ; SET FOR 31.3 ms WAIT.
              REPEAT
              UNTIL_BIT(IRQBT)
            UNTIL_BIT(PORT0.0 && PORT0.0)
            CALL !C_VRFY            ; VERIFY THE MODEL CONSTANTS.
            GETI SEL0               ; SELECT A NEW MEMORY BANK.
            SET1 CMPT_FOFST         ; SET FLAG WHICH WILL TRIGGER THE COMPUTATION...
                                    ; ...OF THE FINAL OFFSET VALUE.
            CLR1 NEW_PRES           ; SET FLAG SO A NEW PRESSURE WILL BE COMPUTED...
                                    ; ...BEFORE THE FINAL OFFSET IS COMPUTED.
            WTCH_DOG = #00H (XA)    ; CLEAR THE WATCH DOG COUNTER.
            CLR1 STANDBY            ; DISABLE A BUTTON INVOKED POWER-DOWN.
            PRSR_CNTR = #00H (XA)   ; RESET THE PRESSURE COUNTER.

XA = LED_VAL            ; SET LED COUNTER EQUAL TO LED_VAL / 2,
            CLR1 CY                 ; ...THIS OFFSET TO THE LED COUNTER
            A <-> X                 ; ...RELATIVE TO THE PRESSURE COUNTER IS TO
            RORC A                  ; ...HELP INSURE THAT THE LEDs AND THE OP-AMP
            A <-> X                 ; ...WILL NOT BE OPERATING AT THE SAME TIME.
            RORC A                  ;
            LED_CNTR = XA           ;
            EI IEW                  ; ENABLE THE WATCH TICK INTERRUPT.
            DI IE4                  ; DISABLE BUTTON INTERRUPT.
            EI                      ; ENABLE MASTER INTERRUPT FLAG
            GETI POPMB              ; RESTORE THE MEMORY BANK
            RET

POWER_ER CSEG XBLOCKA

GETI PUSHMB             ; SAVE THE MEMORY BANK.
            EI IE4                  ; ENABLE BUTTON TO POWER UP.
            DI IEW                  ; DISABLE THE WATCH TICK INTERRUPT.
            GETI SEL15              ; SELECT A NEW MEMORY BANK.
            XA = #00H               ; LOAD XA REGISTER WITH ZERO.
            PCC = A                 ; SELECT THE MINIMUM PROCESSOR SPEED.
            LCDM = XA               ; TURN THE...
            LCDC = A                ; ...LCDs OFF.
            WM = XA                 ; CLEAR THE WATCH MODE REGISTER
            POGA = XA               ; DISABLE ALL I/O PORT...
            POGB = XA               ; ...PULL-UP RESISTORS.
            PMGA = XA               ; PLACE ALL INPUT/OUTPUT PORTS...
            PMGB = XA               ; ...IN HIGH IMPEDANCE MODE (INPUT)...
            PMGC = #00000001B (XA)  ; ...EXCEPT PORT 8.
            PORT8 = #0000B (A)      ; TURN OFF THE LEDs AND OP-AMP.
            REPEAT
              BTM = #1011B (A)      ; SET FOR 31.3 ms WAIT.
              REPEAT
              UNTIL_BIT(IRQBT)
            UNTIL_BIT(PORT0.0 && PORT0.0)
            CLR1 IRQ4               ; CLEAR THE BUTTON INTERRUPT REQUEST FLAG.
            CLR1 IRQBT              ; CLEAR THE BASIC INTERVAL TIMER REQUEST FLAG.
            CLR1 IRQCSI             ; CLEAR THE SERIAL COMMUNICATION INTERRUPT REQUEST.
            CLR1 IRQW               ; CLEAR THE WATCH TICK INTERRUPT REQUEST FLAG.
            BTM = #1000B (A)        ; SET FOR 250 ms DELAY AFTER STANDBY MODE RELEASED.
            STOP                    ; PLACE THE SYSTEM IN STANDBY MODE.
            NOP                     ; THIS NOP MUST FOLLOW THE STOP.
            SET1 BTM.3              ; WAIT.
            REPEAT
            UNTIL_BIT(IRQBT)
            CALL !INIT_CLK          ; RESET THE CLOCKS AND TIMERS.
            CALL !INIT_PRT          ; RESET THE PORTS.
```

```
        CALL !INIT_LCD         ; RESET THE LCD CONTROLS.
        REPEAT
          BTM = #1011B (A)     ; SET FOR 31.3 ms WAIT.
          REPEAT
          UNTIL_BIT(IRQBT)
        UNTIL_BIT(PORTO.0 && PORTO.0)
        EI IEW                 ; ENABLE THE WATCH TICK INTERRUPT.
        DI IE4                 ; DISABLE BUTTON INTERRUPT.
        GETI POPMB             ; RESTORE THE MEMORY BANK
        RET

PRES_DSPL CSEG XBLOCKA

GETI PUSHMB            ; SAVE THE MEMORY BANK
        GETI SEL0              ; SELECT A NEW MEMORY BANK.
        ACMLTR = PRSR (XA)     ; LOAD THE ACMLTR WITH PRSR
        ACMLTR+2 = PRSR+2 (XA)
        IF_BIT((ACMLTR+3).3)   ; IF THE PRESSURE IS NEGATIVE (TWOS COMPLIMENT)...
          CALL !TWOS_CMP       ; ...TAKE TWOS COMPLIMENT TO GET ABSOLUTE VALUE.
          SET1 NEG_PRES        ; ...SET NEGATIVE PRESSURE FLAG.
        ELSE                   ; ELSE
          CLR1 NEG_PRES        ; ...CLEAR THE NEGATIVE PRESSURE FLAG.
        ENDIF
        IF_BIT(PSI)            ; IF PSI REQUESTED, ACMLTR = PSI*376/256
          MULTA = ACMLTR (XA)  ; ...LOAD MULTA WITH ABS(PRSR)
          MULTA+2 = ACMLTR+2 (XA)
          MULTC = #078H (XA)   ; ...LOAD MULTC WITH 178H (376D).
          MULTC+2 = #01 (XA)
          XA = #00H
          MULTB = XA
          MULTB+2 = XA
          CALL !MULT16         ; ...MULTIPLY PRSR BY 376D.
          ACMLTR = MULTB+2 (XA); ...DIVIDE PRSR BY 256
          ACMLTR+2 = MULTA (XA)
        ENDIF
        XA = ACMLTR
        GETI SEL1
        BCD_WRK = XA           ; LOAD THE LOW 8 BITS OF ABS(PRSR)
        CALL !BDCNV            ; CONVERT THE LOW 8 BITS OF PRSR TO BCD
        CALL !BCD_NINTH        ; CONVERT THE NINTH BIT OF PRSR TO BCD.
        P0_DSPL = BCD_WRK (A)  ; LOAD THE BCD INTO THE PRESSURE DISPLAY VARIABLES.
        P1_DSPL = BCD_WRK+1 (A);
        P2_DSPL = BCD_WRK+2 (A);
        GETI POPMB
        RET

PRES_LIM CSEG XBLOCKA

GETI PUSHMB            ; SAVE THE MEMORY BANK
        GETI SEL0              ; SELECT A NEW MEMORY BANK.
        ACMLTR = PRSR (XA)     ; GET THE ABSOLUTE VALUE OF THE PRESSURE.
        ACMLTR+2 = PRSR+2 (XA)
        IF_BIT((ACMLTR+3).3)
          CALL !TWOS_CMP
        ENDIF
        ASWORK = ACMLTR (XA)   ; LOAD THE ABSOLUTE VALUE OF THE PRESSURE
        ASWORK+2 = ACMLTR+2 (XA)
        ACMLTR = ZWINDOW (XA)
        ACMLTR+2 = #00H (XA)
        CALL !SUB16
        IF_BIT(!CY)            ; IF ZWINDOW - ABS(PRSR) >= 0...
          IF_BIT(!NEG_PRES)    ; ...IF PRSR >= 0 (IF PRSR NOT NEGATIVE)...
            XA = #00H          ; ...SET PRSR = 0
            PRSR = XA
            PRSR+2 = XA
          ENDIF
          SET1 Z_FLAG          ; ...INDICATE THAT PRSR IS INSIDE ZERO WINDOW.
        ELSE                   ; ELSE
          CLR1 Z_FLAG          ; ...INDICATE THAT PRSR IS OUTSIDE ZERO WINDOW.
        ENDIF
```

```
          ACMLTR = ZWINDOW (XA)
          ACMLTR+2 = #00H (XA)
          ASWORK = PRSR (XA)
          ASWORK+2 = PRSR+2 (XA)
          CALL !SUB16
          IF_BIT(CY)              ;IF ZWINDOW - PRSR < 0...
            SET1 LED_ENBL         ; ...ENABLE THE LEDs (THE LEDs MAY ALREADY BE ENABLED).
            TMOT_TMR = #00H (XA)  ; ...RESET THE TIME-OUT TIMER.
          ENDIF
          CLR1 MIN_ON             ; CLEAR THE MINIMUM INDICATOR.
          CLR1 MAX_ON             ; CLEAR THE MAXIMUM INDICATOR.
          SBTRCT16 DSPL_MIN, PRSR
          IF_BIT(!CY)             ; IF DSPL_MIN - PRSR  >= 0 THEN...
            PRSR = DSPL_MIN (XA)  ; ...SET PRSR = DSPL_MIN
            PRSR+2 = DSPL_MIN+2 (XA)
            SET1 MIN_ON           ; ...SET THE MINIMUM INDICATOR.
            GOTO prslm_end        ; ...EXIT THIS ROUTINE.
          ENDIF
          SBTRCT16 PRSR, DSPL_MAX
          IF_BIT(!CY)             ; IF PRSR - DSPL_MAX >= 0 THEN...
            PRSR = DSPL_MAX (XA)  ; ...SET PRSR = DSPL_MAX
            PRSR+2 = DSPL_MAX+2 (XA)
            SET1 MAX_ON           ; ...SET THE MINIMUM INDICATOR.
            GOTO prslm_end        ; ...EXIT THIS ROUTINE.
          ENDIF
          SBTRCT8 A2D_MIN, A2D
          IF_BIT(!CY)             ; IF A2D_MIN - A2D >= 0
            SET1 MIN_ON           ; ...TURN THE MINIMUM INDICATOR ON.
            GOTO prslm_end        ; ...EXIT THIS ROUTINE.
          ENDIF
          SBTRCT8 A2D, A2D_MAX
          IF_BIT(!CY)             ; IF A2D - A2D_MAX IS >= 0...
            SET1 MAX_ON           ; ...SET THE MAXIMUM INDICATOR
            GOTO prslm_end        ; ...EXIT THIS ROUTINE.
          ENDIF
prslm_end:
          GETI POPMB
          RET

PRES_MAX CSEG XBLOCKA

GETI PUSHMB             ; SAVE THE MEMORY BANK
          GETI SEL0               ; SELECT A NEW MEMORY BANK.
          SBTRCT16 PRSR_M, PRSR
          IF_BIT(CY)              ; IF PRSR_M - PRSR < 0...
            PRSR_M = PRSR (XA)    ; UPDATE THE MAX PRESSURE AND LAST PRESSURE.
            PRSR_M+2 = PRSR+2 (XA)
            GETI SEL1             ; SELECT A NEW MEMORY BANK.
            P0_LAST = P0_DSPL (A) ; SAVE THE CURRENT PRESSURE DISPLAY DATA.
            P1_LAST = P1_DSPL (A)
            P2_LAST = P2_DSPL (A)
          ENDIF
          GETI POPMB
          RET

PRESSURE CSEG XBLOCKA

GETI PUSHMB             ; SAVE THE MEMORY BANK
          GETI SEL15              ; SELECT A NEW MEMORY BANK.
          PCC = #0011B (A)
          GETI SEL0               ; SELECT A NEW MEMORY BANK.
          SBTRCT8 PRSR_CNTR,PRSR_VAL
          IF_BIT(LED_ON || CY)    ;IF LEDs ARE ON OR PRSR_CNTR - PRSR_VAL < 0...
            GOTO prsr_end         ; ...EXIT THIS ROUTINE.
          ENDIF
          PRSR_CNTR = #00H (XA)   ; RESET THE COUNTER.
          CALL !READ_AD           ; READ THE A TO D.
          CALL !BAND              ; SEE IF THE CURRENT A2D READING IS 'BANDED'.
          CALL !MODEL             ; THE PRESSURE IS IN 'PRSR' WHEN THIS ROUTINE IS COMPLETED.
          CALL !FOFFSET           ; COMPUTE THE FINAL OFFSET?.
```

```
        CALL !PRES_LIM       ; THE PRESSURE IS IN 'PRSR' WHEN THIS ROUTINE IS COMPLETED.
        CALL !PRES_DSPL      ; COMPUTE PRESSURE DISPLAY DATA.
        CALL !INFLT_STAT     ; CHECK CURRENT INFLATION STATUS.
        CALL !LCD_MAIN       ; UPDATE THE LCD.
        GETI SEL15           ; SELECT A NEW MEMORY BANK.
        PCC = #0010B (A)
prsr_end:
        GETI POPMB           ; RESTORE THE MEMORY BANK.
        RET

READ_AD CSEG XBLOCKA

GETI PUSHMB          ; SAVE THE MEMORY BANK
        GETI SEL0            ; SELECT A MEMORY BANK
        CLR1 ERR_BIT
        SET1 PORT8.3         ; TURN THE OP-AMP ON
        CLR1 IRQBT
        CLR1 INTRPTD
        REPEAT
        UNTIL_BIT(IRQBT || INTRPTD)   ; CHECK BOTH (IN CASE MASTER INTERRUPT DISABLED).
        CLR1 IRQBT
        AD_VALUE #03H,EXCTN  ; INVOKE MACRO TO GET A/D VALUE.

SBTRCT8 EXCTN,EXTN_MIN
        IF_BIT(CY)           ; IF EXCTN - EXTN_MIN < 0...
          ERR = #01H (XA)    ; ...LOAD THE ERROR CODE...
          CALL !ERROR        ; ...WRITE ERROR MESSAGE, TERMINATE PROGRAM.
          GOTO read_end
        ENDIF
        AD_VALUE #01H,NLEG   ; INVOKE MACRO TO GET A/D VALUE.

SBTRCT8 NLEG_MAX,NLEG
        IF_BIT(CY)           ; IF NLEG_MAX - NLEG < 0...
          ERR = #02H (A)     ; ...LOAD THE ERROR CODE...
          CALL !ERROR        ; ...DISPLAY THE ERROR CODE.
          GOTO read_end
        ENDIF SBTRCT8 NLEG,NLEG_MIN
        IF_BIT(CY)           ; IF NLEG - NLEG_MIN < 0...
          ERR = #03H (A)     ; ...LOAD THE ERROR CODE...
          CALL !ERROR        ; ...DISPLAY THE ERROR CODE.
          GOTO read_end
        ENDIF
        AD_VALUE #02H,PLEG   ; INVOKE MACRO TO GET A/D VALUE.

SBTRCT8 PLEG_MAX,PLEG
        IF_BIT(CY)           ; IF PLEG_MAX - PLEG < 0...
          ERR = #04H (A)     ; ...LOAD THE ERROR CODE...
          CALL !ERROR        ; ...DISPLAY THE ERROR CODE.
          GOTO read_end
        ENDIF SBTRCT8 PLEG,PLEG_MIN
        IF_BIT(CY)           ; IF PLEG - PLEG_MIN < 0...
          ERR = #05H (A)     ; ...LOAD THE ERROR CODE...
          CALL !ERROR        ; ...DISPLAY THE ERROR CODE.
          GOTO read_end
        ENDIF
        XA = #00H
        ACMLTR = XA
        ASWORK = XA
        ACMLTR+2 = XA
        ASWORK+2 = XA
        L = #00H
        REPEAT               ; DO THIS LOOP 16 TIMES.
          GETI SEL15         ; SELECT A NEW MEMORY BANK.
          ADM = #008H (XA)   ; SELECT AN0 AND BEGIN THE A/D CONVERSION.
          CALL !ADD16        ; ADD 'ASWORK' TO THE SOFTWARE ACCUMULATOR.
          REPEAT
```

```
            UNTIL_BIT(EOC)          ; WAIT UNTIL EOC IS SET (WAIT UNTIL CONVERSION COMPLETE).
            XA = SA                 ; MOVE THE A/D RESULTS FROM...
            GETI SEL0               ;
            ASWORK = XA             ; ...THE SA RESISTER TO THE VARIABLE 'ASWORK'
            L ++                    ; INCREMENT THE COUNTER.
        UNTIL(FOREVER)              ; SKIP THIS INSTRUCTION WHEN L OVERFLOWS.
        CALL !ADD16                 ; ADD THE FINAL A/D READING.
        A2D+0 = ACMLTR+1 (A)        ; GET THE FINAL ANSWER.
        A2D+1 = ACMLTR+2 (A)
        GETI SEL15                  ; SELECT A NEW MEMORY BANK.
        CLR1 PORT8.3                ; TURN THE OP-AMP OFF.
        GETI SEL0                   ; SELECT A NEW MEMORY BANK.
read_end:
        GETI POPMB                  ; RESTORE THE MEMORY BANK
        RET

SHUTDOWN CSEG XBLOCKA

GETI PUSHMB                 ; SAVE THE MEMORY BANK.
        GETI SEL0                   ; SELECT A NEW MEMORY BANK.

IF_BIT(STANDBY && !PORT0:0) ; IF STANDBY MODE IS ENABLED AND THE BUTTON IS DOWN...
            CALL !POWER             ; ...POWER THE SYSTEM DOWN, WAIT FOR BUTTON PUSH.
            A = #1111B              ; ...SET VALUE TO WRITE TO DISPLAY MEMORY.
            CALL !DSPL_INDEX        ; ...TURN ALL LCD SEGMENTS ON.
            B = #07D (A)            ; ...SET THE DELAY TIME OF 4 SECONDS.
            CALL !TIMEOUT           ; ...PAUSE WHILE ALL SEGMENTS ARE ON.
        ENDIF
        GETI POPMB                  ; RESTORE THE MEMORY BANK
        RET

TIMEOUT CSEG XBLOCKA

GETI PUSHMB                 ; SAVE THE MEMORY BANK.
        GETI SEL0                   ; SELECT A NEW MEMORY BANK.
        REPEAT
            CLR1 IRQW               ; CLEAR THE WATCH TIMER FLAG.
            REPEAT
                WTCH_DOG = #00H (XA); CLEAR WATCH DOG TIMER TO PREVENT A TIMEOUT.
                UNTIL_BIT(IRQW)     ; WAIT FOR THE HALF SECOND PULSE.
                B --                ; DECREMENT AND SKIP THE NEXT INSTRUCTION ON A CARRY.
        UNTIL(FOREVER)
        GETI POPMB                  ; RESTORE THE MEMORY BANK.
        RET

TMR_INC CSEG XBLOCKA

GETI PUSHMB                 ; SAVE THE MEMORY BANK
        GETI SEL1                   ; SELECT A NEW MEMORY BANK.
        IF_BIT(!IRQW)               ; IF HALF SECOND INTERRUPT FLAG IS NOT SET...
            GOTO tmr_end            ; ...EXIT THIS ROUTINE
        ENDIF
        CLR1 IRQW                   ; CLEAR THE INTERRUPT FLAG.
        IF_BIT(HALF_SEC)            ; IF HALF_SEC = 1 THEN...
            CLR1 HALF_SEC           ; CLEAR THE BIT.
            GOTO tmr_end            ; EXIT THIS ROUTINE
        ENDIF
        SET1 HALF_SEC
        GETI SEL0                   ; SELECT A NEW MEMORY BANK.
        IF_BIT(Z_FLAG)              ; IF THE PRESSURE IS WITHIN THE ZERO WINDOW...
            A = BTN_CNTR
            HL = #BTN_VAL
            IF(A >= @HL)            ; IF BTN_CNTR >= BTN_VAL...
                CALL !POWER         ; ...POWER THE CHIP DOWN, WAIT FOR A BUTTON PUSH.
                A = #1111B          ; ...SET VALUE TO WRITE TO DISPLAY MEMORY.
                CALL !DSPL_INDEX    ; ...TURN ALL LCD SEGMENTS ON.
                B = #07D (A)        ; ...SET THE DELAY TIME OF 4 SECONDS.
```

```
        CALL !TIMEOUT           ; ...PAUSE WHILE ALL SEGMENTS ARE ON.
      ENDIF
    ENDIF

BTN_CNTR = #00H (A)         ; RESET THE BUTTON COUNTER.
    GETI SEL1                   ; SELECT A NEW MEMORY BANK.
    T0_DSPL ++
    NOP
    HL = #TEN_1                 ; POINT TO VARIABLE WITH VALUE OF 10D.
    IF(T0_DSPL < @HL) (A)       ; IF T0_DSPL < 10D
      GOTO tmr1
    ENDIF
    T0_DSPL = #00H (A)
    T1_DSPL ++
    NOP
    HL = #SIX_1                 ; POINT TO VARIABLE WITH VALUE OF 6D.
    IF(T1_DSPL < @HL) (A)       ; IF T1_DSPL < 06D
      GOTO tmr1
    ENDIF
    T1_DSPL = #00H (A)
    GETI SEL0                   ; SELECT A NEW MEMORY BANK.
    HL = #TMOT_TMR
    CALL !INC8                  ; INCREMENT THE TIME OUT TIMER EVERY MINUTE.
    SBTRCT8 TMOT_TMR, LDOT_VAL
    IF_BIT(!CY)                 ; IF TMOT_TMR - LDOT_VAL >= 0...
      CLR1 LED_ENBL             ; ...DISABLE THE LEDs.
    ENDIF
    SBTRCT8 TMOT_TMR, TMOT_VAL
    IF_BIT(!CY)                 ; IF TMOT_TMR - TMOT_VAL >= 0...
      CALL !POWER               ; ...PLACE THE SYSTEM IN STANDBY MODE, WAIT FOR BUTTON PUSH.
      A = #1111B                ; ...SET VALUE TO WRITE TO DISPLAY MEMORY.
      CALL !DSPL_INDEX          ; ...TURN ALL LCD SEGMENTS ON.
      B = #07D (A)              ; ...SET THE DELAY TIME OF 4 SECONDS.
      CALL !TIMEOUT             ; ...PAUSE WHILE ALL SEGMENTS ARE ON.
      SET1 LED_ENBL             ; ...ENABLE THE LEDs.
      TMOT_TMR = #00H (A)       ; ...INITIALIZE THE TIME-OUT TIMER.
    ENDIF
    GETI SEL1                   ; SELECT A NEW MEMORY BANK.
    T2_DSPL ++
    NOP
    HL = #TEN_1                 ; POINT TO VARIABLE WITH VALUE OF 10D.
    IF(T2_DSPL < @HL) (A)       ; IF T2_DSPL < 10D
      GOTO tmr1
    ENDIF
    T2_DSPL = #00H (A)
    T3_DSPL ++
    NOP
    HL = #TEN_1                 ; POINT TO VARIABLE WITH VALUE OF 10D.
    IF(T3_DSPL < @HL) (A)       ; IF T3_DSPL < 10D
      GOTO tmr1
    ENDIF
    T3_DSPL = #00H (A)
tmr1:
    CALL !LCD_MAIN              ; UPDATE THE LCD.
tmr_end:
    GETI POPMB                  ; RESTORE THE MEMORY BANK
    RET

TRNDCR_CHK CSEG XBLOCKA

GETI PUSHMB                 ; SAVE THE MEMORY BANK.
    GETI SEL15                  ; SELECT A NEW MEMORY BANK.
    PCC = #0011B (A)
    GETI SEL0                   ; SELECT A NEW MEMORY BANK.
    CLR1 TRM_ENBL               ; DISABLE TERMINATION WHEN AN ERROR OCCURS.
    CALL !READ_AD               ; SEE IF A VALID TRANSDUCER IS CONNECTED (SET OR CLEAR THE ERROR BIT).
    WHILE_BIT(ERR_BIT)          ; WHILE THE ERROR BIT IS SET...
      B = #015D (A)             ; ...SET THE DELAY TIME OF 8 SECONDS.
      CALL !TIMEOUT             ; ...PAUSE WHILE ERROR MESSAGE BEING DISPLAYED.
      CALL !POWER               ; ...POWER THE CHIP DOWN.
```

```
        CALL !READ_AD          ; ...SEE IF A VALID TRANSDUCER IS CONNECTED (SET OR CLEAR THE ERROR BIT).
        ENDW
        SET1 TRM_ENBL          ; ENABLE TERMINATION WHEN AN ERROR OCCURS.
        A = #1111B             ; SET VALUE TO WRITE TO DISPLAY MEMORY.
        CALL !DSPL_INDEX       ; TURN ALL LCD SEGMENTS ON.
        B = #07D (A)           ; SET THE DELAY TIME OF 4 SECONDS.
        CALL !TIMEOUT          ; PAUSE WHILE ALL SEGMENTS ARE ON.
        GETI SEL15             ; SELECT A NEW MEMORY BANK.
        PCC = #0010B (A)
        GETI POPMB             ; RESTORE THE MEMORY BANK.
        RET

WRTDTA CSEG XBLOCKA PAGE
TBL1_1: DB 00110101B           ; 0 (ALL 8 BITS ARE USED IN THIS TABLE)
        DB 00110000B           ; 1
        DB 00010111B           ; 2
        DB 00110111B           ; 3
        DB 00110010B           ; 4
        DB 00100111B           ; 5
        DB 00100111B           ; 6
        DB 00110001B           ; 7
        DB 00110111B           ; 8
        DB 00110111B           ; 9
        DB 00110011B           ; A
        DB 00100110B           ; b
        DB 00000101B           ; C
        DB 00110110B           ; d
        DB 00000111B           ; E
        DB 00000011B           ; F

TBL1_2: DB 00000110B           ; 0 (ONLY LOWER 4 BITS ARE USED IN THIS TABLE)
        DB 00000000B           ; 1
        DB 00000100B           ; 2
        DB 00000000B           ; 3
        DB 00000010B           ; 4
        DB 00000010B           ; 5
        DB 00000110B           ; 6
        DB 00000000B           ; 7
        DB 00000110B           ; 8
        DB 00000010B           ; 9
        DB 00000110B           ; A
        DB 00000110B           ; b
        DB 00000110B           ; C
        DB 00000100B           ; d
        DB 00000110B           ; E
        DB 00000110B           ; F

TBL2_1: DB 00000000B           ; 0 (ALL 8 BITS ARE USED IN THIS TABLE)
        DB 00010001B           ; 1
        DB 00100001B           ; 2
WRT_DGT:

GETI PUSHMB            ; SAVE THE MEMORY BANK.
        GETI SEL1              ; SELECT A NEW MEMORY BANK.
        DE = XA                ; LOAD THE TABLE INDEX.
        B = X (A)              ; SAVE THE TABLE NUMBER.
        MOVT XA, @PCDE         ; EXECUTE THE TABLE LOOK-UP.

A <-> X                ; EXCHANGE A AND X.
        @HL = A                ; WRITE DISPLAY PATTERN TO DISPLAY MEMORY.
        A <-> X                ; EXCHANGE A AND X.

L++                    ; POINT TO NEXT DISPLAY MEMORY LOCATION.
        GOTO wrt1
        H++
wrt1:   NOP
        @HL = A                ; WRITE DISPLAY PATTERN TO DISPLAY MEMORY.

IF(B == #00H)          ; IF THE TABLE # IS 0...
          D++                  ; ...POINT TO THE NEXT TABLE
```

```
            MOVT XA, @PCDE         ; ...EXECUTE A SECOND TABLE LOOK-UP.

L++                    ; ...POINT TO THE NEXT DISPLAY MEMORY LOCATION.
            GOTO wrt2
            H++
wrt2:       NOP @HL = A                ; ...WRITE DISPLAY PATTERN TO DISPLAY MEMORY.
        ENDIF
        GETI POPMB                 ; RESTORE THE MEMORY BANK
        RET

CALIBRATE CSEG XBLOCKA

GETI PUSHMB                ; SAVE THE MEMORY BANK
        GETI SEL15                 ; SELECT A NEW MEMORY BANK.
        IF_BIT(PORT1.0)            ; IF CALIBRATION IS NOT REQUESTED...
           GOTO cal_end            ; ...EXIT THIS ROUTINE.
        ENDIF
        PCC = #0011B (A)
        DI IEBT                    ; DISABLE THE MAIN INTERRUPT SERVICE ROUTINE.
        CLR1 IRQCSI                ; CLEAR THE SERIAL INTERRUPT FLAG.
        CSIM = #10000000B (XA)     ; WRITE TO THE SERIAL OPERATION MODE REGISTER (PAGE 5-79).
        SET1 RELT                  ; SET THE SO LATCH (PAGE 5-82).
        CLR1 PORT8.2               ; TURN THE LEDs OFF
        CLR1 PORT8.1

GETI SEL0                  ; SELECT A NEW MEMORY BANK.
        CLR1 TRM_ENBL              ; DISABLE TERMINATION ON AN ERROR.

XA = #00H                  ; CLEAR THE OFFSET.
        OFFSET = XA
        OFFSET+2 = XA

A = #0000B                 ; SET VALUE TO WRITE TO DISPLAY MEMORY.
        CALL !DSPL_INDEX           ; CLEAR THE DISPLAY.
        CALL !HANDSHAKE
        WHILE(FOREVER)
           REPEAT                  ; WAIT UNTIL PC IS HAS STABLE PRESSURE
              CALL !READ_AD        ; READ CURRENT A/D
              DISPLAY A2D,DIGIT3,0 ; DISPLAY THE CURRENT A/D
              DISPLAY A2D+1,DIGIT2,0 ;
           UNTIL_BIT(!PORT1.0)     ; WAIT UNTIL PORT10 GOES LOW.
           CALL !HANDSHAKE
           IF_BIT(PORT0.3)         ; IF SI IS SET (HIGH) BY THE PC...
              BREAK                ; ...STOP SENDING DATA
           ENDIF
           CALL !SEND_A2D
        ENDW
        CALL !GET_PARAM
        GETI SEL15                 ; SELECT A NEW MEMORY BANK.
        PCC = #0010B (A)
        GETI SEL15                 ; SELECT A NEW MEMORY BANK.
        CLR1 IRQCSI                ; CLEAR THE SERIAL INTERRUPT FLAG.
        SET1 CMDT                  ; CLEAR SO LATCH (PAGE 5-82).
        CSIM = #00000000B (XA)     ; WRITE TO THE SERIAL OPERATION MODE REGISTER (PAGE 5-79).
        GETI SEL0                  ; SELECT A NEW MEMORY BANK.
        CALL !CLR_DSPL             ; CLEAR THE LCD DISPLAY.
        ACMLTR = #0E0H (XA)        ; WRITE OUT ' Edd' TO THE DISPLAY TO SIGNAL...
        ACMLTR+2 = #0DDH (XA)      ; ...THAT CALIBRATION IS COMPLETE.
        DISPLAY ACMLTR+1,DIGIT5,0
        DISPLAY ACMLTR+2,DIGIT6,0
        DISPLAY ACMLTR+3,DIGIT7,0

GETI SEL1                  ; SELECT A NEW MEMORY BANK.
        CLR1 (DIGIT6).0            ; CHANGE THE 'd' BEING DISPLAYED IN DIGIT6 TO...
        CLR1 (DIGIT6+1).2          ; ...AN 'n' BY TURNING OFF TWO DISPLAY SEGMENTS.
```

```
            A = #00H                  ; BLANK OUT THE LEADING DIGIT.
            DIGIT4 = A
            DIGIT4+1 = A
            DIGIT4+2 = A
            GETI SEL0                 ; SELECT A NEW MEMORY BANK.
            B = #015D (A)             ; SET PAUSE TIME OF 8 SECONDS.
            CALL !TIMEOUT             ; PAUSE FOR 8 SECONDS.
            CALL !POWER
            CALL !TRNDCR_CHK          ; STANDBY UNTIL BUTTON PUSHED AND VALID TRANSDUCER CONNECTED.
            SET1 STANDBY              ; ENABLE BUTTON PUSH IN MAIN LOOP TO INVOKE STANDBY MODE.
            SET1 TRM_ENBL             ; ENABLE PROGRAM TERMINATION ON AN ERROR.
            CLR1 ERR_BIT              ; CLEAR THE ERROR INDICATOR BIT.
            EI IEBT                   ; ENABLE THE MAIN INTERRUPT SERVICE ROUTINE.
cal_end:
            GETI POPMB                ; RESTORE THE MEMORY BANK
            RET

DUMP_BYTE CSEG XBLOCKA

GETI PUSHMB               ; SAVE THE MEMORY BANK.
            XA = @HL                  ; PUT RAM VALUE IN XA.
            GETI SEL15                ; SELECT A NEW MEMORY BANK.
            SIO = XA                  ; LOAD THE VALUE INTO THE SHIFT REGISTER.
            CALL !HANDSHAKE           ; SHAKE HANDS WITH THE PC.
            WHILE_BIT(!IRQCSI)        ; WAIT UNTIL IRQCSI IS SET.
            ENDW
            CLR1 IRQCSI               ; CLEAR THE 'END-OF-SERIAL-TRANSFER' INTERRUPT.
            SET1 RELT                 ; SET THE SO LATCH.
            GETI POPMB                ; RESTORE THE MEMORY BANK
            RET

DUMP_CHIP CSEG XBLOCKA

GETI PUSHMB               ; SAVE THE MEMORY BANK
            GETI SEL15                ; SELECT A NEW MEMORY BANK.
            IF_BIT(PORT1.0)
              GOTO dump_end
            ENDIF
            PCC = #0011B (A)
            CLR1 IRQCSI               ; CLEAR THE SERIAL INTERRUPT FLAG.
            CSIM = #10000000B (XA)    ; WRITE TO THE SERIAL OPERATION MODE REGISTER (PAGE 5-79).
            SET1 RELT                 ; SET THE SO LATCH (PAGE 5-82).
            GETI SEL1                 ; SELECT A NEW MEMORY BANK.
            CLR1 MAX
            CALL !HANDSHAKE
            GETI SEL0                 ; SELECT A NEW MEMORY BANK.
            HL = #00H                 ; POINT TO THE FIRST LOCATION OF RAM BANK 0
            REPEAT
              REPEAT
                CALL !DUMP_BYTE       ; SEND THE RAM BYTE TO THE PC (POINTED TO BY HL).
                L++                   ; INCREMENT THE POINTER...
                L++                   ; ...BY 2 (DATA TRANSFERRED TO PC IN BYTES).
              UNTIL(FOREVER)
                H++                   ; INCREMENT, SKIP THE NEXT INSTRUCTION ON A  .RY.
              UNTIL(FOREVER)
              GETI SEL1               ; SELECT A NEW MEMORY BANK.
              HL = #00H               ; POINT TO THE FIRST LOCATION OF RAM BANK 0
              REPEAT
                REPEAT
                  CALL !DUMP_BYTE     ; SEND THE RAM BYTE TO THE PC (POINTED TO BY HL).
                  L++                 ; INCREMENT THE POINTER...
                  L++                 ; ...BY 2 (DATA TRANSFERRED TO PC IN BYTES).
                UNTIL(FOREVER)
                H++                   ; INCREMENT, SKIP THE NEXT INSTRUCTION ON A CARRY.
              UNTIL(FOREVER)
              DMP_REG8 SP             ; DUMP THE STACK POINTER.
              DMP_REG8 BT             ; DUMP THE BASIC INTERVAL TIMER.
              DMP_REG8 0F98H          ; DUMP THE WATCH MODE REGISTER.
              DMP_REG8 0FA4H          ; DUMP THE TIMER/EVENT COUNTER REGISTER.
```

```
        DMP_REG8 PSW              ; DUMP THE PROGRAM STATUS WORD.
        DMP_REG4 0FB2H            ; DUMP THE MASTER INTERRUPT FLAG.
        DMP_REG4 0FB8H            ; DUMP IE4, IRQ4, IEBT, AND IRQBT.
        DMP_REG4 0FBAH            ; DUMP IEW AND IRQW.
        DMP_REG4 0FBCH            ; DUMP IETO, AND IRQTO.
        DMP_REG4 0FBDH            ; DUMP IECSI AND IRQCSI.
        DMP_REG4 0FBEH            ; DUMP IE1, IRQ1, IE0, AND IRQ0.
        DMP_REG4 0FBFH            ; DUMP IE2 AND IRQ2.
        DMP_REG8 0FC0H            ; DUMP BSB0 AND BSB1.
        DMP_REG8 0FC2H            ; DUMP BSB2 AND BSB3.
        DMP_REG8 0FD8H            ; DUMP ADM (THE A/D CONVERT MODE REGISTER).
        DMP_REG8 SA               ; DUMP THE SUCCESSIVE APPROXIMATION REGISTER.
        DMP_REG8 0FE0H            ; DUMP CSIM (THE SERIAL OPERATION MODE REGISTER.
        DMP_REG8 SIO              ; DUMP THE SHIFT I/O REGISTER.
        DMP_REG4 PORT0            ; DUMP PORT0
        DMP_REG4 PORT1            ; DUMP PORT1
        DMP_REG4 PORT2            ; DUMP PORT2
        DMP_REG4 PORT3            ; DUMP PORT3
        DMP_REG4 PORT4            ; DUMP PORT4
        DMP_REG4 PORT5            ; DUMP PORT5
        DMP_REG4 PORT6            ; DUMP PORT6
        DMP_REG4 PORT7            ; DUMP PORT7
        DMP_REG4 PORT8            ; DUMP PORT8
        GETI SEL15                ; SELECT A NEW MEMORY BANK.
        PCC = #0000B (A)
        CLR1 IRQCSI               ; CLEAR THE SERIAL INTERRUPT FLAG.
        SET1 CMDT                 ; CLEAR SO LATCH (PAGE 5-82).
        CSIM = #00000000B (XA)    ; WRITE TO THE SERIAL OPERATION MODE REGISTER (PAGE 5-79).
        GETI SEL1                 ; SELECT A NEW MEMORY BANK.
        SET1 MAX
dump_end:
        GETI POPMB                ; RESTORE THE MEMORY BANK
        RET

GET_BYTE CSEG XBLOCKA

PUSH HL                   ; SAVE THE HL REGISTER.
        GETI PUSHMB               ; SAVE THE MEMORY BANK.
        GETI SEL0                 ; SELECT A NEW MEMORY BANK.

ERRCNT = #00H (A)
getbyte1:
        CALL !TRANSMIT
        GETI SEL15                ; SELECT A NEW MEMORY BANK
        XA = SIO
        GETI SEL0
        @HL = XA                  ; GET THE FIRST VALUE RECEIVED.
        CALL !TRANSMIT
        GETI SEL15                ; SELECT A NEW MEMORY BANK
        XA = SIO                  ; GET THE SECOND VALUE RECEIVED.
        GETI SEL0                 ; SELECT A NEW MEMORY BANK.
        ACMLTR = XA
        ASWORK = @HL (XA)

CALL !EQUAL8              ; IF THE VALUE FIRST RECEIVED FROM THE PC IS
        IF_BIT(CY)                ; EQUAL TO THE SECOND VALUE RECEIVED...
          XA = #00H               ; ...SET THE STATUS BYTE...
          CLR1 ERR_BIT            ; ...CLEAR THE BAD DATA FLAG.
        ELSE                      ; ELSE...
          XA = #0FFH              ; ...SET THE STATUS BYTE...
          SET1 ERR_BIT            ; ...SET THE BAD DATA FLAG.
        ENDIF
        GETI SEL15                ; SELECT A NEW MEMORY BANK.
        SIO = XA                  ; LOAD STATUS BYTE.
        CALL !TRANSMIT
        GETI SEL15                ; SELECT A NEW MEMORY BANK.
        XA = SIO                  ; GET VALUE IN SHIFT REGISTER.
        GETI SEL0                 ; SELECT A NEW MEMORY BANK.
        ACMLTR = XA
        ASWORK = #0FFH (XA)
```

```
        CALL !EQUAL8           ; IF THE STATUS BYTE FROM THE PC IS #0FFH, SET CY.
        BC = HL (XA)           ; SAVE HL, (MAY NEED IT IF THERE IS A TRANSMISSION ERROR).
        HL = #ERRCNT           ; POINT TO ERRCNT

IF(@HL == #0FH)        ; IF TRANSMISSION REPEATS = #0FH...
          SET1 TRM_ENBL        ; ...ENABLE PROGRAM TERMINATION...
          ERR = #09H (XA)      ; ...LOAD THE ERROR CODE...
          CALL !ERROR          ; ...DISPLAY THE ERROR CODE.
        ELSEIF_BIT(CY)         ; IF THE STATUS BYTE FROM THE PC IS #0FFH...
          @HL ++               ; ...INCREMENT ERROR COUNTER...
          NOP                  ; ...NOP FOR ADD/SKIP COMMAND...
          HL = BC (XA)         ; ...MAKE HL POINT TO THE TRANSMISSION VALUE AGAIN...
          GOTO getbyte1        ; ...TRY AGAIN.
        ELSEIF_BIT(ERR_BIT)    ; IF ECHOED DATA NOT = TO DATA SENT...
          @HL ++               ; ...INCREMENT ERROR COUNTER...
          NOP                  ; ...NOP FOR ADD/SKIP COMMAND...
          HL = BC (XA)         ; ...MAKE HL POINT TO THE TRANSMISSION VALUE AGAIN...
          GOTO getbyte1        ; ...TRY AGAIN.
        ENDIF ERRCNT = #00H (A)      ; CLEAR THE TRANSMISSION COUNTER.
        GETI POPMB             ; RESTORE THE MEMORY BANK.
        POP HL                 ; RESTORE THE HL REGISTER.
        RET

GET_PARAM CSEG XBLOCKA

GETI PUSHMB            ; SAVE THE MEMORY BANK.
        GETI SEL0              ; SELECT A NEW MEMORY BANK.
        CALL !HANDSHAKE
        HL = #A1               ; USE A1 AS TEMPORARY BYTE.
        CALL !GET_BYTE
        XA = A1                ; GET FLAGS.
        CLR1 CY                ; CLEAR THE CARRY FLAG.
        RORC A                 ; ROTATE 0 BIT INTO CY
        IF_BIT(CY)             ; DETERMINE FLAG.
          SET1 PSI
        ELSE
          CLR1 PSI
        ENDIF
        HL = #A1               ; USE A1 AS TEMPORARY FULL BYTE SINCE "GET_BYTE" PASSES BACK FULL BYTE.
        CALL !GET_BYTE
        BTN_VAL = A1 (A)       ; GET HALF BYTE VALUE.
        HL = #A1               ; USE A1 AS TEMPORARY FULL BYTE SINCE "GET_BYTE" PASSES BACK FULL BYTE.
        CALL !GET_BYTE
        BAND_VAL = A1 (A)      ; GET HALF BYTE VALUE.
        HL = #A1               ; LOW BYTE
        CALL !GET_BYTE
        HL = #A1+2             ; HIGH BYTE
        CALL !GET_BYTE
        HL = #C1               ; LOW BYTE
        CALL !GET_BYTE
        HL = #C1+2             ; HIGH BYTE
        CALL !GET_BYTE
        HL = #A2               ; LOW BYTE
        CALL !GET_BYTE
        HL = #A2+2             ; HIGH BYTE
        CALL !GET_BYTE
        HL = #C2               ; LOW BYTE
        CALL !GET_BYTE
        HL = #C2+2             ; HIGH BYTE
        CALL !GET_BYTE
        HL = #GEL              ; LOW BYTE
        CALL !GET_BYTE
        HL = #GEL+2            ; HIGH BYTE
        CALL !GET_BYTE
        HL = #CH_MODEL         ; ONLY BYTE
        CALL !GET_BYTE
        HL = #DSPL_MAX         ; LOW BYTE
        CALL !GET_BYTE
```

```
        HL = #DSPL_MAX+2        ; HIGH BYTE
        CALL !GET_BYTE
        HL = #DSPL_MIN          ; LOW BYTE
        CALL !GET_BYTE
        HL = #DSPL_MIN+2        ; HIGH BYTE
        CALL !GET_BYTE
        HL = #BGN_INFL          ; LOW BYTE
        CALL !GET_BYTE
        HL = #BGN_INFL+2        ; HIGH BYTE
        CALL !GET_BYTE
        HL = #END_INFL          ; LOW BYTE
        CALL !GET_BYTE
        HL = #END_INFL+2        ; HIGH BYTE
        CALL !GET_BYTE
        HL = #TMOT_VAL          ; ONLY BYTE
        CALL !GET_BYTE
        HL = #LDOT_VAL          ; ONLY BYTE
        CALL !GET_BYTE
        HL = #A2D_MAX           ; ONLY BYTE
        CALL !GET_BYTE
        HL = #A2D_MIN           ; ONLY BYTE
        CALL !GET_BYTE
        HL = #EXTN_MIN          ; ONLY BYTE
        CALL !GET_BYTE
        HL = #NLEG_MAX          ; ONLY BYTE
        CALL !GET_BYTE
        HL = #NLEG_MIN          ; ONLY BYTE
        CALL !GET_BYTE
        HL = #PLEG_MAX          ; ONLY BYTE
        CALL !GET_BYTE
        HL = #PLEG_MIN          ; ONLY BYTE
        CALL !GET_BYTE
        HL = #LED_VAL           ; ONLY BYTE
        CALL !GET_BYTE
        HL = #PRSR_VAL          ; ONLY BYTE
        CALL !GET_BYTE
        HL = #ZWINDOW           ; ONLY BYTE
        CALL !GET_BYTE
        HL = #RZWINDOW          ; ONLY BYTE
        CALL !GET_BYTE
        HL = #BSP_VAL           ; ONLY BYTE
        CALL !GET_BYTE
        GETI POPMB              ; RESTORE THE MEMORY BANK
        RET

HANDSHAKE CSEG XBLOCKA

GETI PUSHMB             ; SAVE THE MEMORY BANK.
        GETI SEL15              ; SELECT A NEW MEMORY BANK.
        REPEAT
        UNTIL_BIT(!PORT1.0 && !PORT1.0); WAIT UNTIL PORT10 IS CLEAR
        SET1 CMDT                       ; CLEAR THE SO LATCH.
        REPEAT
        UNTIL_BIT(PORT1.0 && PORT1.0)   ; WAIT UNTIL PORT10 IS SET.
        SET1 RELT                       ; SET THE SO LATCH.
        GETI POPMB              ; RESTORE THE MEMORY BANK
        RET

SEND_A2D CSEG XBLOCKA

GETI PUSHMB             ; SAVE THE MEMORY BANK.
        GETI SEL0               ; SELECT A NEW MEMORY BANK.
        HL = #EXCTN             ; SEND THE EXCITATION VOLTAGE.
        CALL !SEND_BYTE

HL = #NLEG              ; SEND THE NLEG VOLTAGE.
        CALL !SEND_BYTE

HL = #PLEG              ; SEND THE PLEG VOLTAGE.
        CALL !SEND_BYTE
```

```
        HL = #A2D                ; SEND THE PRESSURE VOLTAGE.
        CALL !SEND_BYTE
        GETI POPMB               ; RESTORE THE MEMORY BANK
        RET

SEND_BYTE CSEG XBLOCKA

PUSH HL                  ; SAVE THE HL REGISTER.
        GETI PUSHMB              ; SAVE THE MEMORY BANK.
        GETI SEL0                ; SELECT A NEW MEMORY BANK.

ERRCNT = #00H (A)
sndbyte1:
        GETI POPMB               ; SELECT THE MEMORY BANK USED WHEN...
        GETI PUSHMB              ; ...THIS ROUTINE WAS INVOKED.
        XA = @HL                 ; PUT RAM VALUE IN XA.
        GETI SEL15               ; SELECT A NEW MEMORY BANK.
        SIO = XA
        CALL !TRANSMIT
        GETI POPMB               ; SELECT THE MEMORY BANK USED WHEN...
        GETI PUSHMB              ; ...THIS ROUTINE WAS INVOKED.
        XA = @HL                 ; GET RAM VALUE.
        GETI SEL15               ; SELECT A NEW MEMORY BANK.
        SIO = XA
        CALL !TRANSMIT
        GETI SEL15               ; SELECT A NEW MEMORY BANK.
        XA = SIO                 ; GET VALUE ECHOED BACK.
        GETI SEL0                ; SELECT A NEW MEMORY BANK.
        ACMLTR = XA              ; LOAD ACMLTR WITH VALUE ECHOED BACK.
        ASWORK = @HL (XA)        ; LOAD VALUE ORIGINALLY SENT.
        CALL !EQUAL8             ; IF THE VALUE ECHOED BACK FROM THE PC IS
        IF_BIT(CY)               ; EQUAL TO THE VALUE ORIGINALLY SENT...
           XA = #000H            ; ...SET THE STATUS BYTE...
           CLR1 ERR_BIT          ; ...CLEAR THE BAD DATA FLAG.
        ELSE                     ; ELSE...
           XA = #0FFH            ; ...SET THE STATUS BYTE...
           SET1 ERR_BIT          ; ...SET THE BAD DATA FLAG.
        ENDIF
        GETI SEL15               ; SELECT A NEW MEMORY BANK.
        SIO = XA                 ; LOAD STATUS BYTE.
        CALL !TRANSMIT
        GETI SEL15               ; SELECT A NEW MEMORY BANK.
        XA = SIO                 ; GET VALUE IN SHIFT REGISTER.
        GETI SEL0                ; SELECT A NEW MEMORY BANK.
        ACMLTR = XA
        ASWORK = #0FFH (XA)
        CALL !EQUAL8             ; IF THE STATUS BYTE FROM THE PC IS #0FFH, SET CY.

BC = HL (XA)             ; SAVE HL, (WILL NEED IT IF THERE IS AN ERROR).
        HL = #ERRCNT             ; POINT TO ERRCNT

IF(@HL == #0FH)          ; IF TRANSMISSION REPEATS = #0FH...
           SET1 TRM_ENBL         ; ...ENABLE PROGRAM TERMINATION...
           ERR = #08H (XA)       ; ...LOAD THE ERROR CODE...
           CALL !ERROR           ; ...DISPLAY THE ERROR CODE.
        ELSEIF_BIT(CY)           ; IF THE STATUS BYTE FROM THE PC IS #0FFH...
           @HL ++                ; ...INCREMENT ERROR COUNTER...
           NOP                   ; ...NOP FOR ADD/SKIP COMMAND...
           HL = BC (XA)          ; ...MAKE HL POINT TO THE TRANSMISSION VALUE AGAIN...
           GOTO sndbyte1         ; ...TRY AGAIN.
        ELSEIF_BIT(ERR_BIT)      ; IF ECHOED DATA NOT = TO DATA SENT...
           @HL ++                ; ...INCREMENT ERROR COUNTER...
           NOP                   ; ...NOP FOR ADD/SKIP COMMAND...
           HL = BC (XA)          ; ...MAKE HL POINT TO THE TRANSMISSION VALUE AGAIN...
           GOTO sndbyte1         ; ...TRY AGAIN.
        ENDIF ERRCNT = #00H (A)        ; CLEAR THE TRANSMISSION COUNTER.
        GETI POPMB               ; RESTORE THE MEMORY BANK.
        POP HL                   ; RESTORE THE HL REGISTER.
        RET
```

```
TRANSMIT CSEG XBLOCKA

GETI PUSHMB            ; SAVE THE MEMORY BANK.
        GETI SEL15             ; SELECT A NEW MEMORY BANK.
        XA <-> SIO             ; ACCESS THE SHIFT REGISTER TO ENABLE...
        XA <-> SIO             ; ...SHIFT OPERATION.

CALL !HANDSHAKE        ; SHAKE HANDS WITH THE PC.
        WHILE_BIT(!IRQCSI)     ; WAIT UNTIL IRQCSI IS SET.
        ENDW
        CLR1 IRQCSI            ; CLEAR THE 'END-OF-SERIAL-TRANSFER' INTERRUPT.
        SET1 RELT              ; SET THE SO LATCH.
        GETI POPMB             ; RESTORE THE MEMORY BANK
        RET

ADD16 CSEG XBLOCKA

PUSH HL                ; SAVE HL.
        GETI PUSHMB            ; SAVE THE MEMORY BANK
        GETI SEL0              ; SELECT A NEW MEMORY BANK.

CLR1 CY
        A = ACMLTR+0           ; GET THE VALUE OF ACMLTR.
        HL = #ASWORK+0         ; POINT TO ASWORK.
        ADDC A,@HL             ; ADD 'ACMLTR' AND 'ASWORK' AND CARRY BIT FROM PREVIOUS NIBBLE.
        ACMLTR+0 = A           ; STORE RESULTS BACK IN A
        A = ACMLTR+1           ; GET THE VALUE OF ACMLTR.
        HL = #ASWORK+1         ; POINT TO ASWORK.
        ADDC A,@HL             ; ADD 'ACMLTR' AND 'ASWORK' AND CARRY BIT FROM PREVIOUS NIBBLE.
        ACMLTR+1 = A           ; STORE RESULTS BACK IN A
        A = ACMLTR+2           ; GET THE VALUE OF ACMLTR.
        HL = #ASWORK+2         ; POINT TO ASWORK.
        ADDC A,@HL             ; ADD 'ACMLTR' AND 'ASWORK' AND CARRY BIT FROM PREVIOUS NIBBLE.
        ACMLTR+2 = A           ; STORE RESULTS BACK IN A
        A = ACMLTR+3           ; GET THE VALUE OF ACMLTR.
        HL = #ASWORK+3         ; POINT TO ASWORK.
        ADDC A,@HL             ; ADD 'ACMLTR' AND 'ASWORK' AND CARRY BIT FROM PREVIOUS NIBBLE.
        ACMLTR+3 = A           ; STORE RESULTS BACK IN A
        IF_BIT((ACMLTR+3).3)
          SET1 CY
        ELSE
          CLR1 CY
        ENDIF
        GETI POPMB             ; RESTORE THE MEMORY BANK
        POP HL                 ; RESTORE HL.
        RET

BCD_NINTH CSEG XBLOCKA

PUSH HL                ; SAVE HL
        GETI PUSHMB            ; SAVE THE MEMORY BANK
        GETI SEL0              ; SELECT A NEW MEMORY BANK.

IF_BIT((ACMLTR+2).0)   ; IF THE NINTH BIT OF THE PRESSURE (IN ACMLTR) IS SET...
          CLR1 CY              ; ADD 256 (DECIMAL) TO 'BDCNV' RESULTS.

GETI SEL1            ; SELECT A NEW MEMORY BANK.
          A = BCD_WRK+0        ; ADD 6 TO THE ONES DIGIT.
          HL = #SIX_1
          ADDS A,#06H
          ADDC A,@HL
          ADDS A,#0AH          ; THE ADD SKIP IS INHIBITED WHEN PRECEDED BY THE ADDC (SEE PAGE 9-5).
          BCD_WRK+0 = A

A = BCD_WRK+1        ; ADD 5 TO THE TENS DIGIT.
          HL = #FIVE_1
          ADDS A,#06H
```

```
        ADDC    A,@HL
        ADDS    A,#0AH          ; THE ADD SKIP IS INHIBITED WHEN PRECEDED BY THE ADDC (SEE PAGE 9-5).
        BCD_WRK+1 = A

A = BCD_WRK+2           ; ADD 2 TO THE HUNDREDS DIGIT.
        HL = #TWO_1
        ADDS    A,#06H
        ADDC    A,@HL
        ADDS    A,#0AH          ; THE ADD SKIP IS INHIBITED WHEN PRECEDED BY THE ADDC (SEE PAGE 9-5).
        BCD_WRK+2 = A
        ENDIF
        GETI    POPMB           ; RESTORE THE MEMORY BANK
        POP     HL              ; RESTORE HL
        RET

BDCNV CSEG XBLOCKA

PUSH    HL              ; SAVE HL
        GETI    PUSHMB          ; SAVE THE MEMORY BANK
        GETI    SEL1            ; SELECT A NEW MEMORY BANK.

MOV     A,#0H
        MOV     BCD_WRK+2,A
        MOV     A,BCD_WRK+1
        XCH     A,E

MOV     A,BCD_WRK
BD:
        MOV     HL,#BCD_WRK     ; DECIMAL ADJUSTMENT (FOR 1ST DIGIT).
        ADDS    A,#6H
        BR      ADD10

MOV     @HL,A           ; INCREMENT 2ND DIGIT.
        INCS    L
        MOV     A,#7H
        ADDS    A,@HL           ; DECIMAL ADJUSTMENT.
        BR      ADD10

INCS    BCD_WRK+2       ; INCREMENT 3RD DIGIT.
CTLOOP:
        MOV     @HL,A           ; ADD 6 AS MANY TIMES AS VALUE OF...
                                ; ...2ND DIGIT.
        DECS    E
        BR      BDX2

GETI    POPMB
        POP     HL
        RET
BDX2:
        MOV     A,BCD_WRK
        ADDS    A,#6H
        BR      BD
ADD10:
        ADDS    A,#0AH
        NOP
        BR      CTLOOP

DIV16 CSEG XBLOCKA

PUSH    HL
        PUSH    DE
        GETI    PUSHMB
        GETI    SEL0
        MOV     DE,#DIVDB

CLRB:
        MOV     A,#0H
        XCH     A,@DE
        INCS    E
        NOP
```

```
            SKE     E,#(DIVDB + 4) AND 0FH
            BR      CLRB

MOV     B,#0CH
LOOP16:
            MOV     DE,#DIVDA
            MOV     A,#0H
SHFT:
            XCH     A,@DE
            INCS    E
            NOP
            SKE     E,#(DIVDA + 8) AND 0FH
            BR      SHFT
SUB:
            MOV     DE,#DIVDB
            MOV     HL,#DIVDC
            CLR1    CY
SLOOP:
            MOV     A,@DE
            SUBC    A,@HL
            XCH     A,@DE
            INCS    L
            NOP
            INCS    E
            NOP
            SKE     L,#(DIVDC + 4) AND 0FH
            BR      SLOOP

NOT1    CY
            SKT     CY
            BR      DO

MOV     DE,#DIVDA
            XCH     A,@DE
            ADDS    A,#1H
            XCH     A,@DE
            BR      SUB
DO:
            MOV     DE,#DIVDB
            MOV     HL,#DIVDC

DIV_ADD:
            MOV     A,@DE
            ADDC    A,@HL
            XCH     A,@DE
            INCS    L
            NOP
            INCS    E
            NOP
            SKE     E,#(DIVDB + 4) AND 0FH
            BR      DIV_ADD
            INCS    B
            BR      LOOP16
            GETI    POPMB
            POP     DE
            POP     HL
            RET

EQUAL8 CSEG XBLOCKA

PUSH HL                 ; SAVE HL.
            GETI PUSHMB             ; SAVE THE MEMORY BANK
            GETI SEL0               ; SELECT A NEW MEMORY BANK.

SET1 CY
            A = ACMLTR+0            ; GET VALUE OF ACMLTR (NIBBLE 0).
            HL = #ASWORK+0          ; POINT TO VALUE OF ASWORK (NIBBLE 0).
            SKE A,@HL               ; IF EQUAL...
            CLR1 CY                 ; ...DO NOT CLEAR THE CARRY FLAG.
```

```
        A = ACMLTR+1          ; GET VALUE OF ACMLTR (NIBBLE 1).
        HL = #ASWORK+1        ; POINT TO VALUE OF ASWORK (NIBBLE 1).
        SKE  A,@HL            ; IF EQUAL...
        CLR1 CY               ; ...DO NOT CLEAR THE CARRY FLAG.
        GETI POPMB            ; RESTORE THE MEMORY BANK
        POP  HL               ; RESTORE HL.
        RET

INC8 CSEG XBLOCKA
        CLR1 CY               ; INITIALIZE THE CARRY FLAG.
        @HL ++
        GOTO inc8end          ; SKIP THIS IF ZERO RESULTED.
        SET1 CY               ; INDICATE A CARRY ON THE FIRST NIBBLE.
        L ++
        GOTO inc1             ; SKIP THIS IF ZERO RESULTED.
        H ++
        GOTO inc1             ; SKIP THIS IF ZERO RESULTED.
inc1:
        @HL ++
        CLR1 CY               ; SKIP THIS IF ZERO RESULTED.
inc8end:
        RET MULT16 CSEG XBLOCKA
        PUSH HL
        PUSH DE
        GETI PUSHMB           ; SAVE THE MEMORY BANK
        GETI SEL0             ; SELECT A NEW MEMORY BANK.
        MOV   XA,#00H
        MOV   MULTB,XA
        MOV   MULTB+2,XA
        MOV   C,#3H
LOOP:
        MOV   B,#7H
        MOV   HL,#MULTB
        MOV   A,#0H
SHLOOP:
        XCH   A,@HL
        INCS  L
        NOP
        DECS  B
        BR    SHLOOP

XCH   A,B
FIGURE:
        DECS  B
        BR    ADD

DECS  C
        BR    LOOP
        GETI  POPMB
        POP   DE
        POP   HL
        RET

ADD:
        PUSH  BC
        CLR1  CY
        MOV   B,#3H
        MOV   DE,#MULTC
        MOV   HL,#MULTB
ADLOOP:
        MOV   A,@DE
        ADDC  A,@HL
        XCH   A,@HL
        INCS  L
        NOP
        INCS  E
        NOP
```

```
        DECS    B
        BR      ADLOOP

POP     BC
        MOV     HL,#MULTA
        NOT1    CY
        SKT     CY
INCA:
        INCS    @HL
        BR      FIGURE

INCS    L
        NOP
        BR      INCA

ROTR CSEG XBLOCKA

GETI PUSHMB             ; SAVE THE MEMORY BANK
        GETI SELO               ; SELECT A NEW MEMORY BANK.
        CLR1 CY                 ; CLEAR THE CARRY FLAG.
        REPEAT
          A = ACMLTR+3          ; ROTATE THE FOURTH NIBBLE RIGHT...
          RORC A                ; ...ONE, (SAVE THE RIGHT BIT IN CY)...
          ACMLTR+3 = A          ; STORE BACK IN FOURTH NIBBLE.

A = ACMLTR+2          ; ROTATE THE THIRD NIBBLE RIGHT...
          RORC A                ; ...ONE, (SAVE THE RIGHT BIT IN CY)...
          ACMLTR+2 = A          ; STORE BACK IN THIRD NIBBLE.

A = ACMLTR+1          ; ROTATE THE SECOND NIBBLE RIGHT...
          RORC A                ; ...ONE, (SAVE THE RIGHT BIT IN CY)...
          ACMLTR+1 = A          ; STORE BACK IN SECOND NIBBLE.

A = ACMLTR+0          ; ROTATE THE FIRST NIBBLE RIGHT...
          RORC A                ; ...ONE, (SAVE THE RIGHT BIT IN CY)...
          ACMLTR+0 = A          ; STORE BACK IN FIRST NIBBLE.

DECS L
          NOP
        UNTIL(L == #00H)
        GETI POPMB              ; RESTORE THE MEMORY BANK
        RET

SUB16 CSEG XBLOCKA

PUSH HL                 ; SAVE THE HL REGISTER
        GETI PUSHMB             ; SAVE THE MEMORY BANK
        GETI SELO               ; SELECT A NEW MEMORY BANK.

CLR1 CY
        A = ACMLTR+0            ; GET THE VALUE OF ACMLTR.
        HL = #ASWORK+0          ; POINT TO ASWORK.
        SUBC A,@HL              ; SUBTRACT 'ASWORK' AND THE CARRY BIT (FROM THE PREVIOUS NIBBLE) FROM 'ACMLTR'.
        ACMLTR+0 = A            ; STORE RESULTS BACK IN ACMLTR
        A = ACMLTR+1            ; GET THE VALUE OF ACMLTR.
        HL = #ASWORK+1          ; POINT TO ASWORK.
        SUBC A,@HL              ; SUBTRACT 'ASWORK' AND THE CARRY BIT (FROM THE PREVIOUS NIBBLE) FROM 'ACMLTR'.
        ACMLTR+1 = A            ; STORE RESULTS BACK IN ACMLTR
        A = ACMLTR+2            ; GET THE VALUE OF ACMLTR.
        HL = #ASWORK+2          ; POINT TO ASWORK.
        SUBC A,@HL              ; SUBTRACT 'ASWORK' AND THE CARRY BIT (FROM THE PREVIOUS NIBBLE) FROM 'ACMLTR'.
        ACMLTR+2 = A            ; STORE RESULTS BACK IN ACMLTR
        A = ACMLTR+3            ; GET THE VALUE OF ACMLTR.
        HL = #ASWORK+3          ; POINT TO ASWORK.
        SUBC A,@HL              ; SUBTRACT 'ASWORK' AND THE CARRY BIT (FROM THE PREVIOUS NIBBLE) FROM 'ACMLTR'.
        ACMLTR+3 = A            ; STORE RESULTS BACK IN ACMLTR
        IF_BIT((ACMLTR+3).3)
          SET1 CY
        ELSE
          CLR1 CY
        ENDIF
        GETI POPMB              ; RESTORE THE MEMORY BANK
        POP HL
        RET
```

```
TWOS_CMP CSEG XBLOCKA

GETI PUSHMB         ; SAVE THE MEMORY BANK.
        GETI SEL0           ; SELECT A NEW MEMORY BANK.
        XCH A, ACMLTR+0
        NOT A
        XCH A, ACMLTR+0
        XCH A, ACMLTR+1
        NOT A
        XCH A, ACMLTR+1
        XCH A, ACMLTR+2
        NOT A
        XCH A, ACMLTR+2
        XCH A, ACMLTR+3
        NOT A
        XCH A, ACMLTR+3
        HL = #ACMLTR+0      ; INCREMENT THE FIRST NIBBLE.
        @HL ++
        GOTO twosend HL = #ACMLTR+1      ; IF CARRY RESULTED FROM PREVIOUS NIBBLE..
        @HL ++              ; ...INCREMENT THIS NIBBLE.
        GOTO twosend HL = #ACMLTR+2      ; IF CARRY RESULTED FROM PREVIOUS NIBBLE..
        @HL ++              ; ...INCREMENT THIS NIBBLE.
        GOTO twosend HL = #ACMLTR+3      ; IF CARRY RESULTED FROM PREVIOUS NIBBLE..
        @HL ++              ; ...INCREMENT THIS NIBBLE.
        GOTO twosend
twosend:
        GETI POPMB          ; RESTORE THE MEMORY BANK
        RET

END
```

What is claimed is:

1. A system for monitoring inflation of a balloon-type member and for automatically recording inflation data, comprising:

a syringe connected to said member through tubing, said syringe comprising a barrel and a plunger selectively operable to inflate said member by applying fluid pressure to said member through said tubing by sliding the plunger within the barrel;

transducer means for sensing said applied fluid pressure and for outputting an electrical signal proportional to said sensed fluid pressure, said transducer means being placed in fluid communication with said syringe and the tubing connected thereto;

electronic circuit means, electrically connected to said transducer means and mounted on said syringe barrel, for receiving said electrical signal and for electronically processing said signal so as to derive and so as to automatically display or record therefrom electronic data representing the magnitude of said fluid pressure applied to said member and the length of time said fluid pressure is applied to said member; and display means, electrically connected to said electronic circuit means and mounted on said syringe barrel, for outputting a visual display of the magnitude of said applied fluid pressure and the corresponding length of time said pressure is applied to said member.

2. A system as defined in claim 1 wherein said transducer means comprises a piezoresistive semiconductor transducer.

3. A system as defined in claim 2 wherein said transducer is mounted to said syringe barrel.

4. A system as defined in claim 1 wherein said transducer means, said electronic circuit means and said display means are all included within a controller mounted on said syringe barrel.

5. A system as defined in claim 1 wherein said electronic circuit means comprises:

means for amplifying said signal output by the transducer means;

means for converting said amplified signal from an analog to a digital form;

digital processor means for processing said digital form of said signal so as to derive therefrom digital data which represents the magnitude of said applied pressure and the length of time pressure is applied to said member;

data memory means for storing the digital data derived by said digital processor means; and program memory means for storing machine-readable instructions utilized by said digital processor means to derive, store, retrieve and display said digital data.

6. A system as defined in claim 5 wherein said transducer means, said electronic circuit means and said display means are all included within a controller mounted on said syringe barrel.

7. A system as defined in claims 4 or 6 further comprising battery means included within said controller for providing electrical power to said transducer means, said electronic circuit means and said display means.

8. A system as defined in claim 6 wherein said controller comprises a control panel and wherein said display means comprises a digital readout on said panel.

9. A system as defined in claim 8 further comprising means for lighting said digital readout to provide increased visibility.

10. A system as defined in claim 2 wherein said lighting means comprises an LED at opposite ends of said digital readout.

11. A system as defined in claim 8 wherein said digital processor means is programmed to turn said lighting means on when inflation pressure is sensed and to turn said lighting means off if no change in inflation pressure is sensed within a selected interval of time.

12. A system as defined in claim 8 wherein said control panel comprises switch means for retrieving and reviewing previously stored digital data at said digital readout.

13. A system as defined in claim 12 wherein said switch means comprises an elastomeric button switch and means for preventing entry of liquids at said button switch.

14. A system for generating a series of discrete balloon catheter inflations and for automatically displaying and recording inflation data corresponding to each said discrete inflation, comprising:
(a) a control syringe connected to a balloon of said balloon catheter through tubing, said syringe comprising a barrel and a plunger selectively operable to first apply and then remove positive fluid pressures to said balloon through said tubing by sliding the plunger within the barrel;
(b) a piezoresistive semiconductor transducer connected in fluid communication with said fluid pressures applied to said balloon catheter such that said transducer senses fluid pressures applied to said balloon and generates an electrical signal proportional to the sensed fluid pressure; and
(c) a controller mounted on said syringe barrel and electrically connected to said transducer, said controller comprising:
  (i) means for amplifying said signal output by said transducer;
  (ii) means for converting said amplified signal from an analog to a digital form;
  (iii) digital processor means for processing said digital form of said signal so as to electronically monitor, display and record inflation pressure applied to said balloon and the duration of inflation by performing the steps of:
    (A) deriving data from said digital signals which represents a numerical value of the magnitude of said applied pressure;
    (B) deriving data from said digital signals which represent a numerical value of the duration of said inflation pressure;
    (C) electronically storing all said derived data; and
    (D) displaying said numerical values in a visually perceptible manner to a system user;
  (iv) data memory means for storing the digital data derived by said digital processor means;
  (v) program memory means for storing machine-readable instructions utilized by said digital processor means to perform said steps; and
  (vi) display means for visually identifying said numerical value of the magnitude of said applied pressure together with a corresponding numerical value of said duration of said inflation pressure.

15. A system as defined in claim 14 wherein said transducer is included within said controller.

16. A system as defined in claim 15 further comprising battery means included within said controller for providing electrical power to said transducer and to each said means of said controller.

17. A system as defined in claim 16 wherein said controller comprises a control panel and wherein said display means comprises a digital readout on said panel.

18. A system as defined in claim 17 further comprising means for lighting said digital readout to provide increased visibility.

19. A system as defined in claim 18 wherein said lighting means comprises an LED at opposite ends of said digital readout.

20. A system as defined in claim 17 wherein said digital processor means is programmed to turn said lighting means on when inflation pressure is sensed and to turn said lighting means off if no change in inflation pressure is sensed within a selected interval of time.

21. A system as defined in claim 17 wherein said control panel comprises switch means for retrieving and reviewing previously stored digital data at said digital readout.

22. A system as defined in claim 21 wherein said switch means comprises an elastomeric button switch and means for preventing entry of liquids at said button switch.

23. In a system for generating a series of discrete balloon catheter inflations and for automatically recording inflation data derived from an electrical signal corresponding to each said discrete inflation, an improved control syringe comprising:
a barrel comprised of plastic material and connected through tubing to a balloon of said balloon catheter;
a plunger comprised of plastic material and slidably mounted within said barrel and operable to selectively apply and then release fluid pressure on said balloon by movement of the plunger within said barrel;
a piezoresistive semiconductor transducer mounted on said syringe barrel and in fluid communication with the interior of said syringe barrel through a hole formed in a side of said syringe barrel such that changes in fluid pressure applied to said balloon by sliding said plunger are sensed by said transducer, which in turn generates an electrical signal proportional to the sensed positive fluid pressure;
means for preventing said syringe plunger from ever occluding said hole; and
whereby toxic elements cannot be introduced into said fluid from said transducer.

24. In a system comprising an inflatable balloon member connected through tubing to a syringe barrel and wherein a plunger slidably mounted within said barrel is moveable to selectively apply and then release fluid pressures exerted on said balloon member so as to selectively inflate said balloon member one or more times, a method of monitoring, displaying and automatically recording inflation data comprising the steps of:
electronically sensing whether a transducer is connected to said system and if so, electronically measuring any offset signal at zero pressure;
electronically comparing the measured offset signal with a previously electronically stored value of an offset signal, and if the measured offset signal is within a selected range of the stored offset signal, using the measured offset signal in subsequent determinations of applied pressure, and if the measured offset signal is not within said selected range, using the previously stored value of the offset signal in subsequent determinations of applied pressure;

selectively increasing fluid pressure applied to the balloon member by pushing said plunger into said syringe barrel;

sensing the fluid pressure applied by said syringe and outputting an electrical signal proportional to the sensed fluid pressure;

amplifying said electrical output signal;

converting said amplified signal from an analog to a digital form;

digitally processing the digital form of said signal so as to derive therefrom digital data from which said magnitude of said applied fluid pressures and the length of time said fluid pressures are applied to said balloon member may be output in numeric form;

storing the digital data;

selectively retrieving and outputting said stored digital data in a form which can be visually perceived and read by an operator of the system; and releasing the fluid pressure applied to the balloon member by pulling said plunger toward the rear of the syringe barrel.

25. A method as defined in claim 24 further comprising the step of repeating each of said steps in connection with a second inflation of the balloon member.

26. In a system comprising a balloon catheter connected through tubing to a syringe barrel and wherein by movement of a plunger through the barrel fluid pressure applied to a balloon of the balloon catheter may be selectively increased or decreased, a method of electronically monitoring, displaying and recording the applied fluid pressure each time the balloon is inflated, the method comprising the steps of:

electronically sensing whether a transducer is connected to said system and if so, electronically measuring any offset signal at zero pressure;

electronically comparing the measured offset signal with a previously electronically stored value of an offset signal, and if the measured offset signal is within a selected range of the stored offset signal, using the measured offset signal in subsequent determinations of applied pressure, and if the measured offset signal is not within said selected range, using the previously stored value of the offset signal in subsequent determinations of applied pressure;

inflating the balloon a first time by pushing the plunger into the syringe barrel so as to apply a positive inflation pressure to the balloon;

sensing any applied fluid pressure using a piezoresistive semiconductor transducer placed in fluid communication with the applied pressure, and generating at said transducer an electrical signal proportional in magnitude and duration to said applied pressure;

converting said electrical signal to a series of corresponding digital signals and inputting said digital signals to a digital processor;

processing the digital signals using said digital processor to carry out a programmed method comprising the steps of:

deriving data from said digital signals which represents a numerical value of the magnitude of said applied pressure;

deriving data from said digital signals which represent a numerical value of the duration of said positive inflation pressure;

electronically storing all said derived data; and displaying said numerical values in a visually perceptible manner to a system user;

deflating the balloon by withdrawing the syringe plunger so as to remove the positive fluid pressure applied to the balloon catheter; and repeating each of the above-recited steps for a second inflation of the balloon.

27. A method as defined in claim 26 wherein said step of displaying said numerical values comprises the steps of:

connecting a digital display means and a backlighting means to a battery source; and disconnecting at least one of said digital display means and said backlighting means from said battery source if a zero pressure is sensed during a selected time interval.

28. A method as defined in claim 27 wherein said step of displaying said numerical values further comprises the steps of:

disconnecting the other of said digital display means and said backlighting means from said battery source if a zero pressure is sensed during a second selected time interval; and re-connecting said digital display means and said backlighting means to said battery source at any time by activating a switch means.

29. In a system comprising a balloon catheter connected through tubing to a syringe barrel and wherein by movement of a plunger through the barrel fluid pressure applied to a balloon of the balloon catheter may be selectively increased or decreased, a method of electronically monitoring, displaying and recording the applied fluid pressure each time the balloon is inflated, the method comprising the steps of:

inflating the balloon a first time by pushing the plunger into the syringe barrel so as to apply a positive inflation pressure to the balloon;

sensing any applied fluid pressure using a piezoresistive semiconductor transducer placed in fluid communication with the applied pressure, and generating at said transducer an electrical signal proportional in magnitude and duration to said applied pressure;

converting said electrical signal to a series of corresponding digital signals and inputting said digital signals to a digital processor;

processing the digital signals using said digital processor to carry out a programmed method comprising the steps of:

deriving data from said digital signals which represents a numerical value of the magnitude of said applied pressure;

deriving data from said digital signals which represent a numerical value of the duration of said positive inflation pressure;

electronically storing all said derived data;

connecting a digital display means and a backlighting means to a battery source; and disconnecting at least one of said digital display means and said backlighting means from said battery source if a zero pressure is sensed during a selected time interval;

deflating the balloon by withdrawing the syringe plunger so as to remove the positive fluid pressure applied to the balloon catheter; and repeating each of the above-recited steps for a second inflation of the balloon.

30. A method as defined in claim 29 wherein said step of displaying said numerical values further comprises the steps of:

disconnecting the other of said digital display means and said backlighting means from said battery source if a zero pressure is sensed during a second selected time interval; and re-connecting said digital display means and said backlighting means to said battery source at any time by activating a switch means.

31. In a system comprising an inflatable balloon member connected through tubing to a syringe barrel and wherein a plunger slidably mounted within said barrel is moveable to selectively apply and then release fluid pressures exerted on said balloon member so as to selectively inflate said balloon member one or more times, a method of monitoring, displaying and automatically recording inflation data comprising the steps of:

electronically sensing whether a transducer is connected to said system and if so, electronically measuring any offset signal at zero pressure;

electronically comparing the measured offset signal with one of several previously stored values corresponding to different offset signals, whereby the measured offset signal is determined to be within one of several previously selected ranges;

outputting a visual display identifying a selected range and a corresponding type of syringe that is in use;

using selected parameters previously electronically stored for the type of syringe in use in subsequent determinations of applied pressure;

selectively increasing fluid pressure applied to the balloon member by pushing said plunger into said syringe barrel;

sensing the fluid pressure applied by said syringe and outputting an electrical signal proportional to the sensed fluid pressure;

amplifying said electrical output signal;

converting said amplified signal from an analog to a digital form;

digitally processing the digital form of said signal so as to derive therefrom digital data from which said magnitude of said applied fluid pressures and the length of time said fluid pressures are applied to said balloon member may be output in numeric form;

storing the digital data;

selectively retrieving and outputting said stored digital data in a form which can be visually perceived and read by an operator of the system; and releasing the fluid pressure applied to the balloon member by pulling said plunger toward the rear of the syringe barrel.

* * * * *

UNITED STATES PATENT AND TRADEMARK OFFICE
CERTIFICATE OF CORRECTION

PATENT NO. : 5,201,753
DATED : April 13, 1993
INVENTOR(S) : FRED P. LAMPROPOULOS et al.

It is certified that error appears in the above-identified patent and that said Letters Patent is hereby corrected as shown below:

Column 12, line 17, "Way" should be --way--
Column 15, line 26, "again" should be --against--
Column 16, line 59, after "transducer 42" insert --is essentially the same as the transducer previously described--
Column 21, line 54, "beings" should be --begins--

Signed and Sealed this

First Day of February, 1994

Attest:

BRUCE LEHMAN

Attesting Officer

Commissioner of Patents and Trademarks